US010945771B2

(12) United States Patent
Clausen et al.

(10) Patent No.: US 10,945,771 B2
(45) Date of Patent: Mar. 16, 2021

(54) AZABICYCLO[4.1.0]HEPTANE ALLOSTERIC MODULATORS OF THE M4 MUSCARINIC ACETYLCHOLINE RECEPTOR

(71) Applicant: Merck Sharp & Dohme Corp., Rahway, NJ (US)

(72) Inventors: Dane James Clausen, Bridgewater, NJ (US); James I. Fells, Whitehouse Station, NJ (US); Joseph A. Kozlowski, Princeton, NJ (US); Ping Liu, Westfield, NJ (US); Robert D. Mazzola, Jr., Stewartsville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/620,046

(22) PCT Filed: Jun. 4, 2018

(86) PCT No.: PCT/US2018/035772
§ 371 (c)(1),
(2) Date: Dec. 6, 2019

(87) PCT Pub. No.: WO2018/226545
PCT Pub. Date: Dec. 13, 2018

(65) Prior Publication Data
US 2020/0095262 A1 Mar. 26, 2020

Related U.S. Application Data

(60) Provisional application No. 62/517,375, filed on Jun. 9, 2017.

(51) Int. Cl.
| | | |
|---|---|---|
| *A61B 17/70* | (2006.01) | |
| *A61B 17/17* | (2006.01) | |
| *A61B 17/34* | (2006.01) | |
| *A61B 17/86* | (2006.01) | |
| *C07D 471/04* | (2006.01) | |
| *C07D 471/14* | (2006.01) | |
| *C07D 498/14* | (2006.01) | |
| *A61B 17/56* | (2006.01) | |
| *A61B 90/00* | (2016.01) | |

(52) U.S. Cl.
CPC ...... *A61B 17/7074* (2013.01); *A61B 17/1757* (2013.01); *A61B 17/3472* (2013.01); *A61B 17/7062* (2013.01); *A61B 17/7071* (2013.01); *A61B 17/864* (2013.01); *A61B 17/8685* (2013.01); *C07D 471/04* (2013.01); *C07D 471/14* (2013.01); *C07D 498/14* (2013.01); *A61B 2017/564* (2013.01); *A61B 2090/037* (2016.02)

(58) Field of Classification Search
CPC ............ A61B 17/1757; A61B 17/3472; A61B 17/7062; A61B 17/7071; A61B 17/864; A61B 17/8685; C07D 471/04; C07D 471/14; C07D 498/14
See application file for complete search history.

(56) References Cited

U.S. PATENT DOCUMENTS

| | | | |
|---|---|---|---|
| 8,735,423 B2 | 5/2014 | Nirogi et al. | |
| 10,329,289 B2 * | 6/2019 | Bao | C07D 491/048 |
| 10,351,564 B2 * | 7/2019 | Gao | C07D 491/052 |
| 2007/0213342 A1 * | 9/2007 | Chapdelaine | C07D 491/04 514/253.04 |
| 2017/0183342 A1 | 6/2017 | Bao et al. | |
| 2018/0002331 A1 | 1/2018 | Zhang et al. | |
| 2019/0000824 A1 * | 1/2019 | Acton, III | A61K 31/437 |
| 2019/0315708 A1 * | 10/2019 | Bao | A61P 25/00 |
| 2019/0315762 A1 * | 10/2019 | Gao | A61P 25/00 |
| 2020/0095261 A1 * | 3/2020 | Gao | C07D 498/04 |

FOREIGN PATENT DOCUMENTS

| | | |
|---|---|---|
| WO | WO2011087776 A1 | 7/2011 |
| WO | 2013063549 A1 | 5/2013 |
| WO | 2015163485 A1 | 10/2015 |

OTHER PUBLICATIONS

Chan; Proceedings of the National Academy of Sciences 2008, 105, 10978-10983. (Year: 2008).*
Foster; Neuropsychiatric Disease and Treatment 2014, 10, 183-191. (Year: 2014).*
Scarr; CNS Neuroscience & Therapeutics 2012, 18, 369-379. (Year: 2012).*
Vardigan; Psychopharmacology 2015, 232, 1859-1866. (Year: 2015).*
National Center for Biotechnology Information. PubChem Compound Database; CID=71149332, https://pubchem.ncbi.nlm.nih.gov/compound/71149332 (accessed Oct. 2, 2018).
International Search Report and Written Opinion for PCT/US2018/35772; dated Sep. 7, 2018; 8 pages.
European Search Report, Application EP18812747.6, 6 pages (Dec. 11, 2020).
Jakubik, Jan et al., Allosteric Modulation of Muscarinic Acetylcholine Receptors, Pharmaceuticals, 2010, 2838-2860, 3(9).

* cited by examiner

*Primary Examiner* — Daniel R Carcanague
(74) *Attorney, Agent, or Firm* — J. Eric Thies; John C. Todaro

(57) ABSTRACT

The present invention is directed to azabicyclo[4.1.0]heptane compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

18 Claims, No Drawings

AZABICYCLO[4.1.0]HEPTANE ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US2018/035772, filed Jun. 4, 2018, which claims priority under 35 U.S.C. § 119(e) from U.S. Ser. No. 62/517,375, filed Jun. 9, 2017.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to azabicyclo[4.1.0] heptane compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

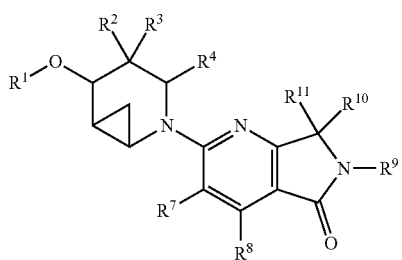

I wherein:

R¹ is selected from:
(1) hydrogen;
(2) —C$_{1-6}$alkyl, which is unsubstituted or substituted with substituents selected from: hydroxy, fluoro, —CN, —O—C$_{1-6}$alkyl, C$_{3-6}$cycloalkyl, bicycle[1.1.1]pentane, tetrahydrofuranyl, phenyl, pyridyl, oxazolyl, —NH$_2$, —NH(C$_{1-6}$alkyl), —N(—C$_{1-6}$alkyl)$_2$, and —N(C═O)—C$_{1-6}$alkyl, wherein the C$_{1-6}$alkyl or C$_{3-6}$cycloalkyl is unsubstituted or substituted with substituents selected from: fluoro, cyano, CF$_3$, C$_{1-6}$ alkyl or —O—C$_{1-6}$ alkyl;
(3) a phenyl, heteroaryl or heterocyclyl ring, wherein the phenyl, heteroaryl or heterocyclyl ring is substituted with one or more R$^{1a}$, R$^{1b}$ and R$^{1c}$, wherein R$^{1a}$, R$^{1b}$ and R$^{1c}$ are independently selected from:
(a) hydrogen,
(b) hydroxy,
(c) halogen,
(d) C$_{1-6}$ alkyl, which is unsubstituted or substituted with substituents selected from: hydroxy, cyclopropyl, cyclobutyl, cyclopentyl, azetidinyl, fluoro, —OCH$_3$, —OCH$_2$CH$_2$OCH$_3$, —(C═O)—C$_{1-6}$ alkyl, —NH$_2$, —NH(C$_{1-6}$alkyl), —N(C$_{1-6}$ alkyl)$_2$, and —N(C$_{3-6}$cycloalkyl),
(e) —O—C$_{1-6}$ alkyl, which is unsubstituted or substituted with substituents selected from: hydroxy, cyclopropyl, cyclobutyl, cyclopentyl, azetidinyl, fluoro, —OCH$_3$, —NH$_2$, —NH(C$_{1-6}$ alkyl), —N(C$_{1-6}$ alkyl)$_2$, —N(C$_{3-6}$cycloalkyl), and —NH(C═O)(C$_{1-6}$alkyl),
(f) C$_{3-6}$cycloalkyl, which is unsubstituted or substituted with substituents selected from: C$_{1-6}$alkyl, hydroxy, cyclopropyl, cyclobutyl, cyclopentyl, azetidinyl, fluoro, —OCH$_3$, —NH$_2$, —NH(C$_{1-6}$alkyl), —N(C$_{1-6}$ alkyl)$_2$, and —N(C$_{3-6}$ cycloalkyl),
(g) —NH$_2$,
(h) —NH(C$_{1-6}$alkyl),
(i) —NH(C$_{2-6}$alkyl)-OH,
(l) —N(C$_{1-6}$alkyl)$_2$,
(k) —N(C$_{3-6}$cycloalkyl),
(l) —SO$_2$—C$_{1-6}$alkyl,
(m) —(C═O)H,
(n) —(C═O)—C$_{1-6}$alkyl,
(o) —(C═O)O—C$_{1-6}$alkyl, and
(p) —CN;

R² and R³ are independently selected from:
(1) hydrogen,
(2) fluoro,
(3) hydroxy, and
(4) —CH$_3$;

R⁴ is hydrogen or methyl;

R⁷ and R⁸ are independently selected from:
(1) hydrogen,
(2) C$_{1-6}$ alkyl, which is unsubstituted or substituted with substituents selected from: hydroxy, fluoro, and —OCH$_3$,
(3) —CH═CH$_2$,
(4) cyclopropyl,
(5) -fluoro,
(6) -chloro,
(7) -bromo,
(8) —CN,
(9) —(C═O)H, and
(10) —(C═O)O—C$_{1-6}$alkyl;

R⁹ is selected from:
(1) hydrogen,
(2) —C$_{1-6}$alkyl, which is unsubstituted or substituted with substituents selected from: hydroxy, methoxy, fluoro, —C(C═O)O—C$_{1-6}$alkyl, —CN, —NH$_2$, —NH(C$_{1-6}$ alkyl), —N(C$_{1-6}$ alkyl)$_2$, —C(C═O)NH$_2$, —C(C═O)OH, —SO$_2$C$_{1-6}$alkyl, oxetanyl, or pyridyl;
(3) —C$_{3-6}$cycloalkyl, which is unsubstituted or substituted with substituents selected from: hydroxy, and C$_{1-6}$ alkyl-hydroxy,
(4) oxetanyl,
(6) tetrahydrofuranyl, and
(6) —C(C═O)O—C$_{1-6}$alkyl;

each of R¹⁰ and R¹¹ is independently selected from:
(1) hydrogen,
(2) —OH,
(3) —CH$_3$,
(4) —CH$_2$OH,
(5) —CH$_2$CH$_2$OH, and
(6) —C(CH$_3$)$_2$OH,
or R¹⁰ and R¹¹ taken together form a cyclopropyl group, a ═CH$_2$ group or a keto group,
or R⁹ and R¹⁰ taken together form a piperidine, piperazine or morpholine ring, which is unsubstituted or substituted with substituents selected from: hydroxy, methoxy, and —C$_{1-6}$alkyl;

or a pharmaceutically acceptable salt thereof.

An embodiment of the present invention includes compounds of the formula Ia:

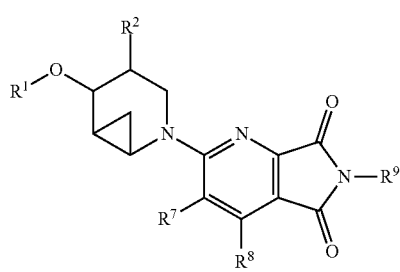

Ia wherein R¹, R², R⁷, R⁸ and R⁹ are defined herein; or a pharmaceutically acceptable salt thereof.

An embodiment of the present invention includes compounds of the formula Ib:

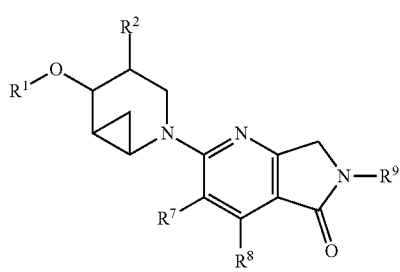

Ib wherein R¹, R², R⁷, R⁸ and R⁹ are defined herein; or a pharmaceutically acceptable salt thereof.

An embodiment of the present invention includes compounds of the formula Ic:

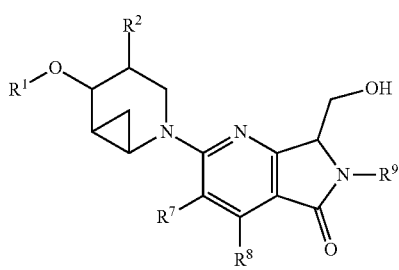

Ic wherein $R^1$, $R^2$, $R^7$, $R^8$ and $R^9$ are defined herein; or a pharmaceutically acceptable salt thereof.

An embodiment of the present invention includes compounds of the formula IIa:

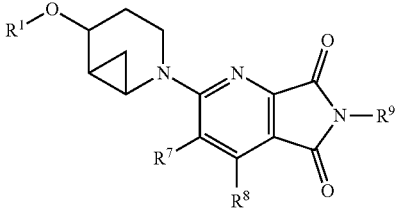

IIa wherein $R^1$, $R^7$, $R^8$ and $R^9$ are defined herein; or a pharmaceutically acceptable salt thereof.

An embodiment of the present invention includes compounds of the formula IIb:

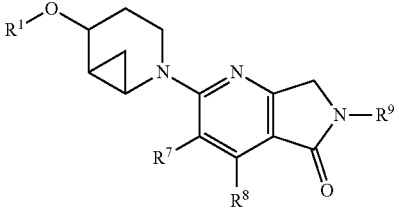

IIb wherein $R^1$, $R^7$, $R^8$ and $R^9$ are defined herein; or a pharmaceutically acceptable salt thereof.

An embodiment of the present invention includes compounds of the formula IIc:

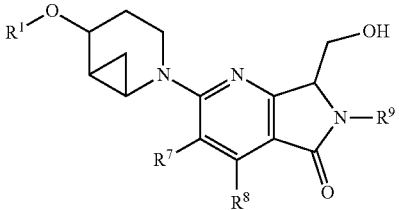

IIc wherein $R^1$, $R^7$, $R^8$ and $R^9$ are defined herein; or a pharmaceutically acceptable salt thereof.

An embodiment of the present invention includes compounds of the formula IIIa:

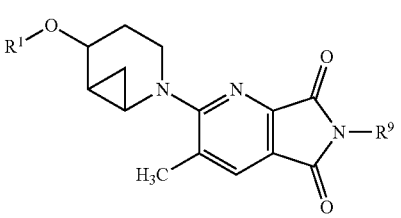

IIIa wherein $R^1$ and $R^9$ are defined herein; or a pharmaceutically acceptable salt thereof.

An embodiment of the present invention includes compounds of the formula IIIb:

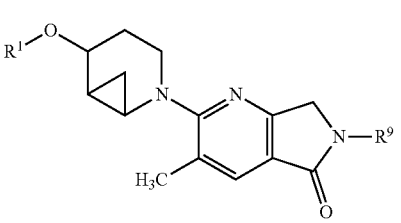

IIIb wherein $R^1$ and $R^9$ are defined herein; or a pharmaceutically acceptable salt thereof.

An embodiment of the present invention includes compounds of the formula IIIc:

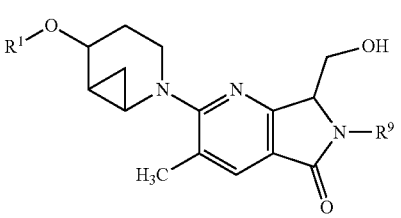

IIIc wherein $R^1$ and $R^9$ are defined herein; or a pharmaceutically acceptable salt thereof.

An embodiment of the present invention includes compounds of the formula IVa:

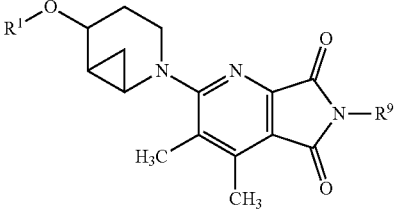

IVa wherein $R^1$ and $R^9$ are defined herein; or a pharmaceutically acceptable salt thereof.

An embodiment of the present invention includes compounds of the formula IVb:

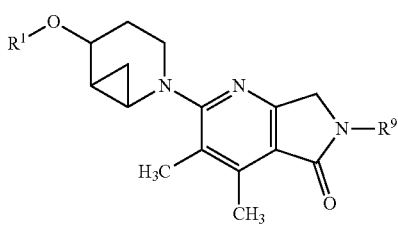

wherein $R^1$ and $R^9$ are defined herein; or a pharmaceutically acceptable salt thereof.

An embodiment of the present invention includes compounds of the formula IVc:

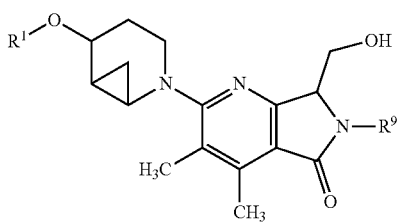

wherein $R^1$ and $R^9$ are defined herein; or a pharmaceutically acceptable salt thereof.

An embodiment of the present invention includes compounds wherein $R^1$ is selected from: benzodioxolyl, benzoimidazolyl, benzoxazolyl, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more of $R^{1a}$, $R^{1b}$ and $R^{1c}$.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from:
(a) hydrogen,
(b) hydroxyl,
(c) halogen,
(d) $C_{1-6}$ alkyl, which is unsubstituted or substituted with substituents selected from: hydroxy, fluoro, and —$OCH_3$,
(e) —O—$C_{1-6}$alkyl, which is unsubstituted or substituted with substituents selected from: hydroxy, fluoro, and —$OCH_3$,
(f) $C_{3-6}$cycloalkyl, which is unsubstituted or substituted with a substituent selected from: $C_{1-6}$alkyl and hydroxy; and
(g) —CN.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from:
(a) hydrogen,
(b) hydroxyl,
(c) halogen,
(d) $C_{1-3}$alkyl, which is unsubstituted or substituted with a substituent selected from: hydroxy, 1-3 fluoro, and —$OCH_3$,
(e) —O—$C_{1-3}$alkyl, which is unsubstituted or substituted with a substituent selected from: 1-3 fluoro, and —$OCH_3$, and
(g) —CN.

An embodiment of the present invention includes compounds wherein $R^1$ is selected from:
(a) hydrogen,
(b) $C_{1-6}$alkyl, which is unsubstituted or substituted with cyclopropyl which is unsubstituted or substituted with substituents selected from: fluoro and $C_{1-6}$ alkyl,
(c) dihydrofuropyridinyl,
(d) indazole, which is unsubstituted or substituted with $C_{1-3}$alkyl,
(e) tetrahydroisobenzofuranyl, which is unsubstituted or substituted with $C_{1-3}$alkyl,
(f) phenyl, which is unsubstituted or substituted with $C_{1-3}$alkyl or —CN, and
(g) pyridyl, which is unsubstituted or substituted with $C_{1-3}$alkyl or —O—$C_{1-3}$alkyl.

An embodiment of the present invention includes compounds wherein $R^1$ is selected from:
(a) $C_{1-6}$alkyl, which is unsubstituted or substituted with cyclopropyl, methyl-cyclopropyl, dimethyl-cyclopropyl, methyl-fluoro-cyclopropyl, methyl-difluoro-cyclopropyl, or dimethyl-difluoro-cyclopropyl,
(b) indazole, which is unsubstituted or substituted with $C_{1-3}$alkyl,
(c) tetrahydroisobenzofuranyl, which is unsubstituted or substituted with $C_{1-3}$ alkyl,
(d) phenyl, which is unsubstituted or substituted with $C_{1-3}$alkyl or —CN, and
(e) pyridyl, which is unsubstituted or substituted with $C_{1-3}$alkyl or —O—$C_{1-3}$alkyl.

An embodiment of the present invention includes compounds wherein $R^1$ is phenyl, which is unsubstituted or substituted with —CN. An embodiment of the present invention includes compounds wherein $R^1$ is pyridyl, which is unsubstituted or substituted with —$OCH_3$. An embodiment of the present invention includes compounds wherein $R^1$ is dihydrofuropyridinyl. An embodiment of the present invention includes compounds wherein $R^1$ is indazole, which is unsubstituted or substituted with methyl. An embodiment of the present invention includes compounds wherein $R^1$ is tetrahydroisobenzofuranyl. An embodiment of the present invention includes compounds wherein $R^1$ is dihydroisobenzofuranyl. An embodiment of the present invention includes compounds wherein $R^1$ is —$CH_2$-(methyl)cyclopropyl. An embodiment of the present invention includes compounds wherein $R^1$ is —$CH_2$-(dimethyl)-cyclopropyl. An embodiment of the present invention includes compounds wherein $R^1$ is —$CH_2$-(methyl-fluoro)cyclopropyl. An embodiment of the present invention includes compounds wherein $R^1$ is —$CH_2$-(methyl-difluoro)cyclopropyl. An embodiment of the present invention includes compounds wherein $R^1$ is —$CH_2$-(dimethyl-difluoro)cyclopropyl.

An embodiment of the present invention includes compounds wherein $R^2$ and $R^3$ are each hydrogen. An embodiment of the present invention includes compounds wherein $R^2$ is fluoro and $R^3$ is hydrogen. An embodiment of the present invention includes compounds wherein $R^2$ is —$CH_3$ and $R^3$ is hydrogen. An embodiment of the present invention includes compounds wherein $R^2$ is fluoro and $R^3$ is fluoro.

An embodiment of the present invention includes compounds wherein $R^4$ is hydrogen.

An embodiment of the present invention includes compounds wherein $R^7$ is selected from:
(1) hydrogen,
(2) methyl,
(3) ethyl,
(4) —CH$_2$OH,
(5) —CH$_2$F,
(6) —CHF$_2$,
(7) —CF$_3$,
(8) —CH=CH$_2$,
(9) cyclopropyl,
(10) -fluoro,
(11) -chloro,
(12) -bromo,
(13) —CN,
(14) —(C=O)H, and
(15) —(C=O)O—C$_{1-6}$ alkyl.

An embodiment of the present invention includes compounds wherein $R^7$ is —CH$_3$. An embodiment of the present invention includes compounds wherein $R^7$ is —CH$_2$CH$_3$. An embodiment of the present invention includes compounds wherein $R^7$ is —CF$_3$.

An embodiment of the present invention includes compounds wherein $R^8$ is selected from:
(1) hydrogen,
(2) methyl,
(3) ethyl,
(4) —CH$_2$OH,
(5) —CH$_2$F,
(6) —CHF$_2$,
(7) —CF$_3$, and
(8) —(C=O)O—C$_{1-6}$alkyl.

An embodiment of the present invention includes compounds wherein $R^8$ is hydrogen. An embodiment of the present invention includes compounds wherein $R^8$ is —CH$_3$.

An embodiment of the present invention includes compounds wherein $R^9$ is selected from:
(1) hydrogen, and
(2) —C$_{1-6}$alkyl, which is unsubstituted or substituted with hydroxy, methoxy, 1-3 fluoro.

An embodiment of the present invention includes compounds wherein $R^9$ is hydrogen. An embodiment of the present invention includes compounds wherein $R^9$ is methyl. An embodiment of the present invention includes compounds wherein $R^9$ is —CH$_2$CH$_2$OH.

An embodiment of the present invention includes compounds wherein $R^9$ and $R^{10}$ taken together form a piperidine ring, which is unsubstituted or substituted with substituents selected from: hydroxyl and methyl.

An embodiment of the present invention includes compounds wherein $R^{10}$ is hydrogen and $R^{11}$ is hydrogen. An embodiment of the present invention includes compounds wherein $R^{10}$ is —CH$_3$ and $R^{11}$ is hydrogen. An embodiment of the present invention includes compounds wherein $R^{10}$ is —CH$_3$ and $R^{11}$ is —CH$_3$. An embodiment of the present invention includes compounds wherein $R^{10}$ is —CH$_2$OH and $R^{11}$ is hydrogen. An embodiment of the present invention includes compounds wherein $R^{10}$ and $R^{11}$ taken together form a cyclopropyl group. An embodiment of the present invention includes compounds wherein $R^{10}$ and $R^{11}$ taken together form a =CH$_2$ group. An embodiment of the present invention includes compounds wherein $R^{10}$ and $R^{11}$ taken together form a keto group.

Certain embodiments of the present invention include a compound which is selected from the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Likewise, —N(C$_{3-6}$cycloalkyl) refers to the presence of a nitrogen-containing saturated such a pyrrolidine or piperidine. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The term "heteroaryl" as used herein represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocyclyl below, "heteroaryl" is also understood to include the N-oxide derivative of any nitrogen-containing heteroaryl. In cases where the heteroaryl substituent is bicyclic and one ring is non-aromatic, in one embodiment, the attachment is via a carbon atom of the aromatic ring. Examples of heteroaryl include but are not limited to benzodioxolyl, benzofuranyl, benzofurazanyl, benzoimidazolyl, benzimidazolonyl, benzopyrazolyl, benzothiazolyl, benzotriazolyl, benzothiophenyl, benzoxazepinyl, benzooxazinonyl, benzooxazolonyl, benzoxazolyl, carbazolyl, carbolinyl, chromanyl, cinnolinyl, cyclopentapyridinyl, dihydrobenzo[1,4]dioxinyl, dihydrobenzofuranyl, dihydrobenzo[1,4]oxazinyl, dihydrofuropyridinyl, dihydroindolyl, dihydroisobenzofuranyl, dihydroisoquinolinonyl, dihydropyranopyridinyl, dihydroimidazopyridinyl, dihydropyrido[1,4]oxazinyl, dihydroquinolinone, furanyl, imidazolyl, indolinyl, indolyl, indanyl, indolazinyl, indazolyl, isobenzofuranyl, isobenzofuranonyl, isochromanonyl, isochromanyl, isoindolinyl, isoindolyl, isoxazolinyl, isoxazolyl, isoquinolyl, isothiazolyl, isoxazolyl, naphthpyridinyl, oxadiazolyl, oxazolyl, oxazolinyl, oxetanyl, oxoisoindolinyl, pyrazinyl, pyrazolopyridinyl, pyrazolyl, pyridazinyl, pyridopyridinyl, pyridazinyl, pyridyl, pyrimidinyl, pyrimidyl, pyrrolopyridinyl, pyrrolyl, quinazolinyl, quinolyl, quinoxalinyl, tetrahydrobenzooxepinyl, tetrahydroisoquinolinyl, tetrahydropyranyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. In one embodiment, the heterocyclyls contain about 5 to about 6 ring atoms. The heterocyclyl may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydropyran, tetrahydrothiophenyl, lactam, lactone, and the like. "Heterocyclyl" also includes heterocyclyl rings as described above wherein =O replaces two available hydrogens on the same ring carbon atom.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes that can be incorporated into the compounds of the invention include isotopes of hydrogen such as $^{2}$H and $^{3}$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}$H) and deuterium ($^{2}$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, Life Sciences, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 15000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 µM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, *cannabis*, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia;

hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDKS inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3β inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NM antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; aq: aqueous; BINAP: 2,2'-bis(diphenylphosphino)-1,1'-binaphthyl; Bn: benzyl; Ac: acetyl; Boc: tert-butyloxy carbonyl; BSA: bovine serum albumin; CAN: acetonitrile; Cbz: carboxylbenzyl; CbzCl: benzylchloroformate; CDI: carbonyl diimidazole; DAST: diethylaminosulfur trifluoride; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMS: dimethylsulfide; DMSO: dimethylsulfoxide; dppf: 1,1'-bis(diphenyl-phosphino)ferrocene; CH2Cl2: dichloromethane; EDC: N-(3-

Dimethylaminopropyl)-N'-ethylcarbodiimide; Et3N: triethylamine; EtOAc: ethyl acetate; EtOH: ethanol; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; LHMDS: lithium bis(trimethylsilyl)amide; mCPBA: meta-chloroperbenzoic acid; MeOH: methanol; MgSO4: magnesium sulfate; Ms: methanesulfonyl; MTBE: methyl tert-butyl ether; MS: Mass spectra; NaHCO3: sodium bicarbonate; NaOH: sodium hydroxide; NBS: N-bromosuccinimide; NCS: N-chlorosuccinimide; NMM: N-methylmorpholine; NMR: nuclear magnetic resonance; PtO2: platinum oxide; PyClu: 1-(chloro-1-pyrrolidinylmethylene)-pyrrolidinium hexafluorophosphate; rt: room temperature; SEM: 2-(Trimethylsilyl)ethoxy]methyl; SFC: supercritical fluid chromatography; SOCl2: thionyl chloride; T3P: 2,4,6-tripropyl-1,3,5,2,4,6-trioxatriphosphorinane-2,4,6-trioxide; TBAF: tetra-n-butylammonium fluoride; TBS: tert-Butyldimethylsilyl; TEA: triethylamine; TES: Triethylsilyl; TFA: trifluoroacetic acid; Tf: triflate; TFAA: trifluoroacetic anhydride; THF: tetrahydrofuran; TIPS: tri-isopropylsilyl; TLC: thin layer chromatography; Ts: toluenesulfonyl; X-Phos: 2-(dicyclohexyl-phosphino)-2',4',6'-triisopropyl-biphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

SCHEME A

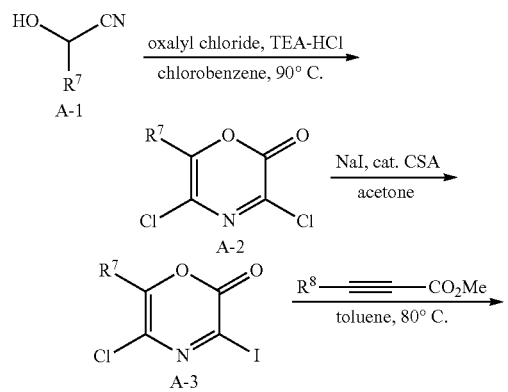

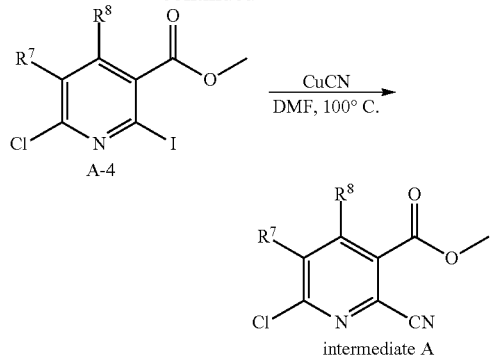

Intermediate A is prepared according to Scheme A via condensation of commercially available hydroxynitrile A-1 with oxalyl chloride to yield adduct A-2. A Finkelstein reaction of chloride A-2 with sodium iodide, catalyzed by camphorsulfonic acid (CSA), results in iodide product A-3. A hetero-Diels-Alder reaction of diene A-3 with a commercially available ynone gives pyridine A-4. A subsequent copper-meditated cyanation provides intermediate A.

Intermediate A1

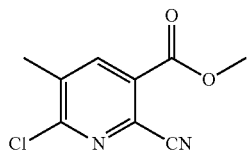

Methyl 6-chloro-2-cyano-5-methylnicotinate
(Scheme A)

Step 1: 3,5-Dichloro-6-methyl-2H-1,4-oxazin-2-one

Into a 10-L 4-necked round-bottom flask was charged oxalic dichloride (3.32 kg, 26.2 mol) and chlorobenzene (3.5 L) under an inert atmosphere of nitrogen. A solution of 2-hydroxypropanenitrile (464.8 g, 6.54 mol) in chlorobenzene (500 mL) was added dropwise to the flask at 0° C. The system was heated to 90° C. and triethylamine hydrochloride (66.2 g, 481 mmol) was added in portions at 90° C. The resulting solution was stirred for 3 h before concentrating the mixture under reduced pressure. The resulting solution was diluted with ether (5 L) and the solids were filtered out. The filtrate concentrated and was then applied purified by silica gel column chromatography (0:1-1:4 ethyl acetate:petroleum ether) to yield the title compound.

Step 2:
5-Chloro-3-iodo-6-methyl-2H-1,4-oxazin-2-one

Into a 10-L 4-necked round-bottom flask was added 3,5-dichloro-6-methyl-2H-1,4-oxazin-2-one (470.8 g, 2.62 mol), acetone (10 L), NaI (1568 g, 10.5 mol) and camphorsulfonic acid (40 g, 172.2 mmol) under an atmosphere of nitrogen. The resulting solution was stirred for 3 h at 25° C. The mixture was concentrated and then diluted with water (20 L) and dichloromethane (3×5 L). The organic layers were combined and washed with brine (5 L). The mixture was dried over anhydrous sodium sulfate, filtered and was concentrated under reduced pressure to yield the title compound.

Step 3: Methyl 6-chloro-2-iodo-5-methylnicotinate

Into a 5-L 3-necked round-bottom flask was placed 5-chloro-3-iodo-6-methyl-2H-1,4-oxazin-2-one (638 g, 2.35 mol), toluene (2.3 L), and methyl prop-2-ynoate (592.8 g, 7.05 mol) under an atmosphere of nitrogen. The resulting solution was stirred for 2 days at 80° C. The reaction was cooled and the volatiles were removed under reduced pressure. The residue was purified by silica gel column chromatography (0:1-1:50 ethyl acetate:petroleum ether) to provide the major regioisomeric product as the title compound.

Step 4: Methyl 6-chloro-2-cyano-5-methylnicotinate

Into a 20-mL microwave tube was added methyl 6-chloro-2-iodo-5-methylpyridine-3-carboxylate (2 g, 6.42 mmol), DMF (15 mL), and CuCN (850 mg, 9.60 mmol). The resulting solution was stirred for 5 min at 100° C. by microwave irradiation. The mixture was diluted with water (20 mL) and a saturated, aqueous solution of $NH_4Cl$ (100 mL). Dichloromethane (2×20 mL) was used to extract the crude material and the organic layers were combined and dried over anhydrous sodium sulfate. The residue was purified by silica gel chromatography (0:1-1:8 ethyl acetate:petroleum ether) to provide the title compound. MS: 211 (M+1). $^1$H NMR (500 MHz, $CDCl_3$): δ 7.87 (s, 1H), 3.95 (s, 4H), 2.37 (s, 3H).

The following intermediates in table A were prepared according to scheme A using the procedure outlined in the synthesis of intermediate A1 using commercially available hydroxynitriles in step 1 and using commercially available ynones for step 3.

TABLE A

| Intermediate | Structure | Name | MS (M + 1) |
|---|---|---|---|
| A2 | 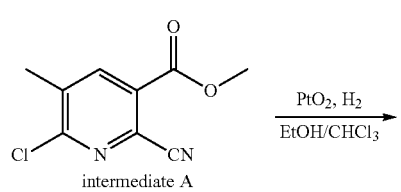 | methyl 6-chloro-2-cyano-4,5-dimethylnicotinate | 225 |
| A3 | 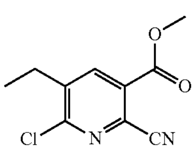 | methyl 6-chloro-2-cyano-5-ethylnicotinate | 225 |

SCHEME B

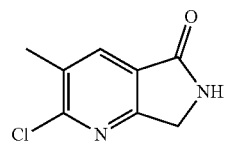

intermediate A

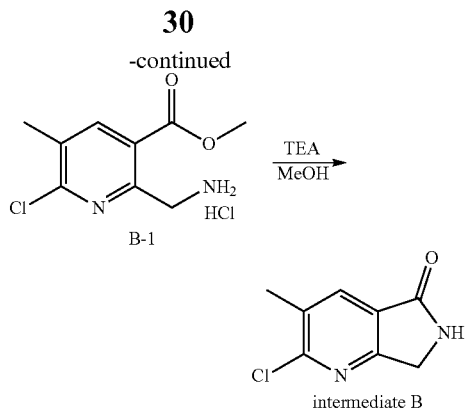

intermediate B

Intermediate B is prepared according to Scheme B in a two-step process from intermediate A via a platinum-mediated nitrile reduction and subsequent base-mediated cyclization of amine B-1.

Intermediate B1

2-Chloro-3-methyl-6,7-dihydro-5H-pyrrolo[3,4-b]pyridin-5-one (Scheme B)

Step 1: Methyl 2-(aminomethyl)-6-chloro-5-methylnicotinate hydrochloride

Into a 5-L 2-necked round-bottom flask was placed methyl 6-chloro-2-cyano-5-methylpyridine-3-carboxylate (intermediate A1, 82 g, 389.3 mmol), 3:1 ethanol:chloroform (2.5 L) and $PtO_2$ (15 g). The resulting solution was stirred for 36 h at RT under an atmosphere of hydrogen. The solids were removed by filtration and the filtrate was concentrated under reduced pressure to yield the title compound.

Step 2: 2-Chloro-3-methyl-6,7-dihydro-5H-pyrrolo[3,4-b]pyridin-5-one

Into a 10-L 4-necked round-bottom flask purged and maintained with an inert atmosphere of nitrogen, was placed methyl 2-(aminomethyl)-6-chloro-5-methylpyridine-3-carboxylate hydrochloride (110 g, 438.06 mmol), methanol (6 L), TEA (221.6 g, 2.19 mol). The resulting solution was stirred for 12 h at RT. The solids were removed by filtration and the filtrate was concentrated under reduced pressure to yield the crude product. Addition of hot DCM eventually resulted in the formation of a precipitate which was isolated by filtration to yield the title compound. MS: 183 (M+1). $^1$H NMR (500 MHz, $CDCl_3$): δ 2.45 (s, 3H), 4.39 (s, 2H), 8.11 (s, 1H), 8.82 (s, 1H).

The following intermediates in table B were prepared according to scheme B using the procedure outlined in the synthesis of intermediate B1.

TABLE B

| Intermediate | Structure | Name | MS (M + 1) |
|---|---|---|---|
| B2 | 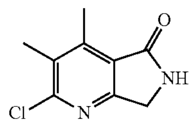 | 2-chloro-3,4-dimethyl-6,7-dihydro-5H-pyrrolo[3,4-b]pyridin-5-one | 197 |
| B3 | 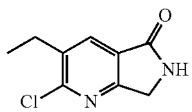 | 2-chloro-3-ethyl-6,7-dihydro-5H-pyrrolo[3,4-b]pyridin-5-one | 197 |

SCHEME C

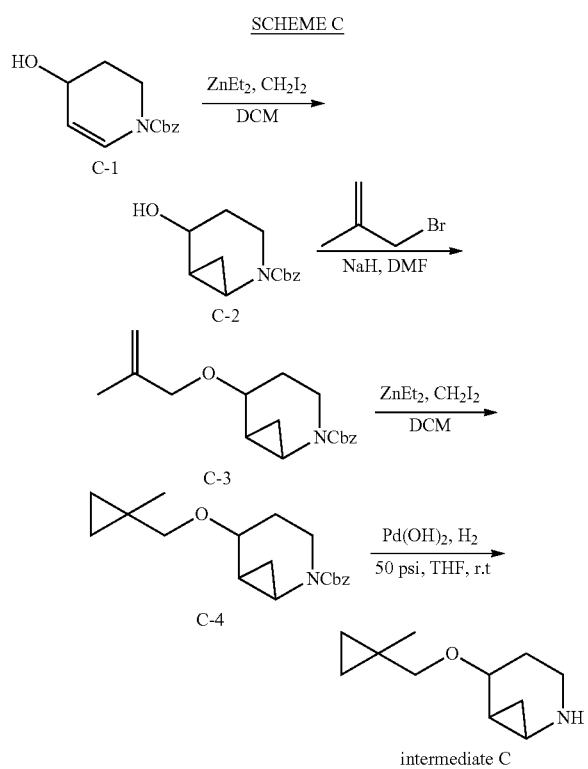

Intermediate C

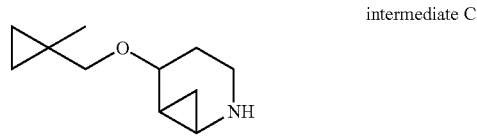

Step 1: benzyl 5-hydroxy-2-azabicyclo[4.1.0]heptane-2-carboxylate

To a solution of benzyl 4-hydroxy-3,4-dihydropyridine-1(2H)-carboxylate (6.5 g, 27.9 mmol)) in dichloromethane (70 mL) was added diethylzinc (69.7 ml, 69.7 mmol) followed by dropwise addition of diiodomethane (8.99 mL, 111 mmol) in dichloromethane (10 mL). The resulting mixture was stirred at 20° C. for 16 h. 1 N HCl (20 mL) was added dropwise and the mixture was extracted with ethyl acetate (100 mL×4). The combined organic layers were washed with saturated aqueous NaHCO$_3$ solution (50 mL×2), followed by water (15 mL×2), dried over sodium sulfate, filtered and the filtrate was concentrated in vacuo. The residue was purified by combiflash (SiO$_2$, petroleum ether:ethyl acetate from 10:1 to 1:1) to provide the title compound. MS 248.1 (M+1). $^1$H NMR (400 MHz, CDCl$_3$): δ 7.30-7.39 (5H, m), 5.10-5.22 (2H, m), 4.28-4.33 (1H, 1H), 3.74-3.94 (1H, m), 3.1.-3.17 (1H, m), 2.72-2.80 (1H, m), 1.85-1.95 (1H, m), 1.70 (1H, t, J=6.0 Hz), 1.47-1.62 (1H, m), 1.20-1.23 (1H, m), 0.80-0.95 (1H, m), 0.61-0.63 (1H, m).

Step 2: benzyl 5-((2-methylallyl)oxy)-2-azabicyclo[4.1.0]heptane-2-carboxylate To a solution of benzyl 5-hydroxy-2-azabicyclo[4.1.0]heptane-2-carboxylate (4.88 g, 19.73 mmol) in DMF (30 mL) was added NaH (1.579 g, 39.5 mmol, 60% w) at 0° C. and the mixture was stirred at 0° C. for 30 mins. Then a solution of 3-bromo-2-methylprop-1-ene (4.00 g, 29.6 mmol) in DMF (10 mL) was added dropwise to the mixture and the resulting mixture was warmed to 45° C. with stirring under N$_2$ atmosphere for 3 h. The reaction mixture was quenched with NH$_4$Cl (20 mL). Then the mixture was extracted with EtOAc (50 mL×3), the combined organic layers were washed with brine (25 mL×3), dried over anhydrous sodium sulfate, filtered and the filtrate was concentrated in vacuo. The residue was purified by column chromatography (SiO$_2$, petroleum ether:ethyl acetate from 20:1 to 5:1) to provide the title compound. MS: 302.1 (M+1). $^1$H NMR (400 MHz, CDCl$_3$): δ 7.30-7.41 (5H, m), 5.12-5.20 (2H, m), 5.00 (1H, s), 4.92 (1H, s), 3.90-4.07 (3H, m), 3.70-3.89 (1H, m), 3.00-3.15 (1H, m), 2.71-2.77 (1H, m), 1.80-1.90 (1H, m), 1.78 (3H, s), 1.49-1.55 (1H, m), 1.26-1.32 (1H, m), 0.80-1.01 (1H, m), 0.68-0.69 (1H, m).

Step 3: Benzyl 5-((1-methylcyclopropyl)methoxy)-2-azabicyclo[4.1.0]heptane-2-carboxylate To a solution of benzyl 5-((2-methylallyl)oxy)-2-azabicyclo[4.1.0]heptane-2-carboxylate (4.6 g, 15.26 mmol) in dichloromethane (50 mL) was added diethylzinc (45.8 mL, 45.8 mmol) at 0° C. and stirred for 30 min. Then a solution of diiodomethane (6.16 mL, 76 mmol) in dichloromethane (10 mL) was added dropwise to the mixture. The resulting mixture was stirred at 20° C. for 3 h under N$_2$ atmosphere. The reaction mixture was quenched with 1 N HCl (20 mL). Then the mixture was extracted with dichloromethane (100 mL×3). The combined organic layers were washed with brine (20 mL), dried over anhydrous sodium sulfate, filtered and the filtrate was concentrated in vacuo. The residue was purified by column chromatography (SiO$_2$, petroleum ether:ethyl acetate from 15:1 to 5:1) to provide the title compound. MS: 316.1 (M+1). $^1$H NMR (400 MHz, CDCl$_3$): δ 7.33-7.38 (5H, m), 5.11-5.23 (2H, m), 3.70-4.02 (2H, m), 3.41 (1H, t, J=8.4 Hz), 3.28 (1H, t, J=6.4 Hz), 3.06-3.19 (1H, m), 2.73-2.90 (1H, m), 1.75-1.95 (1H, m), 1.40-1.55 (1H, m), 1.25-1.35 (1H, m), 1.15 (3H, s), 0.88-1.00 (1H, m), 0.66-0.68 (1H, m), 0.40-0.42 (2H, m), 0.34-0.36 (2H, m).

Step 4: Benzyl 5-((1-methylcyclopropyl)methoxy)-2-azabicyclo[4.1.0]heptane-2-carboxylate A mixture of benzyl 5-((1-methylcyclopropyl)methoxy)-2-azabicyclo[4.1.0]-heptane-2-carboxylate (3.5 g, 11.10 mmol) and Pd(OH)$_2$/C (0.779 g, 1.110 mmol) in THF (100 mL) was stirred at 15° C. under 15 psi of H$_2$ atmosphere for 45 min. The mixture was filtered and the filtrate was concentrated in vacuo to provide the title compound. MS: 182.2 (M+1).

SCHEME D

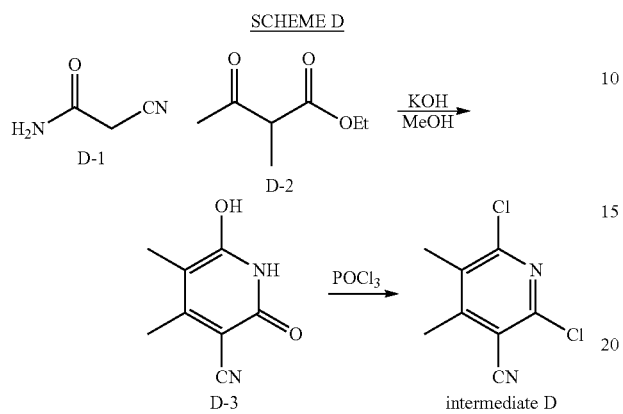

As shown in Scheme D, intermediate D is synthesized beginning from a condensation of 2-cyanoacetamide and β-keto ester D-2 to form pyridone D-3. Reaction with phosphoryl chloride provides intermediate D.

INTERMEDIATED D

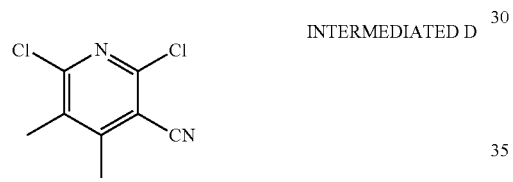

2,6-Dichloro-4,5-dimethylpyridine-3-carbonitrile (Scheme D)

Step 1: 6-Hydroxy-4,5-dimethyl-2-oxo-1,2-dihydro-pyridine-3-carbonitrile

To a solution of 2-cyanoacetamide (100 g, 1.2 mol) was dissolved in MeOH (1.5 L), was added ethyl 2-methyl-3-oxobutanoate (171 g, 1.2 mol) and potassium hydroxide (100 g, 1.8 mol). The resulting solution was stirred for 4 h at 65° C. before being cooled to 10° C. The solids were collected by filtration and were dissolved in 2 L of hot water (70° C.). The mixture was filtered and the filtrate was was adjusted to pH-1 with aqueous hydrogen chloride (6 N). The solids were collected by filtration to yield the title compound.

Step 2: 2,6-Dichloro-4,5-dimethylpyridine-3-carbonitrile

To phosphoroyl trichloride (126 mL) was added 2,6-dihydroxy-4,5-dimethylpyridine-3-carbonitrile (70 g, 426.41 mmol) in several batches. The system was sealed and the resulting solution was stirred for 6 h at 180° C. The reaction was cooled to RT and the mixture was poured into ice water (500 mL). The solids were collected by filtration to afford the title compound.

The compounds of the present invention may be prepared according to the schemes and procedures described herein.

SCHEME 1

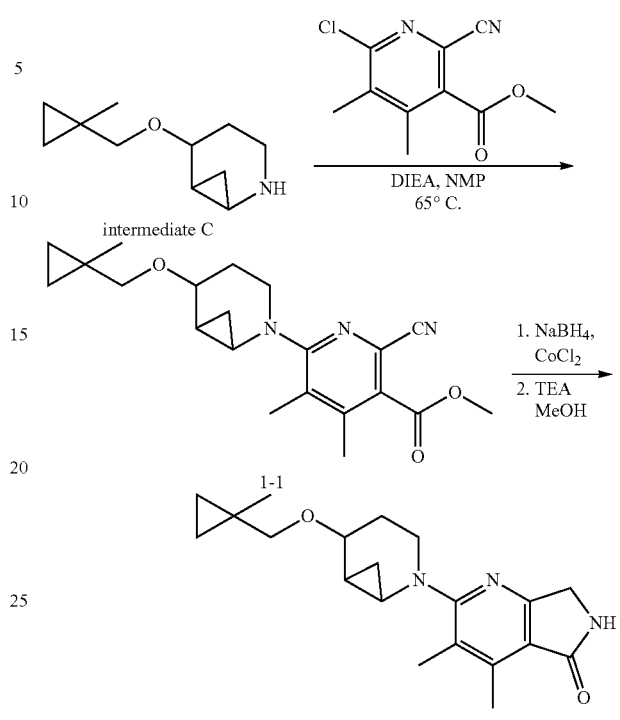

Example 1 & Example 2

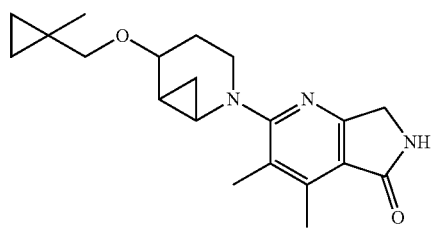 [SMILES: Cc1c(N2CCC(OCC3(C)CC3)C3CC32)nc2c(c1C)C(=O)NC2]

3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Scheme 1)

Step 1: Methyl 2-cyano-4,5-dimethyl-6-(5-((1-methylcyclopropyl)methoxy)-2-azabicyclo[4.1.0]heptan-2-yl)nicotinate To a solution of 5-((1-methylcyclopropyl)methoxy)-2-azabicyclo[4.1.0]heptane (intermediate C, 1695 mg, 9.35 mmol) and methyl 6-chloro-2-cyano-4,5-dimethylnicotinate (intermediate A2, 700 mg, 3.12 mmol) in NMP (30 mL) was added DIEA (1.633 mL, 9.35 mmol) and the resulting mixture was heated to 65° C. with stirring under N$_2$ atmosphere for 16 h. The mixture was diluted with water (50 mL) and extracted with ethyl acetate (100 mL×3). The combined organic layers were washed with brine (30 mL×3), dried over sodium sulfate, filtered and the filtrate was concentrated in vacuo. The residue was purified by combiflash (SiO$_2$, petroleum ether:ethyl acetate from 10:1 to 3:1) to provide the title compound. MS: 370.0 (M+1). ¹H NMR (400 MHz, CDCl₃): δ 4.04-4.07 (1H, m), 3.97 (3H, s), 3.78-3.82 (1H, m), 3.38-3.40 (1H, m), 3.29-3.31 (1H, m), 2.84-2.91 (2H, m), 2.36 (6H, s), 1.95-2.08 (1H, m), 1.50-1.56 (1H, m), 1.40-1.44 (1H, m), 1.14 (3H, s), 0.90-0.94 (1H, m), 0.61-0.63 (1H, m), 0.40-0.45 (2H, m), 0.33-0.36 (2H, m).

Step 2: 3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of methyl 2-cyano-4,5-dimethyl-6-(5-((1-methylcyclopropyl)-methoxy)-2-azabicyclo[4.1.0]heptan-2-yl)nicotinate (Step 1 product, 480 mg, 1.299 mmol) and cobalt(ii) chloride (506 mg, 3.90 mmol) in MeOH (15 mL) was added NaBH₄ (295 mg, 7.80 mmol) and resulting mixture was stirred at 20° C. under N₂ atmosphere for 3 h. The mixture was diluted with water (30 mL) and extracted with ethyl acetate (100 mL×3). The combined organic layers were dried over sodium sulfate, filtered and the filtrate was concentrated in vacuo. To the residue was added TEA (0.362 mL, 2.60 mmol) and methanol (15 mL) and the mixture was stirred at 40° C. for 1 h. The mixture was concentrated in vacuo. The residue was purified by prep-TLC (petroleum ether:ethyl acetate 1:1) to provide the title compound. The title compound (25 mg, 0.073 mmol) was separated by chiral SFC (AD(250 mm*30 mm, 5 um), 40% MeOH with 0.1% NH₃H₂O/CO₂ at 60 mL/min) and Prep-HPLC (TFA) to give two isomers, both as pale white solid.

Example 1: MS: 342.2 (M+1). ¹H NMR (400 MHz, Methanol-d₄): δ 7.14 (1H, brs), 4.29-4.40 (2H, m), 4.06-4.09 (1H, m), 3.73-3.76 (1H, m), 3.41-3.44 (1H, m), 3.30-3.33 (1H, m), 3.05-3.13 (1H, m), 2.88-2.91 (1H, m), 2.64 (3H, s), 2.37 (3H, s), 2.02-2.10 (1H, m), 1.60-1.63 (1H, m), 1.40-1.55 (1H, m), 1.16 (3H, s), 0.95-1.01 (1H, m), 0.72-0.76 (1H, m), 0.42-0.44 (2H, m), 0.33-0.36 (2H, m). Example 2: MS: 342.2 (M+1). ¹H NMR (400 MHz, Methanol-d₄): δ 7.07 (1H, brs), 4.28-4.39 (2H, m), 4.06-4.09 (1H, m), 3.73-3.76 (1H, m), 3.41-3.44 (1H, m), 3.30-3.33 (1H, m), 3.05-3.13 (1H, m), 2.88-2.91 (1H, m), 2.64 (3H, s), 2.37 (3H, s), 2.02-2.10 (1H, m), 1.60-1.63 (1H, m), 1.40-1.55 (1H, m), 1.16 (3H, s), 0.95-1.01 (1H, m), 0.72-0.76 (1H, m), 0.42-0.44 (2H, m), 0.33-0.36 (2H, m).

The following examples in Table 1 were prepared according to scheme 1 using the procedure outlined in the synthesis of Example 1 and Example 2 and using intermediate A1 in Step 1.

TABLE 1

| Ex | Structure | Name | MS (M + 1) | ¹H NMR |
|---|---|---|---|---|
| 3 | 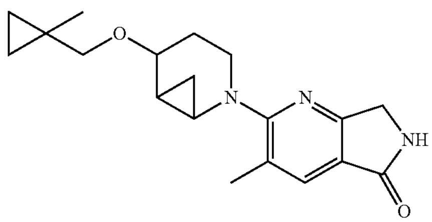 [SMILES: Cc1cc2c(nc1N1CCC(OCC3(C)CC3)C3CC31)CNC2=O] | 3-methyl-2-(5-((1-methylcyclopropyl)methoxy)-2-azabicyclo[4.1.0]heptan-2-yl)-6,7-dihydro-5H-pyrrolo[3,4-b]pyridin-5-one | 328.1 | (400 MHz, CDCl₃): δ 7.72 (1 H, s), 6.57 (1 H, s), 4.30 (2 H, s), 4.08-4.29 (1 H, m), 3.93-3.97 (1 H, m), 3.42 (1 H, d, J = 9.6 Hz), 3.30 (1 H, d, J = 6.4 Hz), 3.00-3.02 (1 H, m), 2.92 (1H, t, J = 7.2 Hz), 2.48 (3 H, s), 1.98-2.01 (1 H, m), 1.60-1.63 (1 H, m), 1.39-1.44 (1 H, m), 1.15 (3 H, s), 0.93-0.95 (1 H, m), 0.67-0.69 (1 H, m), 0.40-0.42 (2 H, m), 0.34-0.37 (2 H, m) |
| 4 | 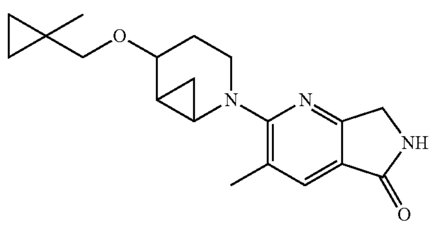 [SMILES: Cc1cc2c(nc1N1CCC(OCC3(C)CC3)C3CC31)CNC2=O] | 3-methyl-2-(5-((1-methylcyclopropyl)methoxy)-2-azabicyclo[4.1.0]heptan-2-yl)-6,7-dihydro-5H-pyrrolo[3,4-b]pyridin-5-one | 328.1 | (400 MHz, CDCl₃): δ 7.72 (1 H, s), 6.38 (1 H, s), 4.31 (2 H, s), 4.07-4.30 (1 H, m), 3.94-3.97 (1 H, m), 3.42 (1 H, d, J = 9.6 Hz), 3.30 (1 H, d, J = 6.4 Hz), 3.00-3.02 (1 H, m), 2.93 (1 H, t, J = 7.2 Hz), 2.49 (3 H, s), 1.98-2.01 (1 H, m), 1.60-1.63 (1 H, m), 1.45-1.48 (1 H, m), 1.15 (3 H, s), 0.93-0.95 (1 H, m), 0.67-0.69 (1 H, m), 0.41-0.43 (2 H, m), 0.33-0.36 (2 H, m) |

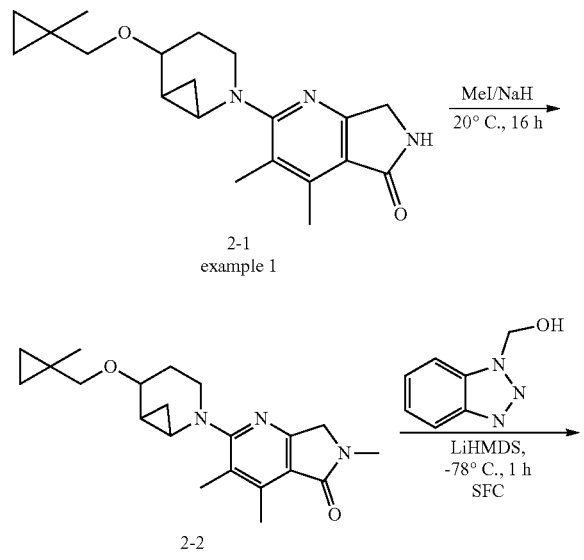

SCHEME 2

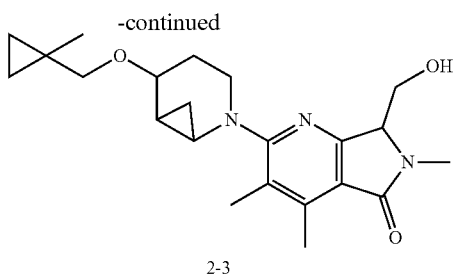

2-3

Example 5, 6, 7 & 8

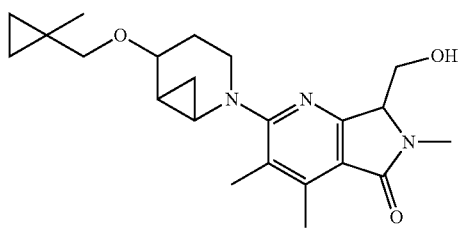 [SMILES: Cc1c(N2CCC(OCC3(C)CC3)C3CC32)nc2c(c1C)C(=O)N(C)C2CO]

7-(hydroxymethyl)-3,4,6-trimethyl-2-(5-((1-methyl-cyclopropyl)methoxy)-2-azabicyclo[4.1.0]heptan-2-yl)-6,7-dihydro-5H-pyrrolo[3,4-b]pyridin-5-one (Scheme 2)

Step 1: 3,4,6-trimethyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of compound 3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Example 1 compound, 132 mg, 0.309 mmol) in DMF (3 mL) was added NaH (13.61 mg, 0.340 mmol, 60% w) and the mixture was stirred at 0° C. for 30 min. Then MeI (0.023 mL, 0.371 mmol) was added and the mixture was stirred at 15° C. for 3 h. The reaction mixture was quenched with saturated NH4Cl aqueous (2 mL), followed by water (8 mL), then the mixture was extracted with EtOAc (10 mL×3). The combined organic layers were washed with brine, dried over anhydrous sodium sulfate, filtered and concentrated to get the residue, which was further purified by prep-TLC (Petrolem.ether:EtOAc=1:2) to provide the title compound. MS: 356.2 (M+1).

Step 2: 7-(hydroxymethyl)-3,4,6-trimethyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of 3,4,6-trimethyl-2-(5-((1-methylcyclopropyl)methoxy)-2-azabicyclo[4.1.0]heptan-2-yl)-6,7-dihydro-5H-pyrrolo[3,4-b]pyridin-5-one (77 mg, 0.217 mmol) in THF (1 mL) was added LiHMDS (1.083 ml, 1.083 mmol) at −78° C. Then the mixture was stirred at −78° C. for 30 min. Then (1H-benzo[d][1,2,3]triazol-1-yl)methanol (48.5 mg, 0.325 mmol) in THF (1 mL) was dropwise added to the mixture and the mixture was stirred for another 30 min. The reaction mixture was diluted with water (10 mL) and extracted with EtOAc (10 mL×2). The combined organic layers were dried over Na2SO4 and filtered, and the filtrate was concentrated in vacuo to give the residue, which was further purified by prep-TLC (dichloromethane:MeOH=10:1) to provide the title compound as yellow oil. The title compound was separated by chiral SFC (AD(250 mm*30 mm, 10 um), 30% MeOH with 0.1% NH3.H2O/CO2 at 60 mL/min) and Prep-HPLC (TFA) to give four isomers. Example 5 (first peak): MS: 386.1 (M+1). $^1$H NMR (400 MHz, Methanol-$d_4$): δ 4.23-4.25 (1H, m), 4.11-4.14 (2H, m), 3.97-3.99 (1H, m), 3.79-3.82 (1H, m), 3.46-3.49 (1H, m), 3.33-3.35 (1H, m), 3.13 (3H, s), 2.94-3.01 (2H, m), 2.60 (3H, s), 2.36 (3H, s), 1.95-2.01 (1H, m), 1.46-1.70 (2H, m), 1.14 (3H, s), 0.87-0.92 (1H, m), 0.58-0.61 (1H, m), 0.42-0.45 (2H, m), 0.30-0.32 (2H, m). Example 6 (second peak): MS: 386.2 (M+1). $^1$H NMR (400 MHz, Methanol-$d_4$): δ 4.23-4.25 (1H, m), 4.11-4.14 (2H, m), 4.01-4.04 (1H, m), 3.79-3.82 (1H, m), 3.46-3.49 (1H, m), 3.32-3.35 (1H, m), 3.13 (3H, s), 2.94-3.01 (2H, m), 2.60 (3H, s), 2.36 (3H, s), 1.95-2.01 (1H, m), 1.46-1.70 (2H, m), 1.14 (3H, s), 0.87-0.92 (1H, m), 0.58-0.61 (1H, m), 0.42-0.45 (2H, m), 0.30-0.32 (2H, m). Example 7 (third peak): MS: 386.1 (M+1). $^1$H NMR (400 MHz, Methanol-$d_4$): δ 4.23-4.25 (1H, m), 4.11-4.14 (2H, m), 4.01-4.02 (1H, m), 3.79-3.82 (1H, m), 3.45-3.47 (1H, m), 3.32-3.35 (1H, m), 3.13 (3H, s), 2.94-3.01 (2H, m), 2.60 (3H, s), 2.36 (3H, s), 1.95-2.01 (1H, m), 1.46-1.70 (2H, m), 1.14 (3H, s), 0.87-0.92 (1H, m), 0.58-0.61 (1H, m), 0.42-0.45 (2H, m), 0.31-0.32 (2H, m). Example 8 (fourth peak): MS: 386.1 (M+1). $^1$H NMR (400 MHz, Methanol-$d_4$): δ 4.23-4.26 (1H, m), 4.11-4.14 (2H, m), 3.98-4.01 (1H, m), 3.79-3.82 (1H, m), 3.45-3.47 (1H, m), 3.32-3.35 (1H, m), 3.13 (3H, s), 2.94-3.01 (2H, m), 2.60 (3H, s), 2.36 (3H, s), 1.95-2.01 (1H, m), 1.46-1.70 (2H, m), 1.14 (3H, s), 0.87-0.92 (1H, m), 0.58-0.61 (1H, m), 0.42-0.44 (2H, m), 0.31-0.32 (2H, m).

SCHEME 3

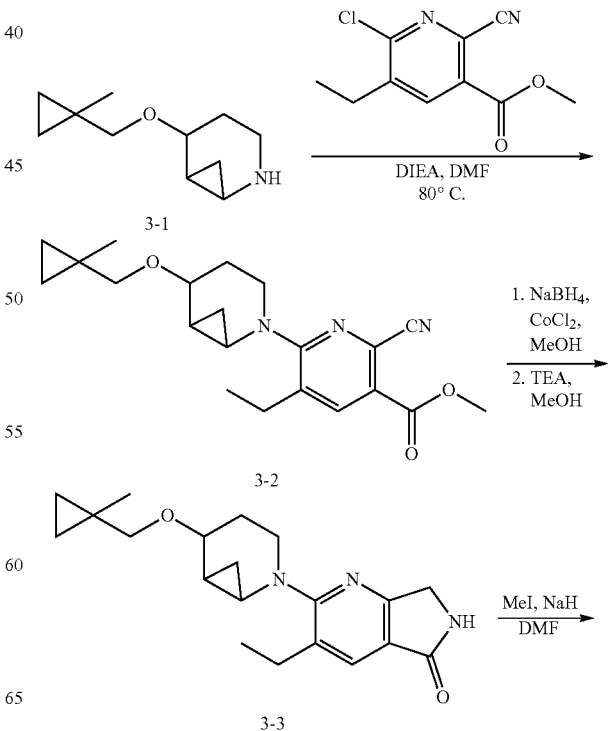

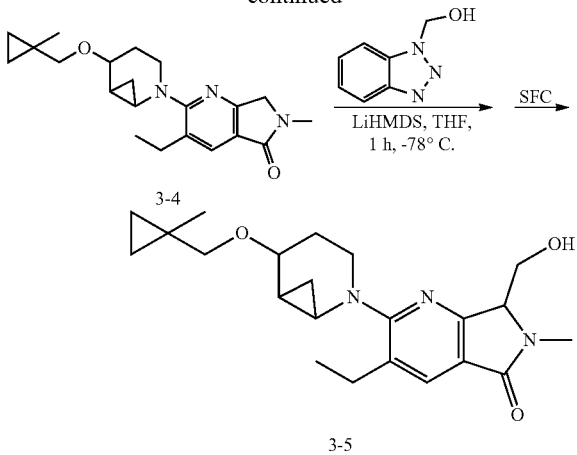

Example 9, 10, 11 & 12

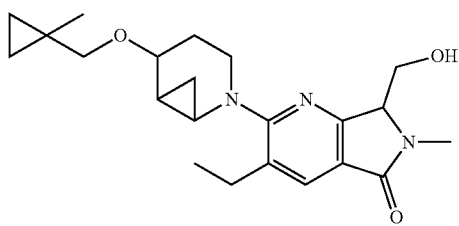 [SMILES: CCc1cc2c(nc1N1CCC(OCC3(C)CC3)C3CC31)C(CO)N(C)C2=O]

3-ethyl-7-(hydroxymethyl)-6-methyl-2-(5-((1-methylcyclopropyl)methoxy)-2-azabicyclo[4.1.0]heptan-2-yl)-6,7-dihydro-5H-pyrrolo[3,4-b]pyridin-5-one
(Scheme 3)

Step 1: Methyl2-cyano-5-ethyl-6-(5-((1-methylcyclopropyl)methoxy)-2-azabicyclo[4.1.0]heptan-2-yl) nicotinate To a solution of 5-((1-methylcyclopropyl)methoxy)-2-azabicyclo[4.1.0]heptane (intermediate C, 261 mg, 1.442 mmol) and methyl 6-chloro-2-cyano-5-ethylnicotinate (intermediate A3, 270 mg, 1.202 mmol) in DMF (8 mL) was added DIEA (0.210 mL, 1.202 mmol). The reaction mixture was stirred at 70° C. for 12 h. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The residue was purified by prep-TLC (SiO$_2$, 25% ethyl acetate in petroleum ether) to give the title compound. MS: 370 (M+1). $^1$H NMR (400 MHz, CDCl$_3$): δ 7.92 (1H, s), 3.70 (3H, s), 3.10 (1H, d, J=9.6 Hz), 2.96 (1H, d, J=9.6 Hz), 2.25-2.60 (6H, m), 1.69-1.72 (1H, m), 1.25-1.35 (2H, m), 0.97-1.01 (3H, m), 0.80 (3H, s), 0.89-0.94 (1H, m), 0.69-0.73 (1H, m), 0.39-0.41 (2H, m), 0.33-0.36 (2H, m).

Step 2: 3-ethyl-2-(5-((1-methylcyclopropyl) methoxy)-2-azabicyclo[4.1.0]heptan-2-yl)-6,7-dihydro-5H-pyrrolo[3,4-b]pyridin-5-one To a solution of methyl 2-cyano-5-ethyl-6-(5-((1-methylcyclopropyl)methoxy)-2-azabicyclo[4.1.0]heptan-2-yl) nicotinate (100 mg, 0.271 mmol) in MeOH (3 mL) were added cobalt(ii) chloride hexahydrate (193 mg, 0.812 mmol) and NaBH$_4$ (51.2 mg, 1.353 mmol). The reaction mixture was stirred at 20° C. for 30 min. Then a solution of TEA (0.038 mL, 0.271 mmol) was added at 20° C. The reaction mixture was stirred at 20° C. for 12 h. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The residue was purified by prep-TLC (SiO$_2$, 50% ethyl acetate in petroleum ether) to give the title compound. MS: 342 (M+1)$^1$H NMR (400 MHz, CDCl$_3$): δ 7.82 (1H, s), 6.16 (1H, s), 4.25 (2H, d, J=4.8 Hz), 4.05-4.12 (1H, m), 3.85-3.90 (1H, m), 3.42 (1H, d, J=9.6 Hz), 3.25 (1H, d, J=9.6 Hz), 2.88-2.98 (4H, m), 2.01-2.05 (1H, m), 1.43-1.57 (1H, m), 1.25 (3H, t, J=7.2 Hz), 1.45 (3H, s), 0.89-0.94 (1H, m), 0.69-0.73 (1H, m), 0.39-0.41 (2H, m), 0.33-0.36 (2H, m)

Step 3: 3-ethyl-6-methyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of 3-ethyl-2-(5-((1-methylcyclopropyl) methoxy)-2-azabicyclo-[4.1.0]heptan-2-yl)-6,7-dihydro-5H-pyrrolo[3,4-b]pyridin-5-one (150 mg, 0.439 mmol) and iodomethane (0.030 ml, 0.483 mmol) in DMF (3 mL) was added NaH (35.1 mg, 0.879 mmol) at 0° C. The reaction mixture was stirred at 0° C. for 30 min. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The residue was purified by prep-TLC (SiO$_2$, 50% ethyl acetate in petroleum ether) to give the title compound. MS: 356 (M+1).

Step 4: 3-ethyl-7-(hydroxymethyl)-6-methyl-2-(5-((1-methylcyclopropyl)methoxy)-2-azabicyclo[4.1.0] heptan-2-yl)-6,7-dihydro-5H-pyrrolo[3,4-b]pyridin-5-one A 100 mL three-necked round bottom flask equipped with mechanical stirrer, addition funnel and thermometer was charged with 3-ethyl-6-methyl-2-(5-((1-methylcyclopropyl)methoxy)-2-azabicyclo[4.1.0]heptan-2-yl)-6,7-dihydro-5H-pyrrolo[3,4-b]pyridin-5-one (120 mg, 0.338 mmol) in THF (3 mL), to which was added LiHMDS (1.182 mL, 1.182 mmol) dropwise at 0° C. The reaction mixture was stirred at −70° C. for 30 min. Then a solution of (1H-benzo[d][1,2,3]triazol-1-yl)methanol (91 mg, 0.608 mmol) in THF (2 mL) was added via syringe over 2 min. The reaction mixture was diluted with water (50 mL) and extracted with ethyl acetate (130 mL×3). The combined organic layers were washed with brine (50 mL), dried over Na$_2$SO$_4$, filtered and the filtrate was concentrated in vacuo. The residue was purified by prep-TLC (SiO$_2$, 50% ethyl acetate in petroleum ether) to give the title compound. MS: 386 (M+1).

Step 5: 3-ethyl-7-(hydroxymethyl)-6-methyl-2-(5-((1-methylcyclopropyl)methoxy)-2-azabicyclo[4.1.0] heptan-2-yl)-6,7-dihydro-5H-pyrrolo[3,4-b]pyridin-5-one A mixture of 3-ethyl-7-(hydroxymethyl)-6-methyl-2-(5-((1-methylcyclopropyl)methoxy)-2-azabicyclo[4.1.0]heptan-2-yl)-6,7-dihydro-5H-pyrrolo[3,4-b]pyridin-5-one (55 mg, 0.143 mmol) was separated by SFC (Chiralpak IC-H 250*30 5u, 45% IPA with 0.1% NH₃H₂O/CO₂ at 50 mL/min) and recrystallized to give the four isomers. Example 9 (first peak): MS: 386.1 (M+1). ¹H NMR: (400 MHz, CDCl₃): δ 7.78 (1H, s), 4.26-4.29 (1H, m), 4.05-4.19 (2H, m), 3.82-3.87 (1H, m), 3.66-3.70 (1H, m), 3.37-3.42 (2H, m), 3.24 (1H, d, J=9.6 Hz), 3.11 (3H, s), 2.86-2.99 (4H, m), 2.1-2.06 (1H, m), 1.55-1.64 (1H, m), 1.35-1.44 (1H, m), 1.24 (3H, t, J=14.8 Hz), 1.14 (3H, s), 0.88-0.97 (1H, m), 0.68-0.72 (1H, m), 0.38-0.43 (2H, m), 0.33-0.36 (2H, m). Example 10 (second peak): MS: 386.1 (M+1). ¹H NMR: (400 MHz, CDCl₃): δ 7.79 (1H, s), 4.26-4.29 (1H, m), 4.05-4.16 (2H, m), 3.82-3.87 (1H, m), 3.66-3.70 (1H, m), 3.37-3.42 (2H, m), 3.24 (1H, d, J=9.6 Hz), 3.11 (3H, s), 2.86-2.99 (4H, m), 2.00-2.06 (1H, m), 1.55-1.64 (1H, m), 1.35-1.44 (1H, m), 1.24 (3H, t, J=14.8 Hz), 1.14 (3H, s), 0.88-0.94 (1H, m), 0.68-0.72 (1H, m), 0.38-0.43 (2H, m), 0.33-0.36 (2H, m). Example 11 (third peak): MS: 386.1 (M+1). ¹H NMR: (400 MHz, CDCl₃): δ7.80 (1H, s), 4.26-4.29 (1H, m), 4.05-4.16 (2H, m), 3.82-3.87 (1H, m), 3.66-3.70 (1H, m), 3.37-3.42 (2H, m), 3.24 (1H, d, J=9.6 Hz,), 3.11 (3H, s), 2.99-2.86 (4H, m), 2.01-2.06 (1H, m), 1.55-1.64 (1H, m), 1.35-1.44 (1H, m), 1.24 (3H, t, J=14.8 Hz), 1.15 (3H, s), 0.88-0.94 (1H, m), 0.68-0.72 (1H, m), 0.38-0.43 (2H, m), 0.33-0.36 (2H, m). Example 12 (forth peak): MS: 386.1 (M+1). ¹H NMR: (400 MHz, CDCl₃): δ7.79 (1H, s), 4.26-4.29 (1H, m), 4.05-4.16 (2H, m), 3.82-3.87 (1H, m), 3.66-3.70 (1H, m), 3.37-3.42 (2H, m), 3.24 (1H, d, J=9.6 Hz), 3.11 (3H, s), 2.86-2.99 (4H, m), 2.01-2.06 (1H, m), 1.55-1.64 (1H, m), 1.35-1.44 (1H, m), 1.24 (3H, t, J=14.8 Hz), 1.15 (3H, s), 0.88-0.94 (1H, m), 0.68-0.72 (1H, m), 0.38-0.43 (2H, m), 0.33-0.36 (2H, m).

SCHEME 4

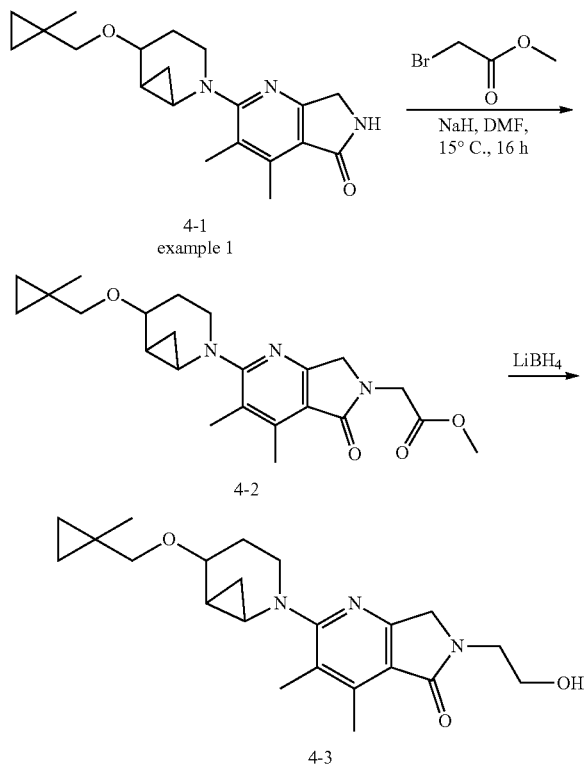

Example 13 & Example 14

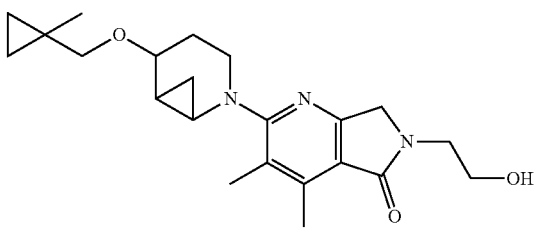 [SMILES: Cc1c(N2CCC(OCC3(C)CC3)C3CC32)nc2c(c1C)C(=O)N(CCO)C2]

6-(2-hydroxyethyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Scheme 3)

Step 1: Methyl 2-(3,4-dimethyl-2-(5-((1-methylcyclopropyl)methoxy)-2-azabicyclo-[4.1.0]heptan-2-yl)-5-oxo-5,7-dihydro-6H-pyrrolo[3,4-b]pyridin-6-yl)acetate To a solution of 3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Example 1 compound, 70 mg, 0.164 mmol) in DMF (3 mL) was added NaH (7.22 mg, 0.180 mmol, 60% w), and the mixture was stirred at 0° C. for 30 min, then methyl 2-bromoacetate (30.1 mg, 0.197 mmol) was added to the mixture and the reaction was stirred at 15° C. for 16 h. The reaction mixture was quenched with water (10 mL), then the mixture was extracted with EtOAc (10 mL×3). The combined organic layers were washed with brine, dried over anhydrous sodium sulfate, filtered and concentrated to provide the title compound, which was used directly in the next step. MS: 414.2 (M+1).

Step 2: 6-(2-hydroxyethyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of methyl 2-(3,4-dimethyl-2-(5-((1-methylcyclopropyl)methoxy)-2-azabicyclo[4.1.0]heptan-2-yl)-5-oxo-5H-pyrrolo[3,4-b]pyridin-6(7H)-yl)acetate (70 mg, 0.135 mmol) in THF (3 mL) was added LiBH₄ (5.90 mg, 0.271 mmol) and the mixture was stirred at 15° C. for 1 h. The reaction mixture was quenched with MeOH (5 mL), then the mixture was concentrated to give the residue, which was further purified by prep-TLC (Petrolem.ether:EtOAc=1:2) and then further separated by chiral SFC (AD, (250 mm*30 mm, 10 um), 40% EtOH with 0.1% NH₃.H₂O/CO₂ at 80 mL/min) to give two isomers. Example 13: MS: 386.1 (M+1). ¹H NMR (400 MHz, CDCl₃): δ 4.42 (2H, s), 4.08-4.14 (1H, m), 3.68-3.79 (5H, m), 3.47 (1H, d, J=5.6 Hz), 3.30-3.303 (1H, m), 2.95-3.05 (2H, m), 2.64 (3H, s), 2.39 (3H, s), 1.98-2.02 (1H, m), 1.63-1.69 (1H, m), 1.48-1.51 (1H, m), 1.14 (3H, s), 0.94-0.99 (1H, m), 0.70-0.75 (1H, m), 0.43-0.44 (2H, m), 0.32-0.35 (2H, m). Example 14: MS: 386.1 (M+1). ¹H NMR (400 MHz, CDCl₃): δ 4.41 (2H, s), 4.08-4.14 (1H, m), 3.67-3.80 (5H, m), 3.47 (1H, d, J=5.6 Hz), 3.30-3.33 (1H, m), 2.95-3.05 (2H, m), 2.64 (3H, s), 2.39 (3H, s), 1.98-2.02 (1H, m), 1.63-1.69 (1H, m), 1.48-1.51 (1H, m), 1.14 (3H, s), 0.94-0.99 (1H, m), 0.70-0.75 (1H, m), 0.43-0.44 (2H, m), 0.32-0.35 (2H, m).

The following examples in Table 2 were prepared according to the first step in scheme 3 using Example 11 compound and the appropriate SN2 reaction partner as the starting materials and following the first step procedure for Examples 13 and 14.

TABLE 2

| Ex | Structure | Name | MS (M + 1) | ¹H NMR |
|---|---|---|---|---|
| 15 | 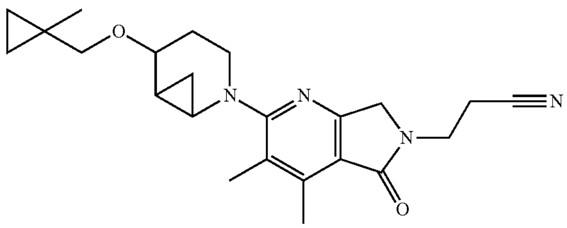 [SMILES: Cc1c(N2CCC(OCC3(C)CC3)C3CC32)nc2c(c1C)C(=O)N(CCC#N)C2] | 3-(3,4-dimethyl-2-(5-((1-methylcyclopropyl)methoxy)-2-azabicyclo[4.1.0]heptan-2-yl)-5-oxo-5,7-dihydro-6H-pyrrolo[3,4-b]pyridin-6-yl)propanenitrile | 395.1 | (400 MHz, Methanol-d4): δ 4.37 (2 H, s), 4.10-4.15 (1 H, m), 3.86 (2 H, t, J = 6.8 Hz), 3.75-3.78 (1 H, m), 3.47 (1 H, d, J = 9.6 Hz), 3.31-3.33 (1 H, m), 2.97-3.01 (2 H, m), 2.83-2.87 (2 H, m), 2.62 (3 H, s), 2.37 (3 H, s), 1.98-2.02 (1 H, m), 1.60-1.65 (1 H, m), 1.48-1.50 (1 H, m), 1.14 (3 H, s), 0.91-0.94 (1 H, m, 1H), 0.56-0.58 (1 H, m), 0.42-0.44 (2 H, m), 0.31-0.33 (2 H, m). |
| 16 | 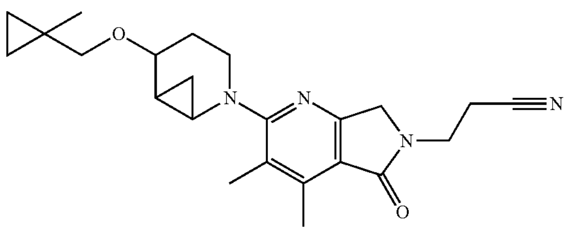 [SMILES: Cc1c(N2CCC(OCC3(C)CC3)C3CC32)nc2c(c1C)C(=O)N(CCC#N)C2] | 3-(3,4-dimethyl-2-(5-((1-methylcyclopropyl)methoxy)-2-azabicyclo[4.1.0]heptan-2-yl)-5-oxo-5,7-dihydro-6H-pyrrolo[3,4-b]pyridin-6-yl)propanenitrile | 395.1 | (400 MHz, Methanol-d4): δ 4.36 (2 H, s), 4.10-4.15 (1 H, m), 3.86 (2 H, t, J = 6.8 Hz), 3.75-3.78 (1 H, m), 3.47 (1 H, d, J = 9.6 Hz), 3.31-3.33 (1 H, m), 2.97-3.01 (2 H, m), 2.83-2.87 (2 H, m), 2.62 (3 H, s), 2.37 (3 H, s), 1.98-2.02 (1 H, m), 1.60-1.65 (1 H, m), 1.48-1.50 (1 H, m), 1.14 (3 H, s), 0.91-0.94 (1 H, m), 0.56-0.58 (1 H, m), 0.42-0.44 (2 H, m), 0.31-0.34 (2 H, m). |
| 17 | 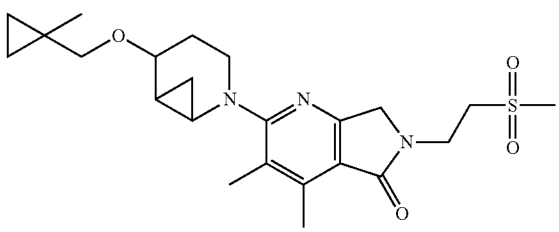 [SMILES: Cc1c(N2CCC(OCC3(C)CC3)C3CC32)nc2c(c1C)C(=O)N(CCS(C)(=O)=O)C2] | 3,4-dimethyl-2-(5-((1-methylcyclopropyl)methoxy)-2-azabicyclo[4.1.0]heptan-2-yl)-6-(2-(methylsulfonyl)ethyl)-6,7-dihydro-5H-pyrrolo[3,4-b]pyridin-5-one | 448.1 | (400 MHz, CDCl₃): δ 4.53-4.58 (2 H, m), 4.07-4.10 (3 H, m), 3.62-3.65 (1 H, m), 3.41-3.44 (3 H, m), 3.28-3.34 (3 H, m), 3.00 (3 H, s), 2.91-2.94 (1 H, m), 2.70 (3 H, s), 2.41 (3 H, s), 2.07-2.11 (1 H, m), 1.72-1.76 (1 H, m), 1.47-1.54 (1 H, m), 1.12-1.15 (4 H, m), 0.91-0.95 (1 H, m), 0.35-0.43 (4 H, m). |
| 18 | 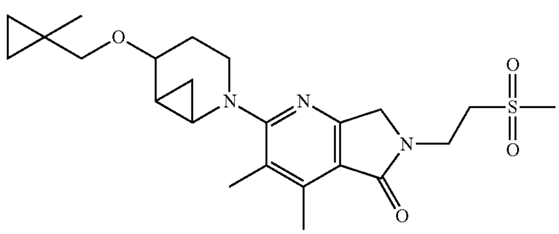 [SMILES: Cc1c(N2CCC(OCC3(C)CC3)C3CC32)nc2c(c1C)C(=O)N(CCS(C)(=O)=O)C2] | 3,4-dimethyl-2-(5-((1-methylcyclopropyl)methoxy)-2-azabicyclo[4.1.0]heptan-2-yl)-6-(2-(methylsulfonyl)ethyl)-6,7-dihydro-5H-pyrrolo[3,4-b]pyridin-5-one | 448.1 | (400 MHz, CDCl₃): δ 4.49-4.64 (2 H, m), 4.07-4.10 (3 H, m), 3.61-3.64 (1 H, m), 3.41-3.43 (3 H, m), 3.29-3.34 (2 H, m), 3.00 (3 H, s), 2.91-2..94 (1 H, m), 2.70 (3 H, s), 2.41 (3 H, s), 2.07-2.11 (1 H, m), 1.72-1.76 (1 H, m), 1.47-1.54 (1 H, m), 1.12-1.15 (4 H, m), 0.91-0.95 (1 H, m), 0.35-0.43 (4 H, m). |

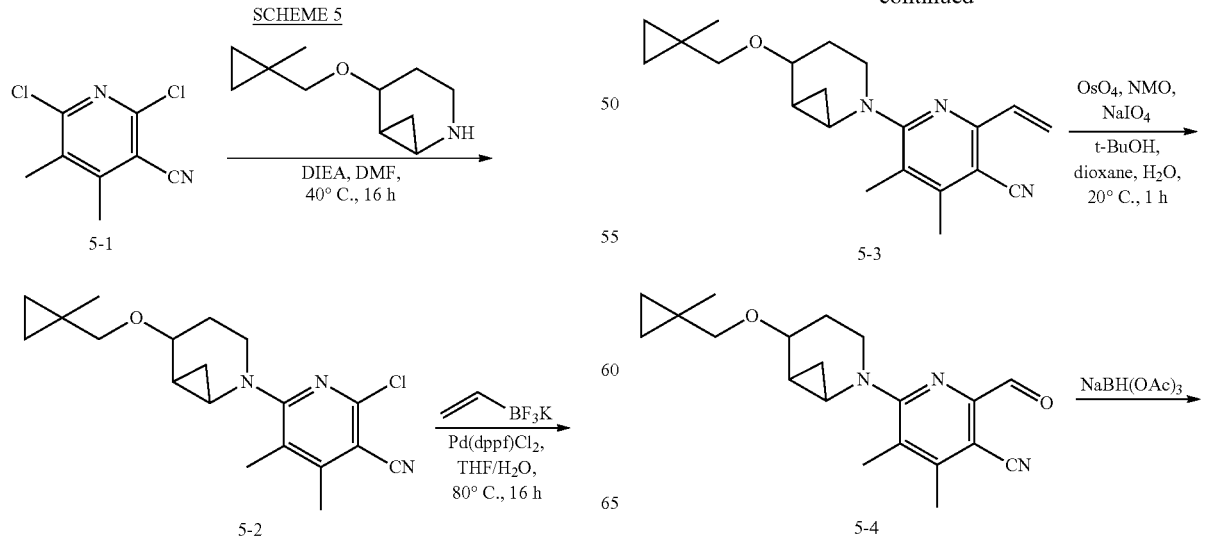

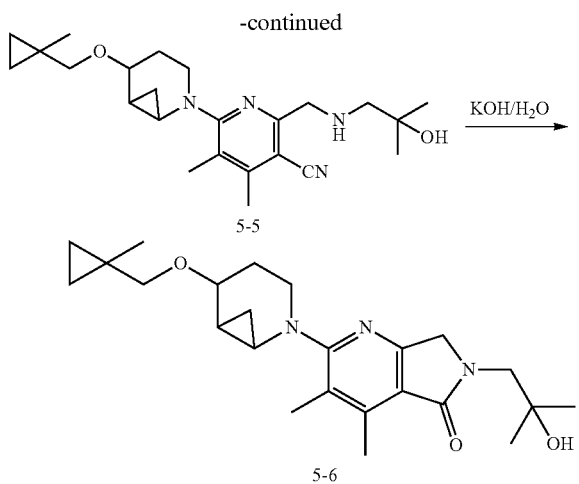

5-5

5-6

Example 19 & Example 20

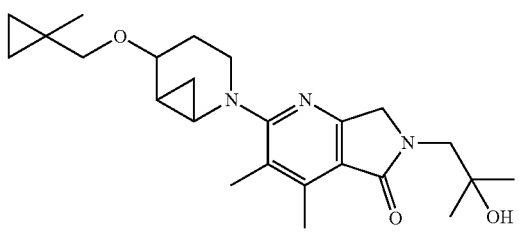 [SMILES: Cc1c(N2CCC(OCC3(C)CC3)C3CC32)nc2c(c1C)C(=O)N(CC(C)(C)O)C2]

6-(2-hydroxy-2-methylpropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Scheme 4)

Step 1: 2-chloro-4,5-dimethyl-6-(5-((1-methylcyclopropyl)methoxy)-2-azabicyclo[4.1.0]heptan-2-yl) nicotinonitrile To a solution of 2,6-dichloro-4,5-dimethylnicotinonitrile (intermediate D, 776 mg, 3.86 mmol) in DMF (6 mL) was added 5-((1-methylcyclopropyl)methoxy)-2-azabicyclo-[4.1.0]heptane (intermediate C, 700 mg, 3.86 mmol) and triethylamine (0.807 mL, 5.79 mmol) at 20° C. under $N_2$. Then the mixture was stirred at 40° C. for 16 h. The mixture was cooled to r.t. and quenched with water (20 mL) and extracted with ethyl acetate (15 mL×3). The organic layer was dried over anhydrous sodium sulfate, filtered and the filtrate was concentrated in vacuo. The residue was purified by combiflash (PE:EtOAc=9:1) to provide the title compound. 1H NMR (400 MHz, CDCl$_3$): δ 4.03-4.06 (1H, m), 3.82-3.84 (1H, m), 3.40 (1H, d, J=9.6 Hz), 3.30 (1H, d, J=9.6 Hz), 2.88-2.92 (2H, m), 2.44 (3H, s), 2.32 (3H, s), 1.98-2.03 (1H, m), 1.62-1.68 (1H, m), 1.39-1.43 (1H, m), 1.15 (3H, s), 0.96-0.99 (1H, m), 0.71-0.73 (1H, m), 0.35-0.41 (4H, m).

Step 2: 4,5-dimethyl-6-(5-((1-methylcyclopropyl) methoxy)-2-azabicyclo[4.1.0]heptan-2-yl)-2-vinylnicotinonitrile To a solution of $K_3PO_4$ (1.841 g, 8.67 mmol), 2-chloro-4,5-dimethyl-6-(5-((1-methylcyclopropyl)methoxy)-2-azabicyclo[4.1.0]heptan-2-yl)nicotinonitrile (1.0 g, 2.89 mmol) and potassium vinyltrifluoroborate (0.465 g, 3.47 mmol) in THF (3 mL) and water (0.6 mL) was added PdCl$_2$(dppf)-CH$_2$Cl$_2$ adduct (0.236 g, 0.289 mmol) and the mixture was degassed and refilled with N$_2$ atmosphere for 3 times. Then the mixture was stirred at 80° C. for 16 h. The reaction mixture was quenched with water (10 mL) and then the mixture was extracted with EtOAc (10 mL×3). The combined organic layers were washed with brine, dried over anhydrous sodium sulfate, filtered and concentrated to give a residue, which was further purified by column chromography (SiO$_2$:pretrolem.ether:EtOAc=5:1) to provide the title compound. MS: 338.2 (M+1). $^1$H NMR (400 MHz, CDCl$_3$): δ 7.09 (1H, dd, J=10.8 Hz, 16.8 Hz), 6.46 (1H, d, J=14.8 Hz), 5.53 (1H, d, J=8.8 Hz), 4.06-4.10 (1H, m), 3.93-3.96 (1H, m), 3.42 (1H, d, J=9.6 Hz), 3.20 (1H, d, J=10.0 Hz), 2.91-2.98 (2H, m), 2.44 (3H, s), 2.33 (3H, s), 1.95-2.02 (1H, m), 1.46-1.49 (1H, m), 1.15 (3H, s), 0.91-0.93 (1H, m), 0.64-0.67 (1H, m), 0.35-0.43 (4H, m).

Step 3: 2-formyl-4,5-dimethyl-6-(5-((1-methylcyclopropyl)methoxy)-2-azabicyclo[4.1.0]heptan-2-yl) nicotinonitrile To a solution of 4,5-dimethyl-6-(5-((1-methylcyclopropyl)methoxy)-2-azabicyclo[4.1.0]heptan-2-yl)-2-vinylnicotinonitrile (539 mg, 1.597 mmol) in 1,4-dioxane (1.0 mL), t-BuOH (0.5 mL) and water (1.0 mL) were added NMO (225 mg, 1.917 mmol) and osmium tetroxide (122 mg, 0.479 mmol). The mixture was stirred at 25° C. for 20 min and then the mixture was added sodium periodate (1708 mg, 7.99 mmol) and stirred at 25° C. for 20 min. The reaction mixture was quenched with water (10 mL) and extracted with EtOAc (5 mL×3). The combined organic layers were washed with brine (10 mL), dried over anhydrous sodiums sulfate and filtered. The filtrate was concentrated to give a residue, which was purified by pre-TLC (Petrolem.ether:EtOAc=3:1) to provide the title compound.

Step 4: 2-(((2-hydroxy-2-methylpropyl)amino) methyl)-4,5-dimethyl-6-(5-((1-methylcyclopropyl) methoxy)-2-azabicyclo[4.1.0]heptan-2-yl)nicotinonitrile To a solution of 2-formyl-4,5-dimethyl-6-(5-((1-methylcyclopropyl)methoxy)-2-azabicyclo[4.1.0]heptan-2-yl) nicotinonitrile (224 mg, 0.660 mmol) in DCE (3 mL) was added 1-amino-2-methylpropan-2-ol (88 mg, 0.990 mmol) and AcOH (3.78 μL, 0.066 mmol). The mixture was stirred at 40° C. for 0.5 h and then sodium triacetoxyborohydride (280 mg, 1.320 mmol) was added and the mixture was stirred at 40° C. for 16 h. The reaction mixture was quenched with saturated NaHCO$_3$ aqueous (~10 mL), then the mixture was extracted with EtOAc (10 mL×3). The combined organic layers were washed with brine, dried over anhydrous sodium sulfate, and filtered, and the filtrate was concentrated to get a residue, which was further purified by pre-TLC (dichloromethane:MeOH=10:1) to provide the title compound. MS: 413.3 (M+1).

Step 5: 6-(2-hydroxy-2-methylpropyl)-3,4-dimethyl-2-(5-((1-methylcyclopropyl)methoxy)-2-azabicyclo [4.1.0]heptan-2-yl)-6,7-dihydro-5H-pyrrolo[3,4-b] pyridin-5-one To a solution of 2-(((2-hydroxy-2-methylpropyl)amino) methyl)-4,5-dimethyl-6-(5-((1-methylcyclopropyl)

methoxy)-2-azabicyclo[4.1.0]heptan-2-yl)nicotinonitrile (125 mg, 0.303 mmol) in water (3 mL) and MeOH (0.5 mL) was added potassium hydroxide (510 mg, 9.09 mmol), the mixture was stirred at 100° C. for 4 h. The reaction mixture was quenched with 1N HCl to pH~7, then the mixture was extracted with EtOAc (10 mL×3). The combined organic layers were washed with brine, dried over anhydrous sodium sulfate, filtered and concentrated to give a residue, which was further purified by prep-HPLC (TFA) to provide the title compound as a yellow oil. The title compound was further separated by chiral SFC (AD (250 mm*30 mm, 10 um), 40% EtOH with 0.1% NH3.H2O/CO2 at 60 mL/min) to give two isomers. Example 19 (first peak): MS: 414.1 (M+1). $^1$H NMR (400 MHz, CDCl$_3$): δ 4.48-4.70 (2H, m), 4.05-4.15 (1H, m), 3.60-3.73 (3H, m), 3.20-3.45 (3H, m), 2.95-3.00 (1H, m), 2.70 (3H, s), 2.41 (3H, s), 2.07-2.12 (1H, m), 1.60-1.75 (1H, m), 1.40-1.55 (1H, m), 1.24-1.28 (7H, m), 1.00-1.16 (4H, m), 0.80-0.90 (1H, m), 0.36-0.42 (4H, m). Example 20 (second peak): MS: 414.1 (M+1). $^1$H NMR (400 MHz, CDCl$_3$): δ 4.55-4.70 (2H, m), 4.07-4.11 (1H, m), 3.64-3.67 (3H, m), 3.20-3.45 (3H, m), 2.85-2.92 (1H, m), 2.72 (3H, s), 2.42 (3H, s), 2.09-2.12 (1H, m), 1.60-1.75 (1H, m), 1.40-1.55 (1H, m), 1.24-1.28 (7H, m), 1.00-1.16 (4H, m), 0.80-0.90 (1H, m), 0.36-0.42 (4H, m).

SCHEME 6

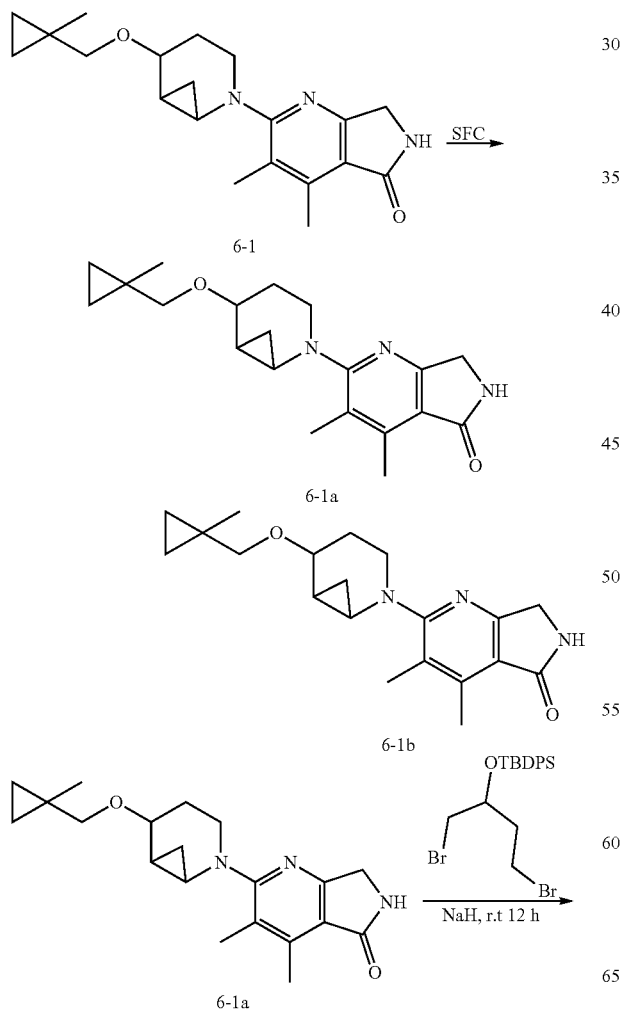

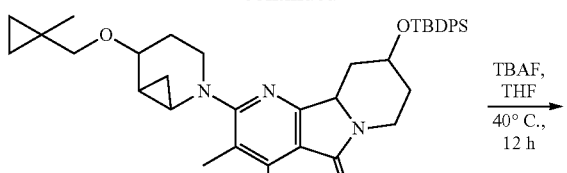

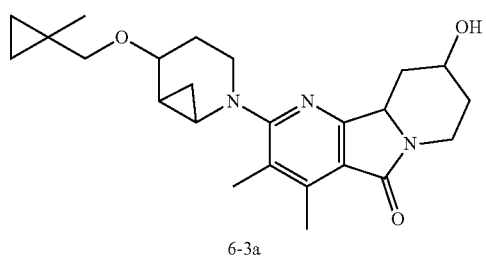

Example 21 & 22

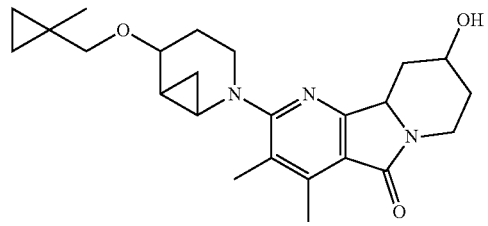 [SMILES: Cc1c(N2CCC(OCC3(C)CC3)C3CC32)nc2c(c1C)C(=O)N1CCC(O)CC21]

9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one (Scheme 6)

Resolution of 8-((tert-butyldiphenylsilyl)oxy)-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one 3,4-Dimethyl-2-(5-((1-methylcyclopropyl)methoxy)-2-azabicyclo[4.1.0]heptan-2-yl)-6,7-dihydro-5H-pyrrolo[3,4-b]pyridin-5-one (racemic Example 1 compound, 0.9 g, 2.64 mmol) was resolved by SFC (AD(250 mm*30 mm, 5 um), 35% MeOH with 0.1% NH$_3$H$_2$O/CO$_2$ at 60 Ml/min)) to give two isomers as 6-1a and 6-1b.

Step 1: 8-((tert-butyldiphenylsilyl)oxy)-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one To a solution of 6-1a in DMF (10 ml) was added sodium hydride (83 mg, 2.255 mmol) at 0° C. and the mixture was stirred for 30 min. Then to the reaction was added tert-butyl ((1,4-dibromobutan-2-yl)oxy)diphenylsilane (482 mg, 1.025 mmol). The reaction was stirred at 25° C. for 12 h. The reaction mixture was quenched with water (15 mL) and extracted with Ethyl acetate (30 mL×3). The organic layer was dried over anhydrous sodium sulfate, filtered and the filtrate was concentrated to give the crude title compound, which was directly used to next step without further purification. MS: 650.5 (M+1).

Step 2: 9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one and 9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]Indolizin-5(7H)-one To a solution of 8-((tert-butyldiphenylsilyl)oxy)-3,4-dimethyl-2-(5-((1-methylcyclopropyl) methoxy)-2-azabicyclo[4.1.0]heptan-2-yl)-8,9,10,10a-tetrahydropyrido[2,3-a]indolizin-5(7H)-one (666 mg, 1.025 mmol) in THF (3 mL) was added TBAF (1.025 ml, 1.025 mmol) and the reaction was stirred at 25° C. for 12 h. Then the reaction was quenched by $H_2O$ (30 mL) and extracted with ethyl acetate (5 mL×3). The organic layer was dried over anhydrous sodium sulfate, filtered and the filtrate was concentrated in vacuo, which was purified by prep-TLC (PE:EtOAc=1:3) to provide the title compounds. Example 21: MS: 412.1 (M+1) $^1$H NMR (400 MHz, CDCl$_3$): δ 4.15-4.25 (2H, t, J=6.0 Hz), 4.00-4.10 (1H, m), 3.65-3.75 (3H, m), 3.40-3.45 (1H, d, J=9.6 Hz), 3.00-3.10 (1H, d, J=9.6 Hz), 2.90-3.05 (2H, m), 2.82-2.87 (1H, m), 2.75-2.80 (1H, m), 2.63 (3H, s), 2.45-2.50 (1H, m), 2.32 (3H, s), 1.90-2.05 (2H, m), 1.75-1.80 (1H, m), 1.65-1.70 (1H, m), 1.45-1.65 (2H, m), 1.15 (3H, s), 0.85-0.95 (1H, m), 0.60-0.65 (1H, m). 0.35-0.45 (2H, m), 0.30-0.35 (2H, m). Example 22: MS: 412.1 (M+1) $^1$H NMR (400 MHz, MeOD): δ 4.45-4.50 (1H, m), 4.13 (1H, s), 4.10-4.21 (2H, m), 3.75-3.85 (1H, m), 3.42-3.48 (1H, d, J=9.6 Hz), 3.32-3.40 (1H, d, J=9.6 Hz), 2.80-2.96 (2H, m), 2.61 (3H, s), 2.63 (3H, s), 2.40-2.48 (1H, m), 2.35 (3H, s), 1.95-2.05 (1H, m), 1.80-1.90 (1H, m), 1.55-1.65 (2H, m), 1.41-1.49 (1H, m), 1.20-1.30 (2H, m), 1.13 (3H, s), 0.85-0.95 (1H, m), 0.52-0.60 (1H, m). 0.40-0.45 (2H, m), 0.25-0.30 (2H, m).

The following examples in Table 3 were prepared according to scheme 6 following the procedure outlined in the synthesis of Example 21 and Example 22 but from starting material 6-1b.

TABLE 3

| Ex | Structure | Name | MS (M + 1) | $^1$H NMR |
|----|-----------|------|------------|-----------|
| 23 | 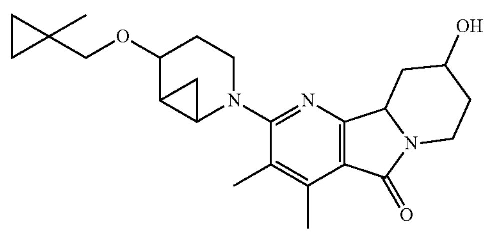 [SMILES: Cc1c(N2CCC(OCC3(C)CC3)C3CC32)nc2c(c1C)C(=O)N1CCC(O)CC21] | 9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one | 412.1 | (400 MHz, CDCl$_3$): δ 4.15-4.25 (2 H, t, J = 6 Hz), 4.00-4.10 (1H, m), 3.65-3.75 (3 H, m), 3.40-3.45 (1 H, d, J = 9.6 Hz), 3.00-3.10 (1 H, d, J = 9.6 Hz), 2.90-3.05 (2 H, m), 2.82-2.87 (1 H, m), 2.75-2.80 (1 H, m), 2.63 (3 H, s), 2.45-2.50 (1 H, m), 2.32 (3 H, s), 1.90-2.05 (2 H, m), 1.75-1.80 (1 H, m), 1.65-1.70 (1 H, m), 1.45-1.65 (2 H, m), 1.15 (3 H, s), 0.85-0.95 (1 H, m), 0.60-0.65 (1 H, m). 0.35-0.45 (2 H, m), 0.30-0.35 (2 H, m). |
| 24 | 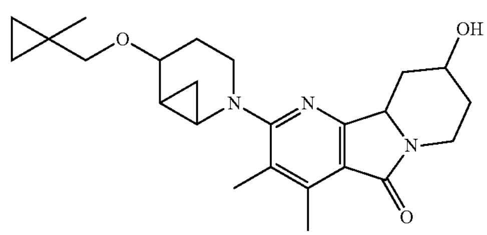 [SMILES: Cc1c(N2CCC(OCC3(C)CC3)C3CC32)nc2c(c1C)C(=O)N1CCC(O)CC21] | 9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one | 412.1 | (400 MHz, MeOD): δ 4.45-4.50 (1 H, m), 4.13 (1 H, s), 4.10-4.21 (2 H, m), 3.75-3.85 (1H, m), 3.42-3.48 (1 H, d, J = 9.6 Hz), 3.32-3.40 (1 H, d, J = 9.6 Hz), 2.80-2.96 (2 H, m), 2.61 (3 H, s), 2.63 (3 H, s), 2.40-2.48 (1 H, m), 2.35 (3 H, s), 1.95-2.05 (1 H, m), 1.80-1.90 (1 H, m), 1.55-1.65 (2 H, m), 1.41-1.49 (1 H, m), 1.20-1.30 (2 H, m), 1.13 (3 H, s), 0.85-0.95 (1 H, m), 0.52-0.60 (1 H, m), 0.40-0.45 (2 H, m), 0.25-0.30 (2 H, m) |

SCHEME 7

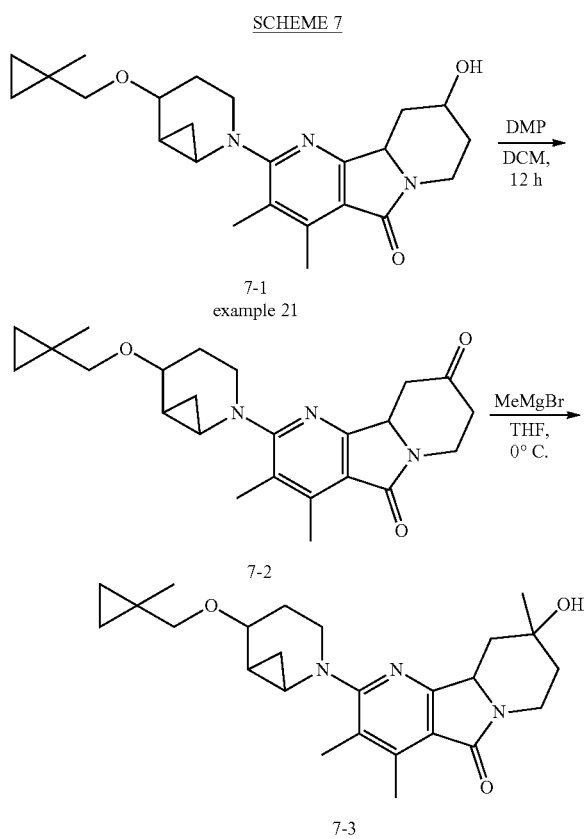

Example 25

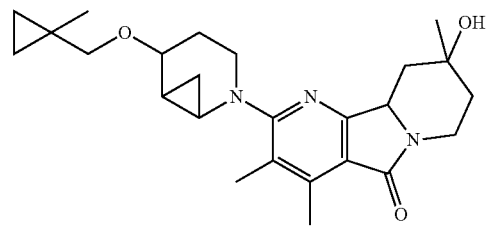 [SMILES: Cc1c(N2CCC(OCC3(C)CC3)C3CC32)nc2c(c1C)C(=O)N1CCC(C)(O)CC21]

9-hydroxy-3,4,9-trimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one (Scheme 6)

Step 1: 3,4-dimethyl-2-(5-((1-methylcyclopropyl)methoxy)-2-azabicyclo[4.1.0]heptan-2-yl)-7,8,10,10a-tetrahydropyrido[2,3-a]indolizine-5,9-dione To a solution of 9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one (Example 21 compound, 140 mg, 0.340 mmol) in dichloromethane (3 ml) was added Dess-MartinPeriodinane (144 mg, 0.340 mmol) at 25° C. After addition, the mixture was stirred at 25° C. for 16 h. The reaction mixture was filtered and the filtrate was concentrated to give a crude, which was purified by prep-TLC (SiO$_2$, PE:EtOAc=1:1) to provide the title compound. MS: 410.2 (M+1).

Step 2: 9-hydroxy-3,4,9-trimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one To a solution of 3,4-dimethyl-2-(5-((1-methylcyclopropyl)methoxy)-2-azabicyclo[4.1.0]heptan-2-yl)-7,8,10,10a-tetrahydropyrido[2,3-a]indolizine-5,9-dione (50 mg, 0.122 mmol) in THF (3 mL) was added methylmagnesium bromide (0.081 mL, 0.244 mmol) at 0° C. The reaction mixture was stirred at 0° C. for 2 h. Then the mixture was quenched with NH$_4$Cl (5 mL). The mixture was extracted with EtOAc (10 mL×3) and the combined organic layers were washed with water (5 mL×2), brine (5 mL), dried over anhydrous Na$_2$SO$_4$, filtered and concentrated to give a residue which was further purified by prep-TLC (SiO$_2$, PE:EA=2:1) and prep-HPLC (neu) to provide the title compound. MS: 426.1 (M+1). $^1$H NMR (400 MHz, MeOD): δ 4.25-4.35 (1H, m), 4.20-4.28 (1H, m), 4.05-4.15 (1H, m), 3.75-3.95 (1H, m), 3.45-3.55 (1H, dd, J=2.0 Hz, 2.0 Hz), 3.32-3.36 (1H, m), 2.90-3.15 (3H, m), 2.61 (3H, s), 2.36 (3H, s), 2.40-2.48 (1H, m), 2.35 (3H, s), 2.25-2.35 (1H, m), 1.90-2.00 (1H, m), 1.70-1.80 (1H, m), 1.55-1.65 (1H, m), 1.40-1.52 (5H, m), 1.25-1.35 (1H, m), 1.05-1.15 (4H, m), 0.80-0.95 (1H, m), 0.55-0.60 (1H, m). 0.40-0.45 (2H, m), 0.25-0.30 (2H, m)

SCHEME 8

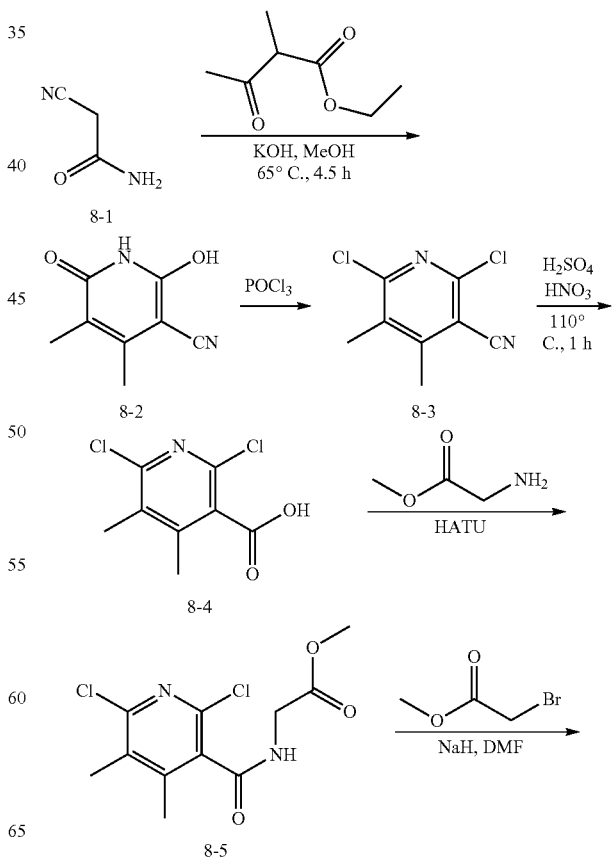

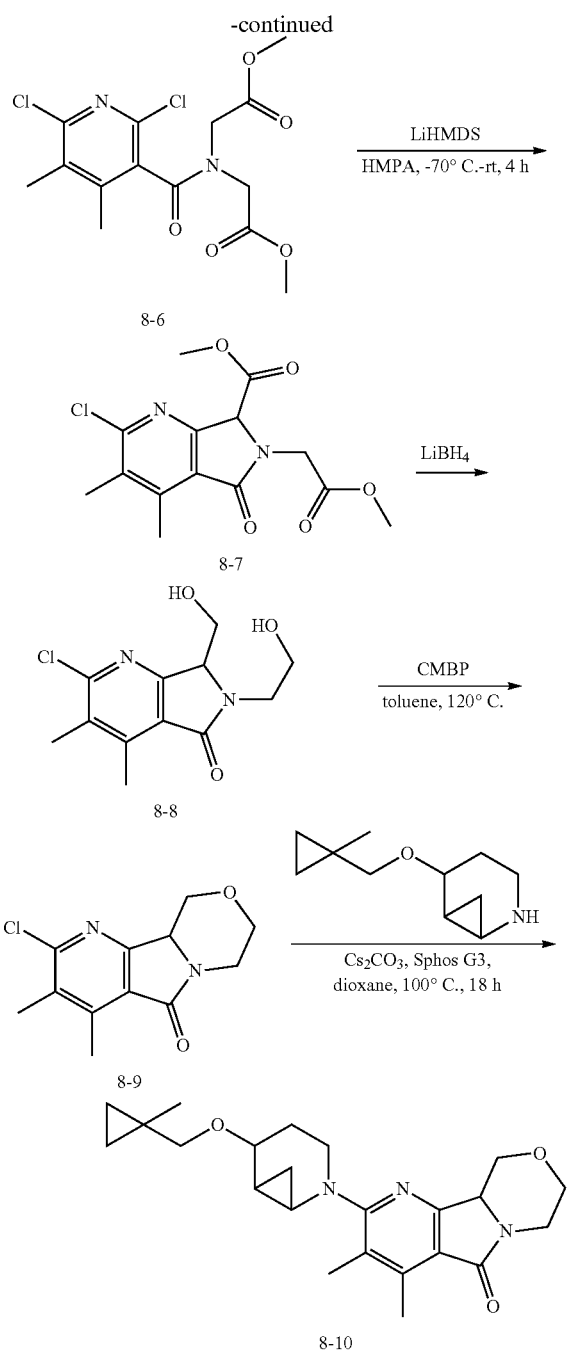

3,4-dimethyl-2-(5-((1-methylcyclopropyl)methoxy)-2-azabicyclo[4.1.0]heptan-2-yl)-7,8,10,10a-tetrahydro-5H-pyrido[2',3':3,4]pyrrolo[2,1-c][1,4]oxazin-5-one (Scheme 8)

Step 1: 2,6-dihydroxy-4,5-dimethylnicotinonitrile

A solution of 2-cyanoacetamide (50 g, 595 mmol), ethyl 2-methyl-3-oxobutanoate (86 g, 595 mmol) and KOH (41.7 g, 743 mmol) in MeOH (750 mL) was stirred for 4 h at 65° C. in an oil bath. The reaction mixtures were cooled to 10° C. with a water/ice bath. The solids were collected by filtration, and washed with 500 mL of MeOH. The solids was mixed with 4 L of 90° C. water. To the mixture was added dropwise aq. HCl (36%) to pH=1 and the mixture was stirred for 10 minutes. The solids were collected by filtration and washed with water (2 L) to give about 350 g waterish solid. Then it was concentrated in vacuo to give about 260 g solid. The solid was mixed with 2.5 L dry toluene, and concentrated to give the title compound. $^1$H NMR (DMSO, 400 MHz): δ 2.24 (3H, s), 1.91 (3H, s).

Step 2: 2,6-dichloro-4,5-dimethylnicotinonitrile

A mixture of 2,6-dihydroxy-4,5-dimethylnicotinonitrile (62.5 g, 381 mmol), benzyltriethylammonium chloride (250 g, 1098 mmol) and POCl$_3$ (125 mL, 1341 mmol) was stirred at 140° C. for 16 hours. The mixture was poured into water (1000 mL) and extracted with EtOAc (3000 mL). The organic layer was dried over Na$_2$SO$_4$, filtered through silica gel (100~200 mesh) (100 g) and the filtrate was concentrated to give a solid. The solid was washed with pet. ether/EtOAc (10:1) (100 mL) to give the title compound. $^1$H NMR (CDCl$_3$, 400 MHz): δ 2.57 (3H, s), 2.39 (3H, s).

Step 3: 2,6-dichloro-4,5-dimethylnicotinic Acid

To a mixture of 2,6-dichloro-4,5-dimethylnicotinonitrile (50 g, 249 mmol) in H$_2$SO$_4$ (125 mL, 2345 mmol) was added nitric acid (37.5 mL, 587 mmol) and the reaction stirred at 110° C. for 1 hour. The mixture was poured into ice water (500 mL) and extracted with EtOAc (2 L). The organic layer was dried over Na$_2$SO$_4$, filtered and the filtrate was concentrated to give a yellow solid. The solid was washed with pet. ether/EtOAc (10:1) (50 mL) to give the title compound. $^1$H NMR (DMSO, 400 MHz): δ 2.31 (6H, d, J=1.2 Hz).

Step 4: methyl 2-(2,6-dichloro-4,5-dimethylnicotinamido)acetate

To a solution of 2,6-dichloro-4,5-dimethylnicotinic acid (50 g, 227 mmol) and triethylamine (63.3 ml, 454 mmol) in DCM (500 mL) and DMF (0.05 mL) was added oxalyl chloride (29.8 mL, 341 mmol). After addition, the mixture was stirred at 16° C. for 0.5 h. The mixture was concentrated to afford a crude product. Then the crude product was added to a solution of methyl 2-aminoacetate HCl salt (28.5 g, 227 mmol) in DCM (500 mL), which was added the crude product at 0° C. and the reaction mixture was stirred at 16° C. for 4 h. The mixture was quenched by H$_2$O (200 mL), and extracted by DCM (200 mL×3). The combined organic phases were washed by water (150 mL), dried over Na$_2$SO$_4$, filtered and concentrated in vacuo. The residue was purified by Combiflash (35% EtOAc in petroleum ether) to give the title compound. MS: 291.0 (M+1).

Example 26

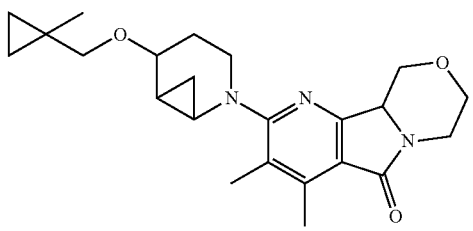 [SMILES: Cc1c(N2CCC(OCC3(C)CC3)C3CC32)nc2c(c1C)C(=O)N1CCOCC21]

Step 5: dimethyl 2,2'-((2,6-dichloro-4,5-dimethylnicotinoyl)azanediyl)diacetate

To a solution of methyl 2-(2,6-dichloro-4,5-dimethylnicotinamido) acetate (50 g, 172 mmol) in DMF (300 ml) was added sodium hydride (6.87 g, 172 mmol, 60% in mineral). After addition, the mixture was stirred at 0° C. for 15 min. Then methyl 2-bromoacetate (26.3 g, 172 mmol) was added. After addition, the mixture was stirred at 0° C. for 2 h. The mixture was quenched by saturated aqueous NH$_4$Cl (200 mL) and extracted by EtOAc (200 mL×3). The combined organic phases were washed by water (150 mL×3), dried over Na$_2$SO$_4$, filtered and concentrated in vacuo. The residue was purified by combiflash (35% EtOAc in petroleum ether) to give the title compound. MS: 363.0 (M+1).

Step 6: Methyl 2-chloro-6-(2-methoxy-2-oxoethyl)-3,4-dimethyl-5-oxo-6,7-dihydro-5H-pyrrolo[3,4-b]pyridine-7-carboxylate To a solution of dimethyl 2,2'-((2,6-dichloro-4,5-dimethylnicotinoyl)-azanediyl)diacetate (8 g, 18.72 mmol) and HMPA (19.54 mL, 112 mmol) in THF (50 mL) was added LiHMDS (37.4 ml, 37.4 mmol) at −78° C. After addition, the mixture was stirred at −78° C. for 20 min. Then the mixture was warmed to 25° C. and stirred for 1 h. The mixture was quenched by saturated aqueous NH$_4$Cl (50 mL) and extracted by EtOAc (200 mL). The organic layer was dried over anhydrous sodium sulfate, filtered and the filtrate was concentrated in vacuo. The residue was purified by Combiflash (30% EtOAc in petroleum ether) to give the title compound. MS: 327.0 (M+1).

Step 7: 2-chloro-6-(2-hydroxyethyl)-7-(hydroxymethyl)-3,4-dimethyl-6,7-dihydro-5H-pyrrolo[3,4-b]pyridin-5-one To a solution of methyl 2-chloro-6-(2-methoxy-2-oxoethyl)-3,4-dimethyl-5-oxo-6,7-dihydro-5H-pyrrolo[3,4-b]pyridine-7-carboxylate (1 g, 3.06 mmol) in THF (20 mL) was added LiBH$_4$ (0.333 g, 15.30 mmol). After addition, the mixture was stirred at 15° C. for 4 h. The mixture was quenched by water (50 mL) and extracted by EtOAc (50 mL). The organic phase was dried over Na$_2$SO$_4$, filtered and concentrated to afford a crude product. The crude product was purified by prep-TLC (SiO$_2$, THF: petroleum ether=1:1) to give the title compound. MS: 271.0 (M+1).

Step 8: 2-chloro-3,4-dimethyl-7,8,10,10a-tetrahydro-5H-pyrido[2',3':3,4]pyrrolo[2,1-c][1,4]oxazin-5-one A mixture of 2-(tributylphosphoranylidene)acetonitrile (152 mg, 0.628 mmol) and 2-chloro-6-(2-hydroxyethyl)-7-(hydroxymethyl)-3,4-dimethyl-6,7-dihydro-5H-pyrrolo[3,4-b]pyridin-5-one (100 mg, 0.369 mmol) in Toluene (1 mL) was stirred at 120° C. for 16 hours. Then the mixture was concentrated to the crude product. The crude product was purified by prep-TLC(SiO$_2$, EtOAc) to give the title compound. MS: 253.0 (M+1).

Step 9: 3,4-dimethyl-2-(5-((1-methylcyclopropyl)methoxy)-2-azabicyclo[4.1.0]heptan-2-yl)-7,8,10,10a-tetrahydro-5H-pyrido[2',3':3,4]pyrrolo[2,1-c][1,4]oxazin-5-one To a solution of 2-chloro-3,4-dimethyl-7,8,10,10a-tetrahydro-5H-pyrido[2',3':3,4]-pyrrolo[2,1-c][1,4]oxazin-5-one (300 mg, 1.187 mmol) in NMP (1.5 mL) was added 5-((1-methylcyclopropyl) methoxy)-2-azabicyclo[4.1.0]heptane (intermediate C, 323 mg, 1.781 mmol) and Cs$_2$CO$_3$ (1160 mg, 3.56 mmol). Then the reaction was stirred at 100° C. under N$_2$ atmosphere for 18 h. The reaction mixture was filtered and the filtrate was concentrated in vacuo. The residue was purified by prep-TLC (SiO$_2$, PE:EtOAc=1:1) and prep-HPLC (Base) to provide the title compound. MS: 398.1 (M+1). $^1$H NMR (400 MHz, MeOD): δ 4.61 (3H, s), 4.35-4.45 (2H, m), 4.05-4.25 (2H, m), 3.95-4.00 (1H, m), 3.70-3.85 (1H, m), 3.45-3.50 (1H, m), 2.90-3.05 (2H, m), 2.62 (3H, s), 2.36 (3H, s), 1.95-2.05 (1H, m), 1.65-1.75 (1H, m), 1.35-1.50 (1H, m), 1.25-1.35 (1H, m), 1.13 (3H, s), 0.85-0.95 (1H, m), 0.55-0.60 (1H, m), 0.35-0.45 (2H, m), 0.25-0.30 (2H, m)

SCHEME 9

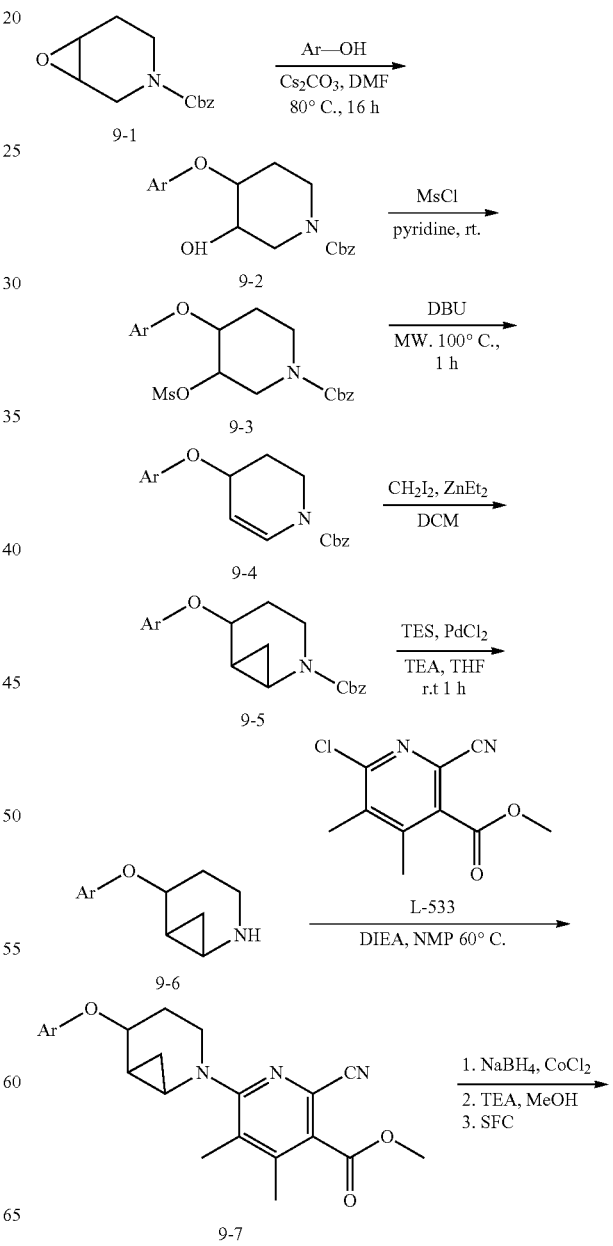

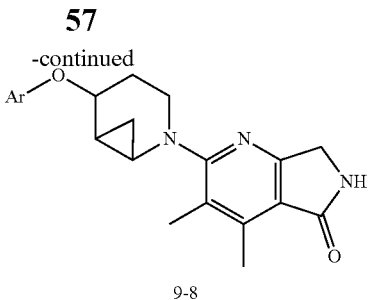

9-8

Example 27

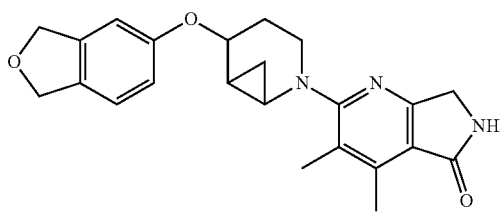 [SMILES: Cc1c(N2CCC(Oc3ccc4c(c3)COC4)C3CC32)nc2c(c1C)C(=O)NC2]

2-(5-((1,3-dihydroisobenzofuran-5-yl)oxy)-2-azabi-cyclo[4.1.0]heptan-2-yl)-3,4-dimethyl-6,7-dihydro-5H-pyrrolo[3,4-b]pyridin-5-one (Scheme 8)

Step 1: Benzyl 4-((1,3-dihydroisobenzofuran-5-yl)oxy)-3-hydroxypiperidine-1-carboxylate To a mixture of benzyl 7-oxa-3-azabicyclo[4.1.0]heptane-3-carboxylate (7 g, 30.0 mmol) and 1,3-dihydroisobenzofuran-5-ol (4.49 g, 33.0 mmol) in DMF (15 mL) was added $Cs_2CO_3$ (11.73 g, 36.0 mmol) and the mixture was heated to 80° C. with stirring under $N_2$ atmosphere for 16 h. The mixture was cooled to r.t. and diluted with water (30 mL). The mixture was extracted with ethyl acetate (30 mL×4). The combined organic layers were washed with brine (50 mL×3), dried over sodium sulfate, filtered and the filtrate was concentrated in vacuo. The residue was purified by combiflash ($SiO_2$, 50% ethyl acetate in petroleum) to provide the title compound. MS: 370.1 (M+1)

Step 2: Benzyl 4-((1,3-dihydroisobenzofuran-5-yl)oxy)-3-((methylsulfonyl)oxy)piperidine-1-carboxylate To a solution of benzyl 4-((1,3-dihydroisobenzofuran-5-yl)oxy)-3-hydroxypiperidine-1-carboxylate (8.5 g, 23.01 mmol) in pyridine (100 mL) was added Ms-Cl (2.69 mL, 34.5 mmol) and the reaction was stirred at 25° C. for 16 hours. TLC and LCMS showed the starting material was consumed and the desired product was found. The mixture was diluted with EtOAc (150 mL) and washed with water (50 mL), aq. sat. citric acid (50 mL twice), brine (50 mL), then dried over $Na_2SO_4$, filtered. The filtrate was concentrated and purified by combiflash (100 mesh) (24 g) (pet. ether:EtOAc=50:50) to provide the title compound. MS: 448.2 (M+1). $^1$H NMR (400 MHz, $CDCl_3$): δ 7.35-7.48 (5 h, m), 7.16 (1H, d, J=8.0 Hz), 6.84-6.88 (2H, m), 5.05-5.06 (6H, m), 4.60-4.85 (1H, m), 4.50-4.58 (1H, m), 3.48-4.02 (4H, m), 2.92-3.05 (3H, m), 2.13-2.23 (1H, m), 1.79-1.83 (1H, m).

Step 3: Benzyl 4-((1,3-dihydroisobenzofuran-5-yl)oxy)-3,4-dihydropyridine-1(2H)-carboxylate A mixture of benzyl 4-((1,3-dihydroisobenzofuran-5-yl)oxy)-3-((methylsulfonyl)oxy)piperidine-1-carboxylate (1.0 g, 2.235 mmol) in DBU (7.5 mL) was stirred under microwave for 1 h at 100° C. The mixture was quenched with water (20 mL), then the mixture was extracted with EtOAc (15 mL×3). The combined organic layers were washed with brine, dried over anhdrous sodium sulfate, filtered and concentrated to give a residue, which was further purified by column chromagraphy ($SiO_2$: Petrolem.ether:EtOAc=1:1) to provide the title compound. $^1$H NMR (400 MHz, $CDCl_3$): δ 7.35-7.39 (5H, m), 7.05-7.20 (2H, m), 6.80-6.85 (2H, m), 5.22 (2H, s), 5.06-5.11 (5H, m), 4.75-4.78 (1H, m), 3.90-4.05 (1H, m), 3.60-3.58 (1H, m), 2.09-2.20 (1H, m), 1.92-2.00 (1H, m).

Step 4: Benzyl 5-((1,3-dihydroisobenzofuran-5-yl)oxy)-2-azabicyclo[4.1.0]heptane-2-carboxylate To a solution of benzyl 4-((1,3-dihydroisobenzofuran-5-yl)oxy)-3,4-dihydropyridine-1(2H)-carboxylate (1.1 g, 3.13 mmol) in dichloromethane (15 mL) was added diethylzinc (9.39 mL, 9.39 mmol) at 0° C. and stirred for 30 min. Then a solution of diiodomethane (1.263 mL, 15.65 mmol) in dichloromethane (3 mL) was added dropwise to the mixture. The resulting mixture was stirred at 20° C. for 3 h under $N_2$. The reaction mixture was quenched with 1 N HCl (20 mL). Then the mixture was extracted with dichloromethane (20 mL×3). The combined organic layers were washed with brine (20 mL), dried over anhydrous sodium sulfate, filtered and the filtrate was concentrated in vacuo. The residue was purified by pre-TLC (pretrolem.ether:EtOAc=1:2) to provide the title compound. MS: 366.2 (M+1). $^1$H NMR (400 MHz, $CDCl_3$): δ 7.34-7.39 (5H, m), 7.14 (1H, d, J=8.0 Hz), 6.87-6.91 (m, 2H), 5.17-5.21 (2H, m), 5.07 (4H, s), 4.83-4.88 (1H, m), 3.75-3.99 (1H, m), 3.10-3.20 (1H, m), 2.80-3.00 (1H, m), 1.95-2.10 (1H, m,), 1.55-1.60 (1H, m), 1.45-1.50 (1H, m), 0.94-0.98 (1H, m), 0.77-0.80 (1H, m).

Step 5: 5-((1,3-dihydroisobenzofuran-5-yl)oxy)-2-azabicyclo[4.1.0]heptane

To a solution of benzyl 5-((1,3-dihydroisobenzofuran-5-yl)oxy)-2-azabicyclo[4.1.0]heptane-2-carboxylate (700 mg, 1.916 mmol) in THF (10 mL) were added TEA (0.120 mL, 0.862 mmol) and palladium(II) chloride (23.78 mg, 0.134 mmol), triethylsilane (891 mg, 7.66 mmol). The reaction mixture was stirred at 20° C. for 1 h. 10 mL of MeOH was added to the mixture and the reaction mixture was filtered. The filtrate was concentrated in vacuo to provide the title compound, which was used directly in the next step. MS: 232.1 (M+1).

Step 6: Methyl 2-cyano-6-(5-((1,3-dihydroisobenzofuran-5-yl)oxy)-2-azabicyclo[4.1.0]heptan-2-yl)-4,5-dimethylnicotinate To a solution of compound 5-((1,3-dihydroisobenzofuran-5-yl)oxy)-2-azabicyclo[4.1.0]heptane (500 mg, 1.081 mmol) in DMF (3 mL) was added methyl 6-chloro-2-cyano-4,5-dimethylnicotinate (intermediate A2, 243 mg, 1.081 mmol) and DIEA (0.189 mL, 1.081 mmol), and the mixture was stirred at 65° C. for 16 h. The reaction mixture was quenched with water (10 mL), and extracted with EtOAc (10 mL×3). The combined organic layer was washed with brine, dried over anhydrous sodium suflate, filtered and concentrated to give a residue. The residue was further purified by flash silica gel chromatography (ISCO®; 4 g SepaFlash® Silica Flash Column, Eluent of 0-50% EtOAc/Pet.ether gradient @ 30 mL/min) to provide the title compound. MS: 420.0 (M+1).

Step 7: 2-(5-((1,3-dihydroisobenzofuran-5-yl)oxy)-2-azabicyclo[4.1.0]heptan-2-yl)-3,4-dimethyl-6,7-dihydro-5H-pyrrolo[3,4-b]pyridin-5-one To a mixture of methyl 2-cyano-6-(5-((1,3-dihydroisobenzofuran-5-yl)oxy)-2-azabicyclo[4.1.0]heptan-2-yl)-4,5-dimethylnicotinate (70 mg, 0.167 mmol) and cobalt (II) chloride (65.0 mg, 0.501 mmol) in methanol (5 mL) was added NaBH$_4$ (37.9 mg, 1.001 mmol) and the mixture was stirred at 20° C. for 1 h. The mixture was filtered and the filter cake was washed with methanol (10 mL×2). The filtrate was concentrated in vacuo and the residue was suspended in methanol (5 mL). Then TEA (0.047 mL, 0.334 mmol) was added to the mixture, and the resulting mixture was stirred at 20° C. for 1 h. The mixture was concentrated to give a residue, which was further purified by prep-TLC (Petrolem.ether:THF=1:1) to provide the title compound. MS: 392.2 (M+1). $^1$H NMR (400 MHz, CDCl$_3$): δ 7.15 (1H, d, J=8.4 Hz), 6.89-6.93 (2H, m), 5.89 (1H, s), 5.08-5.09 (4H m), 4.93-5.00 (1H, m), 4.26 (2H, s), 3.80-3.83 (1H, m), 3.06-3.12 (1H, m), 2.94-3.02 (1H, m), 2.66 (3H, s), 2.36 (3H, s), 2.17-2.21 (1H, s), 1.71-1.74 (2H, m), 0.95-1.04 (1H, m), 0.80-0.84 (1H, m).

The following examples in Table 4 were prepared according to Scheme 5 following the procedure outlined in the synthesis of Example 21 using an appropriate ArOH in step 1 and either intermediate A1 or A2 in step 6.

TABLE 4

| Ex | Structure | Name | MS (M + 1) | $^1$H NMR |
|---|---|---|---|---|
| 28 | 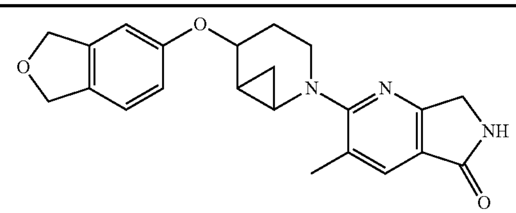 | 2-(5-((1,3-dihydroisobenzofuran-5-yl)oxy)-2-azabicyclo[4.1.0]heptan-2-yl)-3-methyl-6,7-dihydro-5H-pyrrolo[3,4-b]pyridin-5-one | 378.1 | (400 MHz, CDCl$_3$): δ 7.76 (1 H, s), 7.15 (1H d, J = 8.4 Hz), 6.89-6.93 (2 H, m), 5.85 (1 H, brs), 5.08-5.09 (4 H, m), 4.85-5.00 (1 H, m), 4.31 (2H, s), 4.02-4.06 (1 H, m), 3.75-3.80 (1 H, m), 3.00-3.10 (2 H, m), 2.50 (3 H, s), 2.17-2.20 (1 H, m), 1.74-1.76 (1 H, m), 0.97-1.02 (1 H, m), 079-0.83 (1 H, m). |
| 29 | 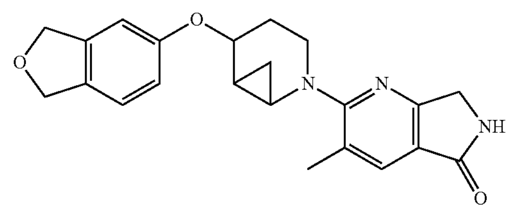 [SMILES: Cc1cc2c(nc1N1CCC(Oc3ccc4c(c3)COC4)C3CC31)CNC2=O] | 2-(5-((1,3-dihydroisobenzofuran-5-yl)oxy)-2-azabicyclo[4.1.0]heptan-2-yl)-3-methyl-6,7-dihydro-5H-pyrrolo[3,4-b]pyridin-5-one | 378.1 | (400 MHz, CDCl$_3$): δ 7.76 (1 H, s), 7.15 (1 H, d, J = 8.0 Hz), 6.85-6.93 (3 H, m), 5.08-5.09 (4 H, m), 4.85-5.00 (1 H, m), 4.31 (2 H s), 4.02-4.06 (1 H, m), 3.75-3.80 (1 H, m), 3.00-3.10 (2 H, m), 2.50 (3 H, s), 2.17-2.20 (1 H, m), 1.74-1.76 (1 H, m), 0.97-1.02 (1 H, m), 0.79-0.83 (1 H, m). |
| 30 | 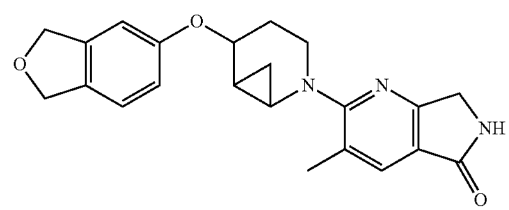 [SMILES: Cc1cc2c(nc1N1CCC(Oc3ccc4c(c3)COC4)C3CC31)CNC2=O] | 2-(5-((1,3-dihydroisobenzofuran-5-yl)oxy)-2-azabicyclo[4.1.0]heptan-2-yl)-3-methyl-6,7-dihydro-5H-pyrrolo[3,4-b]pyridin-5-one | 378.0 | (400 MHz, CDCl$_3$): δ 7.76 (1 H, s), 7.15 (1 H, d, J = 8.0 Hz), 7.01 (1 H, brs), 6.89-6.93 (2 H, m), 5.08-5.09 (4 H m), 4.85-5.00 (1 H, m), 4.31 (2 H, s), 4.02-4.06 (1 H, m), 3.75-3.80 (1 H, m), 3.00-3.10 (2 H, m), 2.50 (3 H s), 2.17-2.20 (1 H, m), 1.74-1.76 (1 H, m), 0.97-1.02 (1 H, m), 0.79-0.83 (1 H, m). |
| 31 | 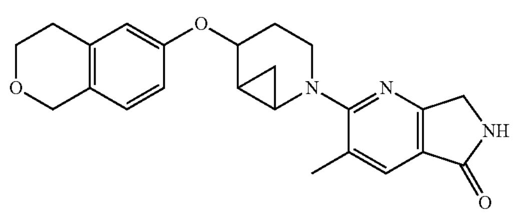 [SMILES: Cc1cc2c(nc1N1CCC(Oc3ccc4c(c3)CCOC4)C3CC31)CNC2=O] | 2-(5-(isochroman-6-yloxy)-2-azabicyclo[4.1.0]heptan-2-yl)-3-methyl-6,7-dihydro-5H-pyrrolo[3,4-b]pyridin-5-one | 392.1 | (400 MHz, CDCl$_3$): δ 7.46 (1 H, s), 7.23-7.26 (1 H, brs), 6.91 (1 H, m, J = 8.0 Hz), 6.83 (1 H, m, J = 2.4 Hz), 6.77 (1 H, s), 4.94-4.99 (1 H, m), 4.73 (2 H, s), 4.36 (2 H, s), 4.03-4.06 (1 H, m), 3.96 (2 H, t, J = 11.6 Hz), 3.04-3.09 (2 H, m), 2.83 (2 H, t, J = 10.8 Hz), 2.51 (3 H s), 2.31-2.42 (1 H, m), 1.76-1.78 (1 H, m), 1.62-1.65 (1 H, m), 1.01-1.03 (1 H, m), 0.80-0.82 (1 H, m). |
| 32 | 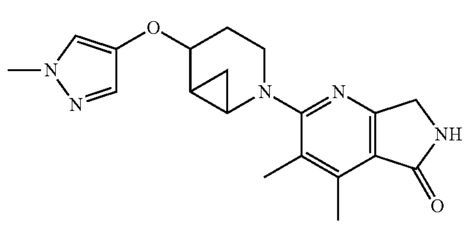 [SMILES: Cc1c(N2CCC(Oc3cnn(C)c3)C3CC32)nc2c(c1C)C(=O)NC2] | 3,4-dimethyl-2-(5-((1-methyl-1H-pyrazol-4-yl)oxy)-2-azabicyclo[4.1.0]heptan-2-yl)-6,7-dihydro-5H-pyrrolo[3,4-b]pyridin-5-one | 354.1 | (CDCl$_3$, 400 MHz): δ 7.29 (1 H, s), 7.14 (1 H, s), 5.79 (1 H, s), 4.54-4.62 (1 H, m), 4.23 (2 H, d, J = 4.0 Hz), 3.83 (3 H, s), 3.74-3.82 (1 H, m), 2.98-3.16 (1 H, m), 2.90-2.96 (1 H, m), 2.65 (3 H, s), 2.34 (3 H, s), 1.62-1.70 (2 H, m), 0.94-1.02 (1 H, m), 0.75-0.82 (1 H, m). |

TABLE 4-continued

| Ex | Structure | Name | MS (M + 1) | ¹H NMR |
|---|---|---|---|---|
| 33 | 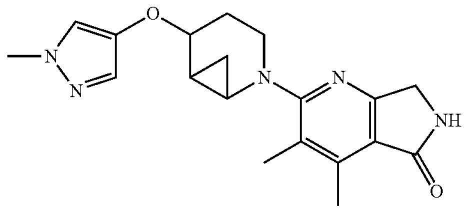 [SMILES: Cc1c(N2CCC(Oc3cnn(C)c3)C3CC32)nc2c(c1C)C(=O)NC2] | 3,4-dimethyl-2-(5-((1-methyl-1H-pyrazol-4-yl)oxy)-2-azabicyclo[4.1.0]heptan-2-yl)-6,7-dihydro-5H-pyrrolo[3,4-b]pyridin-5-one | 354.1 | (CDCl₃, 400 MHz): δ 7.30 (1 H, s), 7.15 (1 H, s), 5.99 (1 H, s), 4.54-4.65 (1 H, m), 4.26 (2 H, d, J = 4.4 Hz), 3.84 (3 H, s), 3.75-3.83 (1 H, m), 2.99-3.17 (1 H, m), 2.91-2.97 (1 H, m), 2.65 (3 H, s), 2.35 (3 H, s), 1.62-1.72 (2 H, m), 0.94-1.04 (1 H, m), 0.75-0.85 (1 H, m). |
| 34 | 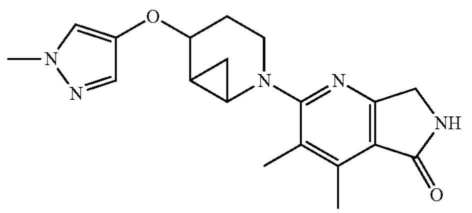 [SMILES: Cc1c(N2CCC(Oc3cnn(C)c3)C3CC32)nc2c(c1C)C(=O)NC2] | 3,4-dimethyl-2-(5-((1-methyl-1H-pyrazol-4-yl)oxy)-2-azabicyclo[4.1.0]heptan-2-yl)-6,7-dihydro-5H-pyrrolo[3,4-b]pyridin-5-one | 354.1 | (CDCl₃, 400 MHz): δ 7.30 (1 H, s), 7.15 (1 H, s), 6.08 (1H, s), 4.54-4.65 (1 H, m), 4.20-4.32 (2 H, m), 3.84 (3 H, s), 3.75-3.83 (1 H, m), 2.99-3.17 (1 H, m), 2.91-2.97 (1 H, m), 2.65 (3 H, s), 2.35 (3 H, s), 1.62-1.72 (2 H, m), 0.94-1.04 (1 H, m), 0.75-0.85 (1 H, m). |
| 35 | 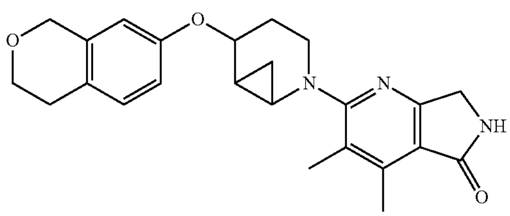 [SMILES: Cc1c(N2CCC(Oc3ccc4c(c3)COCC4)C3CC32)nc2c(c1C)C(=O)NC2] | 2-(5-(isochroman-7-yloxy)-2-azabicyclo[4.1.0]heptan-2-yl)-3,4-dimethyl-6,7-dihydro-5H-pyrrolo[3,4-b]pyridin-5-one | 406.1 | (400 MHz, CDCl₃): δ 7.00-7.10 (1 H, d, J = 8.4 Hz), 6.80-6.90 (1 H, m), 6.60-6.65 (1 H, d, J = 2.4 Hz), 5.80 (1 H, s), 4.85-4.95 (1 H, m), 4.65-4.75 (2 H, m), 4.15-4.30 (2 H, m), 3.90-4.00 (2 H, m), 3.70-3.80 (1 H, m), 3.00-3.15 (1 H, m), 2.85-2.90 (1 H, m), 2.64 (3 H, s), 2.35 (3 H, s), 2.10-2.20 (1 H, m), 1.65-1.75 (2 H, m), 1.25-1.30 (1 H, m), 0.90-1.00 (1 H, m), 0.75-0.80 (1 H, m). |
| 36 | 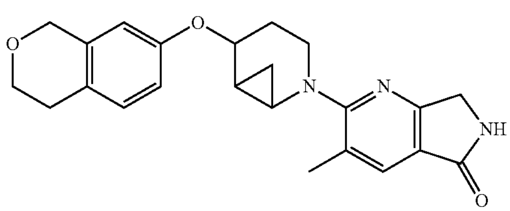 [SMILES: Cc1cc2c(nc1N1CCC(Oc3ccc4c(c3)COCC4)C3CC31)CNC2=O] | 2-(5-(isochroman-7-yloxy)-2-azabicyclo[4.1.0]heptan-2-yl)-3-methyl-6,7-dihydro-5H-pyrrolo[3,4-b]pyridin-5-one | 392.0 | (400 MHz, MeOD): δ 7.70-7.75 (1 H, d, J = 5.2 Hz), 7.00-7.10 (1 H, d, J = 8.4 Hz), 6.80-6.85 (1 H, m), 6.65-6.70 (1 H, m), 5.00-5.10 (1 H, m), 4.70 (2 H, s), 4.29 (2 H, s), 4.00-4.10 (1 H, m), 3.90-3.95 (2 H, m), 3.10-3.20 (1 H, m), 3.00-3.05 (1 H, m), 2.70-2.75 (2 H, m), 2.52 (3 H, s), 2.10-2.20 (1 H, m), 1.75-1.85 (1 H, m), 1.50-1.70 (1 H, m), 0.85-0.95 (1 H, m), 0.60-0.70 (1 H, m). |

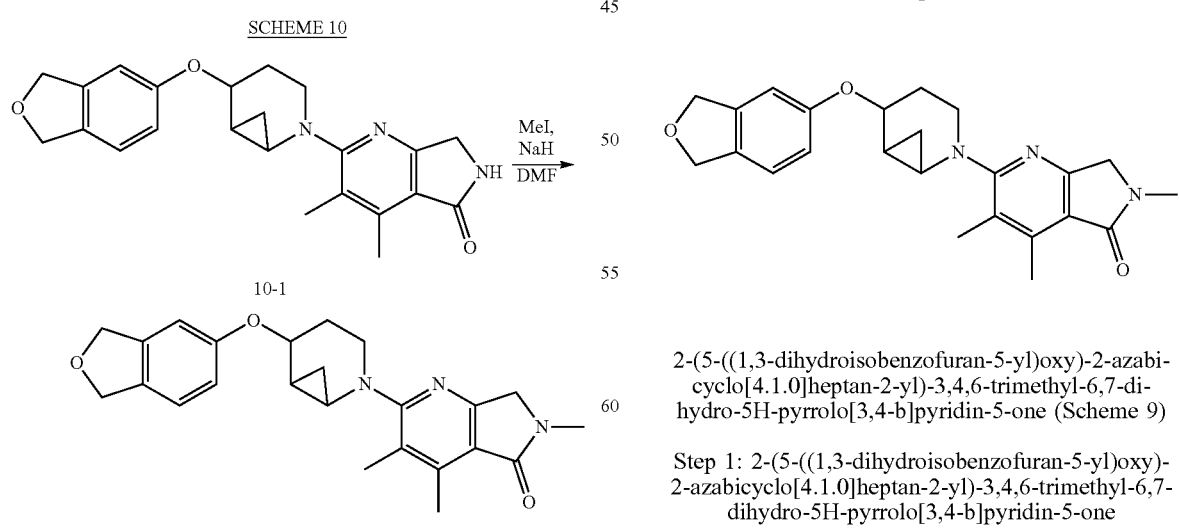

Example 37

2-(5-((1,3-dihydroisobenzofuran-5-yl)oxy)-2-azabicyclo[4.1.0]heptan-2-yl)-3,4,6-trimethyl-6,7-dihydro-5H-pyrrolo[3,4-b]pyridin-5-one (Scheme 9)

Step 1: 2-(5-((1,3-dihydroisobenzofuran-5-yl)oxy)-2-azabicyclo[4.1.0]heptan-2-yl)-3,4,6-trimethyl-6,7-dihydro-5H-pyrrolo[3,4-b]pyridin-5-one To a solution of 2-(5-((1,3-dihydroisobenzofuran-5-yl)oxy)-2-azabicyclo[4.1.0]-heptan-2-yl)-3,4-dimethyl-6,7-dihydro-5H-pyrrolo[3,4-b]pyridin-5-one (Example 27 compound, 30 mg, 0.077 mmol) in DMF (3 mL) was added NaH (6.13 mg, 0.153 mmol). The reaction mixture was stirred at 20° C. for 30 min. Then iodomethane (5.25 μl, 0.084 mmol) was added to the mixture and the reaction was stirred at 20° C. for 1 h. To the reaction was added saturated ammonium chloride (5 mL) and the mixture was extracted with ethyl acetate (15 mL×3). The combined organic layers were washed with brine (5 mL×2), dried over sodium sulfate, and filtered. The filtrate was concentrated in vacuo to give a residue, which was purified by prep-HPLC (TFA) to provide the title compound. MS: 406.1 (M+1), HNMR (400 MHz, MeOD): δ 7.16 (1H, d, J=8.0 Hz), 6.89-6.93 (2H, m), 5.08-5.09 (4H, m), 4.95-4.97 (1H, m), 4.25-4.40 (2H, m), 3.71-3.74 (1H, m), 3.31-3.34 (1H, m), 3.17 (3H, s), 2.95-2.98 (1H, m), 2.71 (3H, s), 2.41 (3H, s), 2.21-2.25 (1H, m), 1.71-1.83 (2H, m), 1.08-1.11 (1H, m), 0.95-0.97 (1H, m).

9-hydroxy-3,4,9-trimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one (Scheme 11)

Step 1: 3,4-dimethyl-2-(5-((1-methylcyclopropyl)methoxy)-2-azabicyclo[4.1.0]heptan-2-yl) 7,8,10,10a-tetrahydropyrido[2,3-a]indolizine-5,9-dione To a solution of 9-hydroxy-3,4-dimethyl-2-(5-((1-methylcyclopropyl)-methoxy)-2-azabicyclo[4.1.0]heptan-2-yl)-8,9,10,10a-tetrahydropyrido[2,3-a]indolizin-5(7H)-one (Example 21 compound, 40 mg, 0.097 mmol) in DCM (1 mL) was added Dess-Martin Periodinane (41.2 mg, 0.097 mmol) at 25° C. After addition, the mixture was stirred for 16 h. The reaction was filtered and the filtrate was concentrated in vacuo. The residue was purified by Prep-TLC (SiO₂, petroleum ether:ethyl acetate=1:2) to give the title compound. MS: 410.2 (M+H).

Step 2: 9-hydroxy-3,4,9-trimethyl-2-(5-((1-ethylcyclopropyl)methoxy)-2-azabicyclo[4.1.0]heptan-2-yl)-8,9,10,10a-tetrahydropyrido[2,3-a]indolizin-5(7H)-one To a solution of 3,4-dimethyl-2-(5-((1-methylcyclopropyl)methoxy)-2-azabicyclo[4.1.0]heptan-2-yl)-7,8,10,10a-tetrahydropyrido[2,3-a]indolizine-5,9-dione (60 mg, 0.147 mmol) in THF (3 mL) was added methylmagnesium bromide (0.098 ml, 0.293 mmol) at 0° C. Then the mixture reaction was stirred at 0° C. for 2 h. The reaction mixture was quenched with NH₄Cl (5 mL), then the mixture was extracted with EtOAc (10 mL×3). The combined organic layers were washed with water (5 mL×2), brine (5 mL), dried over anhydrous Na₂SO₄, filtered and concentrated to get the residue, which was further purified by Prep-TLC (SiO₂, petroleum ether:ethyl acetate=1:3) and Prep-HPLC (TFA) to give the title compound. MS: 426.3 (M+H), ¹H NMR (400 MHz, MeOD): □ 4.85-4.90 (1H, m), 4.40-4.45 (1H, m), 4.10-4.20 (2H, m), 3.70-3.80 (1H, m), 3.45-3.50 (1H, m), 3.30-3.35 (1H, m), 2.90-3.10 (2H, m), 2.60 (3H, s), 2.34 (3H, s), 2.25-2.30 (1H, m), 1.90-2.00 (1H, m), 1.70-1.75 (1H, m), 1.55-1.75 (1H, m), 1.40-1.50 (2H, m), 1.30-1.35 (1H, m), 1.10-1.25 (3H, m), 0.75-0.90 (4H, m), 0.50-0.55 (1H, m), 0.40-0.45 (2H, m), 0.30-0.35 (2H, m).

SCHEME 11

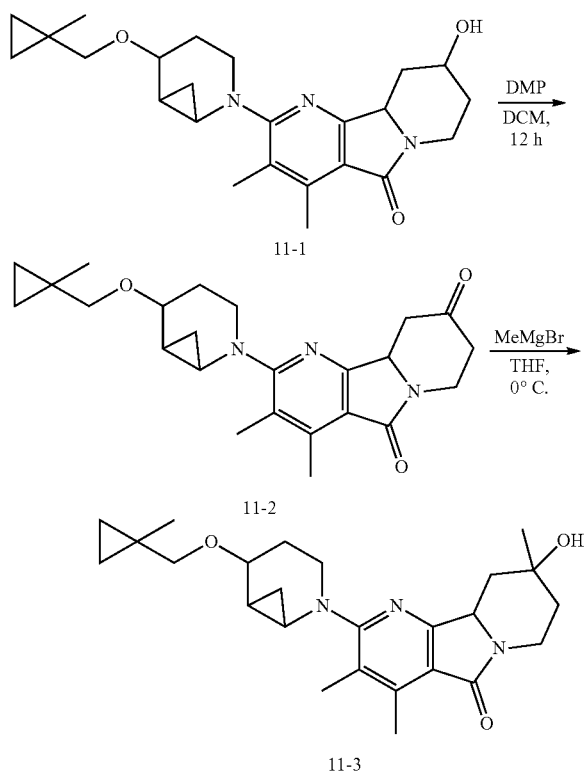

Example 38

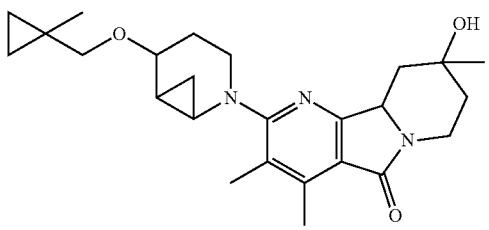 [SMILES: Cc1c(N2CCC(OCC3(C)CC3)C3CC32)nc2c(c1C)C(=O)N1CCC(C)(O)CC21]

SCHEME 12

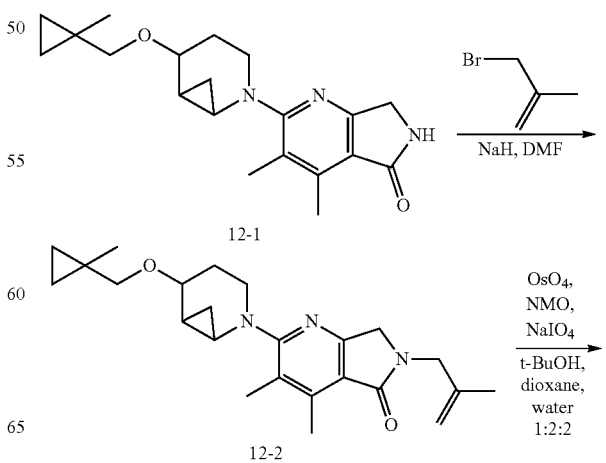

-continued

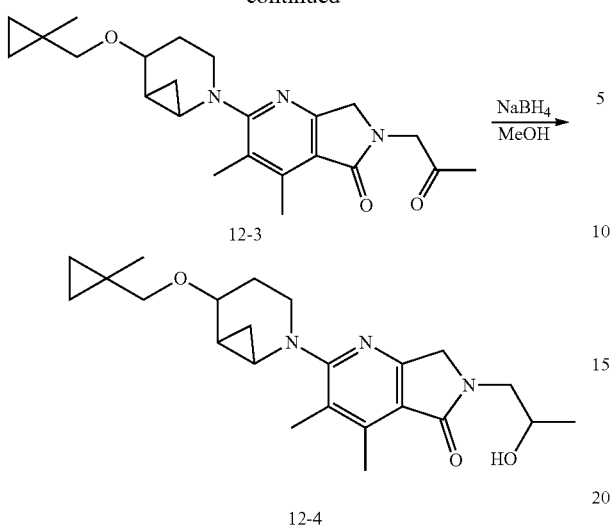

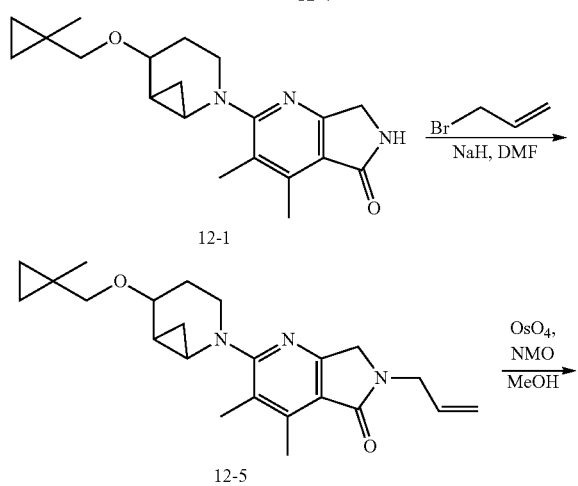

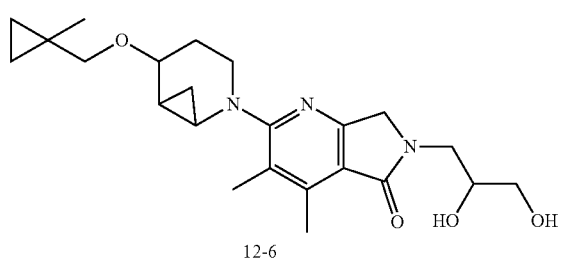

Example 39

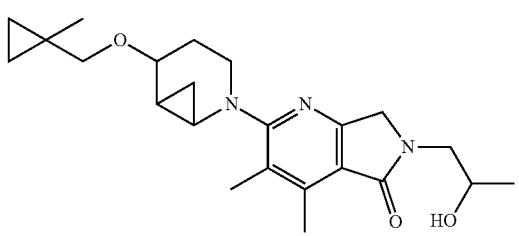 [SMILES: Cc1c(N2CCC(OCC3(C)CC3)C3CC32)nc2c(c1C)C(=O)N(CC(C)O)C2]

6-(2-hydroxypropyl)-3,4-dimethyl-2-(5-((1-methyl-cyclopropyl)methoxy)-2-azabicyclo[4.1.0]heptan-2-yl)-6,7-dihydro-5H-pyrrolo[3,4-b]pyridin-5-one (Scheme 12)

Example 40

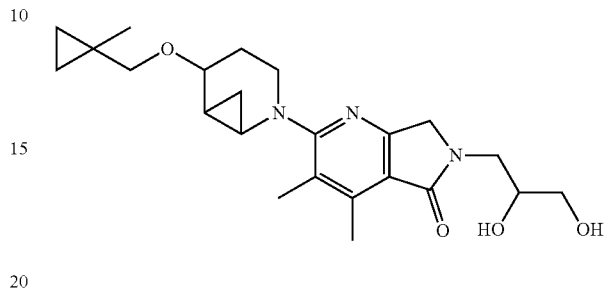

6-(2,3-dihydroxypropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Scheme 12)

Step 1: 3,4-dimethyl-6-(2-methylallyl)-2-(5-((1-methylcyclopropyl)methoxy)-2-azabicyclo[4.1.0]heptan-2-yl)-6,7-dihydro-5H-pyrrolo[3,4-b]pyridin-5-one To a solution of 3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (20 mg, 0.059 mmol) in DMF (0.5 mL) was added NaH (3.05 mg, 0.076 mmol) and the mixture was stirred at 0° C. for 1 h, then to the mixture was added 3-bromo-2-methylprop-1-ene (0.00768 mL, 0.076 mmol) in DMF (0.2 mL). The reaction was stirred at 25° C. for 3 h. The reaction mixture was quenched with NH₄Cl (5 mL), and extracted with EtOAc (3 mL×3). The combined organic layers were washed with brine (5 mL), dried over anhydrous Na₂SO₄ and filtered. The filtrate was concentrated to get the residue, which was further by prep-TLC (EtOAc/Pet. ether=1:1) to give the title compound. MS: 396.1 (M+H).

Step 2: 3,4-dimethyl-2-(5-((1-methylcyclopropyl)methoxy)-2-azabicyclo[4.1.0]heptan-2-yl)-6-(2-oxopropyl)-6,7-dihydro-5H-pyrrolo[3,4-b]pyridin-5-one To a solution of 3,4-dimethyl-6-(2-methylallyl)-2-(5-((1-methylcyclopropyl)-methoxy)-2-azabicyclo[4.1.0]heptan-2-yl)-6,7-dihydro-5H-pyrrolo[3,4-b]pyridin-5-one (10 mg, 0.025 mmol) in 1,4-Dioxane (1.500 mL), t-BuOH (0.75 mL) and water (1.500 mL) were added NMO (3.55 mg, 0.030 mmol) and osmium tetroxide (1.928 mg, 7.58 μmol). The mixture was stirred at 25° C. for 20 min, then to the mixture was added sodium periodate (27.0 mg, 0.126 mmol). The reaction was stirred at 25° C. for 20 min. The reaction mixture was quenched with water (5 mL) and then the mixture was extracted with EtOAc (3 mL×3). The combined organic layers were washed with brine (10 mL), dried over anhydrous Na₂SO₄ and filtered. The filtrate was concentrated to give the title compound, which was used to the next step directly.

Step 3: 6-(2-hydroxypropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of 3,4-dimethyl-2-(5-((1-methylcyclopropyl)methoxy)-2-azabicyclo[4.1.0]heptan-2-yl)-6-(2-oxopropyl)-6,7-dihydro-5H-pyrrolo[3,4-b]pyridin-5-one in MeOH (0.5 mL) was added NaBH$_4$ and the mixture was stirred at 25° C. for 0.5 h. The reaction mixture was quenched with water (5 mL) and then the mixture was extracted with EtOAc (3 mL×3). The combined organic layers were washed with brine (10 mL), dried over anhydrous Na$_2$SO$_4$ and filtered. The filtrate was concentrated to get the residue, which was further purified by prep-HPLC (NEU) to give the title compound. MS: 400.2, (M+H), $^1$HNMR (CDCl$_3$, 400 MHz): δ 4.24-4.33 (2H, m), 4.04-4.14 (2H, m), 3.72 (1H, d, J=12.8 Hz), 3.56-3.62 (2H, m) 3.40-3.46 (1H, m), 3.28-3.34 (1H, m), 2.97 (1H, t, J=12.4 Hz), 2.84-2.91 (1H, s), 2.63 (3H, m), 2.33 (3H, m), 2.05 (1H, m), 1.98-2.04 (1H, m), 1.48-1.54 (1H, m), 1.26 (4H, d, J=6.14 Hz), 1.16 (3H, m), 0.88-0.96 (1H, m), 0.65-0.71 (1H, m), 0.42 (2H, m), 0.35 (2H, m).

Step 4: 6-allyl-3,4-dimethyl-2-(5-((1-methylcyclopropyl)methoxy)-2-azabicyclo[4.1.0]-heptan-2-yl)-6,7-dihydro-5H-pyrrolo[3,4-b]pyridin-5-one To a solution of 3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (100 mg, 0.293 mmol) in DMF (1.5 ml) was added NaH (15.23 mg, 0.381 mmol) at 0° C. and the mixture stirred for 0.5 h. Then to the mixture was added 3-bromoprop-1-ene (46.1 mg, 0.381 mmol) in THF (1 ml). The reaction was stirred at 25° C. for 16 h. The reaction mixture was quenched with water (8 mL) and then the mixture was extracted with EtOAc (5 mL×3). The combined organic layers were washed with brine (15 mL), dried over anhydrous Na$_2$SO$_4$ and filtered. The filtrate was concentrated to get the residue, which was further purified by prep-TLC (Pet. ether/EtOAc 1:1) to give the title compound. MS: 382.3 (M+H).

Step 5: 6-(2,3-dihydroxypropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one To a solution of 6-allyl-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (34 mg, 0.089 mmol) in MeOH (1 mL) were added NMO (15.66 mg, 0.134 mmol) and osmium tetroxide (2.266 mg, 8.91 μmol) and the mixture was stirred at 25° C. for 16 h. The reaction mixture was quenched with Na$_2$SO$_3$ and then the mixture was extracted with EtOAc (5 mL×3). The combined organic layers were washed with brine (10 mL), dried over anhydrous Na$_2$SO$_4$ and concentrated to get the residue, which was further purified by prep-TLC (EtOAc) to give the title compound. MS: 416.1 (M+H). $^1$HNMR (CDCl$_3$, 400 MHz): δ 4.21-4.40 (2H, m), 4.02-4.11 (1H, m), 3.89-3.97 (1H, m), 3.67-3.77 (3H, m), 3.60 (3H, s), 3.39-3.46 (1H, m), 3.28-3.32 (1H, m), 2.96 (1H, t, J=13.2 Hz), 2.84-2.92 (1H, m), 2.61 (3H, s), 2.33 (3H, s), 1.96-2.06 (1H, m), 1.44-1.61 (2H, m), 1.26 (1H, s), 1.15 (3H, m), 0.88-0.97 (1H, m), 0.63-0.71 (1H, m), 0.41 (2H, s), 0.35 (2H, s).

SCHEME 13

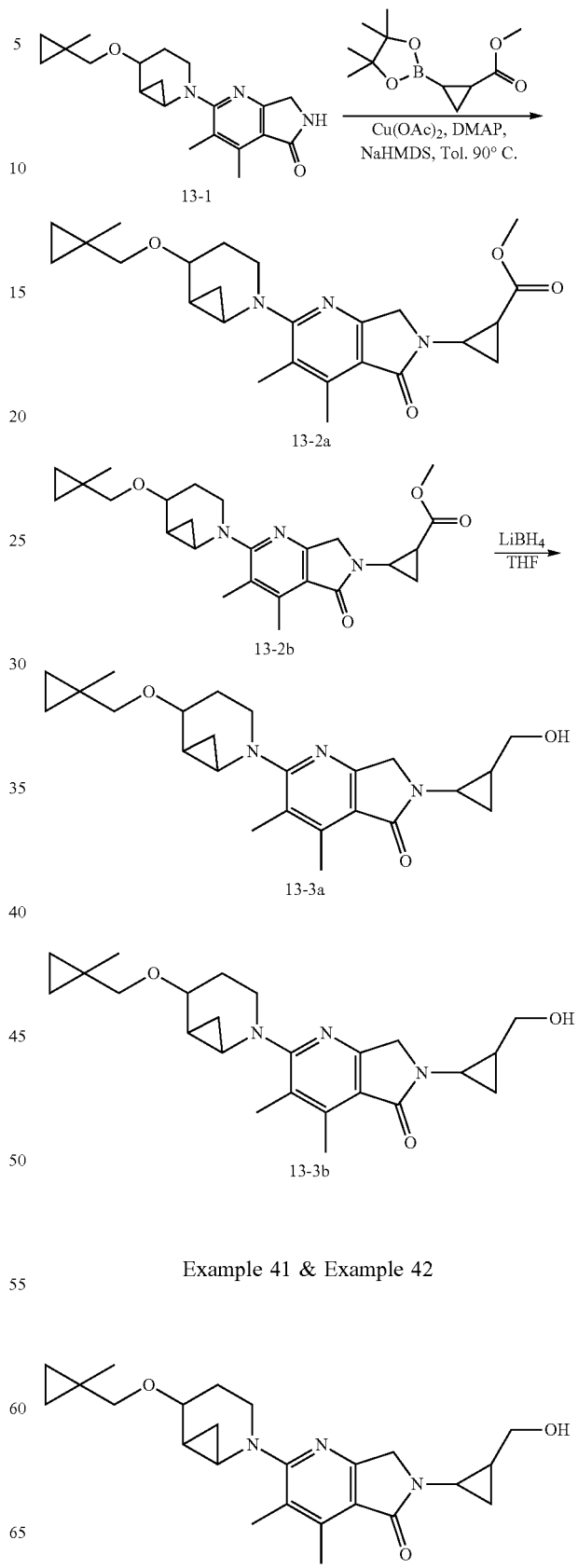

Example 41 & Example 42

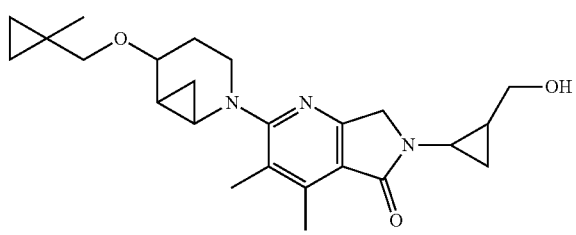

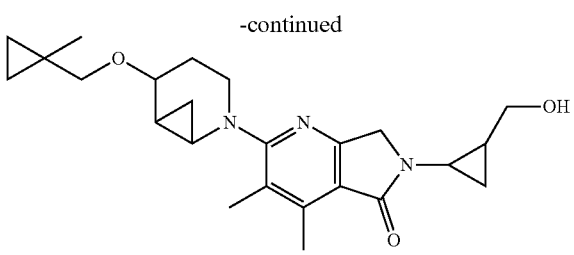

6-(2-(hydroxymethyl)cyclopropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (Scheme 13)

Step 1: Methyl 2-(3,4-dimethyl-2-(5-((1-methylcyclopropyl)methoxy)-2-azabicyclo[4.1.0]-heptan-2-yl)-5-oxo-5,7-dihydro-6H-pyrrolo[3,4-b]pyridin-6-yl)cyclopropane-1-carboxylate To a solution of 3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one (100 mg, 0.293 mmol) in toluene (2 mL) was added DMAP (107 mg, 0.879 mmol), methyl 2-(4,4,5,5-tetramethyl-1,3,2-dioxaborolan-2-yl)cyclopropanecarboxylate (132 mg, 0.586 mmol), diacetoxycopper (58.5 mg, 0.322 mmol) and sodium bis(trimethylsilyl)amide (0.322 mL, 0.322 mmol). The reaction was stirred at 90° C. for 15 h under 15 psi of O$_2$. The reaction was treated with ammonium hydroxide (10 mL), water (10 mL) was added, and the water phase was extracted with ethyl acetate (8 mL×3). The combined organic fractions were washed with water (8 mL×3) and brine (10 mL), dried (Na$_2$SO$_4$), filtered, and the solvent was evaporated under reduced pressure. The residue was purified by prep-TLC (Pet. ether/EtOAc=1:1) to give the two isomers. MS: 440.2 (M+H).

Step 2: 6-(2-(hydroxymethyl)cyclopropyl)-3,4-dimethyl-2-(5-((1-methylcyclopropyl)-methoxy)-2-azabicyclo[4.1.0]heptan-2-yl)-6,7-dihydro-5H-pyrrolo[3,4-b]pyridin-5-one To a solution of methyl 2-(3,4-dimethyl-2-(5-((1-methylcyclopropyl)methoxy)-2-azabicyclo[4.1.0]heptan-2-yl)-5-oxo-5,7-dihydro-6H-pyrrolo[3,4-b]pyridin-6-yl)cyclo-propane-1-carboxylate (38 mg, 0.086 mmol) in THF (1 mL) was added LiBH$_4$ (5.65 mg, 0.259 mmol) and the mixture was stirred at 25° C. for 16 h. The reaction mixture was quenched with water (8 mL). Then the mixture was extracted with EtOAc (5 mL×3) and the combined organic layers were washed with brine (10 mL), dried over anhydrous Na$_2$SO$_4$ and filtered. The filterate was concentrated to get the residue, which was further purified by prep-TLC (EtOAc) to give the title compound. Peak 1: MS: 412.2 (M+H). $^1$HNMR (CDCl$_3$, 400 MHz): δ 2.01-4.20 (3H, m), 3.93-4.00 (1H, m), 3.70 (1H, d, J=12.8 Hz), 3.39-3.44 (1H, m), 3.26-3.31 (1H, m), 3.20 (1H, t, J=10 Hz), 2.90-3.00 (1H, m), 2.81-2.88 (1H, m), 2.62-2.66 (1H, m), 2.60 (1H, s), 2.31 (3H, s), 1.96-2.05 (1H, m), 1.41-1.60 (3H, m), 1.14 (3H, s), 1.01-1.09 (1H, m), 0.82-0.95 (2H, m), 0.62-0.69 (1H, m), 0.40 (2H, s), 0.34 (2H, s). Peak 2: MS: 412.2 (M+H). $^1$HNMR (CDCl$_3$, 400 MHz): δ 4.50 (1H, d, J=12 Hz), 4.19-4.30 (1H, m), 4.96-4.17 (1H, m), 3.74 (1H, d, J=13.2), 3.37-3.46 (1H, m), 3.27-3.33 (1H, m), 2.84-3.02 (3H, m), 2.76-2.82 (1H, m), 2.62 (3H, s), 2.33 (3H, m), 1.96-2.07 (1H, m), 1.48-1.61 (2H, m), 1.56 (3H, s), 0.98-1.07 (1H, m), 0.88-0.97 (1H, m), 0.63-0.70 (1H, m), 0.43-0.49 (1H, m), 0.42 (2H, s), 0.35 (2H, s).

SCHEME 14

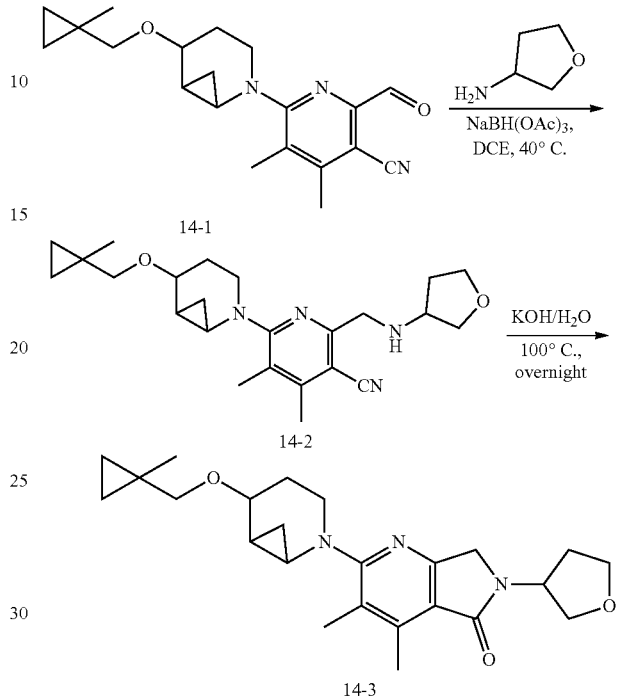

Example 43

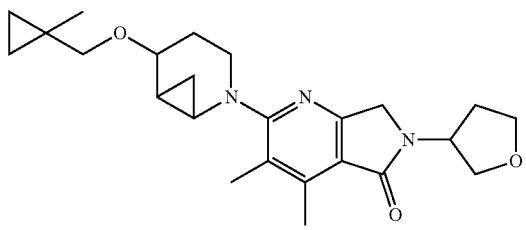 [SMILES: Cc1c(N2CCC(OCC3(C)CC3)C3CC32)nc2c(c1C)C(=O)N(C1CCOC1)C2]

3,4-dimethyl-2-(5-((1-methylcyclopropyl)methoxy)-2-azabicyclo[4.1.0]heptan-2-yl)-6-(tetrahydrofuran-3-yl)-6,7-dihydro-5H-pyrrolo[3,4-b]pyridin-5-one (Scheme 14)

Step 1: 4,5-dimethyl-6-(5-((1-methylcyclopropyl)methoxy)-2-azabicyclo[4.1.0]heptan-2-yl)-2-(((tetrahydrofuran-3-yl)amino)methyl)nicotinonitrile To a solution of 2-formyl-4,5-dimethyl-6-(5-((1-methylcyclopropyl)methoxy)-2-azabicyclo[4.1.0]heptan-2-yl)nicotinonitrile (compound 5-4 of Scheme 5, 100 mg, 0.295 mmol) in DCE (3 mL) was added tetrahydrofuran-3-amine (25.7 mg, 0.295 mmol) and AcOH (1.687 μL, 0.029 mmol), the mixture was stirred at 40° C. for 0.5 h. Then sodium triacetoxyborohydride (125 mg, 0.589 mmol) was added and the mixture was stirred at 40° C. for 16 h. The reaction mixture was quenched with saturated aqueous NaHCO₃ (~10 mL) and the mixture was extracted with EtOAc (10 mL×3). The combined organic layers were washed with brine, dried over anhydrous sodium sulfate, filtered and concentrated to get the residue, which was further purified by pre-TLC (DCM:MeOH=10:1) to give the title compound.

Step 2: 3,4-dimethyl-2-(5-((1-methylcyclopropyl)methoxy)-2-azabicyclo[4.1.0]heptan-2-yl)-6-(tetrahydrofuran-3-yl)-6,7-dihydro-5H-pyrrolo[3,4-b]pyridin-5-one To a solution of compound 4,5-dimethyl-6-(5-((1-methylcyclopropyl)-methoxy)-2-azabicyclo[4.1.0]heptan-2-yl)-2-(((tetrahydrofuran-3-yl)amino)methyl)-nicotinonitrile (125 mg, 0.304 mmol) in water (3 mL) and MeOH (0.5 mL) was added potassium hydroxide (512 mg, 9.13 mmol). The mixture was stirred at 100° C. for 16 h. The reaction mixture was quenched with 1N HCl to adjust to pH~7, then the mixture was extracted with EtOAc (10 mL×3) and the combined organic layers were washed with brine, dried over anhydrous sodium sulfate, filtered and concentrated to get the residue, which was further purified by pre-HPLC (neutral) to give the title compound. MS: 412.2 (M+H). ¹H NMR (500 MHz, CDCl₃): δ 5.13-5.14 (1H, m), 4.19-4.25 (2H, m), 4.00-1.10 (2H, m), 3.83-3.89 (3H, m), 3.70-3.72 (1H, m), 3.42 (1H, d, J=8.8 Hz), 3.31 (1H, d, J=10.0 Hz), 2.84-2.97 (2H, m), 2.64 (3H, s), 2.26-2.35 (4H, m), 1.90-2.05 (2H, m), 1.40-1.60 (2H, m), 1.70-1.81 (1H, m), 1.16 (3H, s), 0.90-0.95 (1H, m), 0.66-0.69 (1H, m), 0.35-0.42 (4H, m).

SCHEME 15

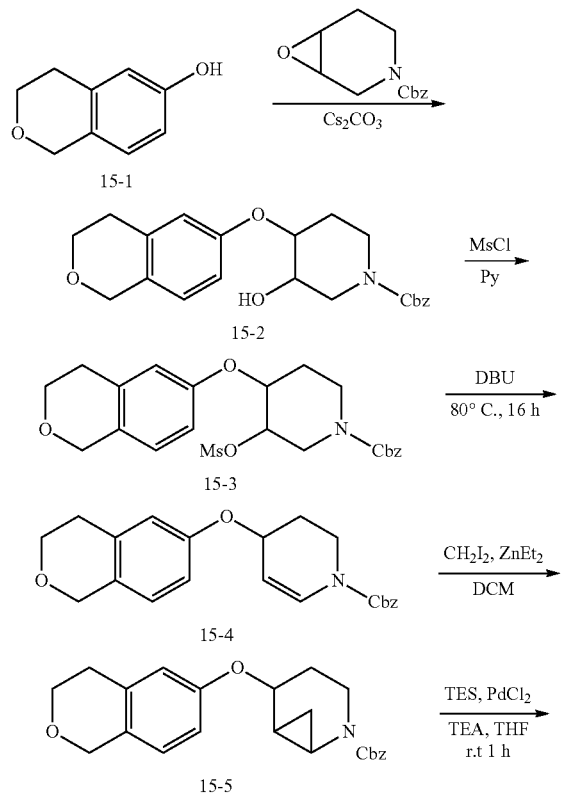

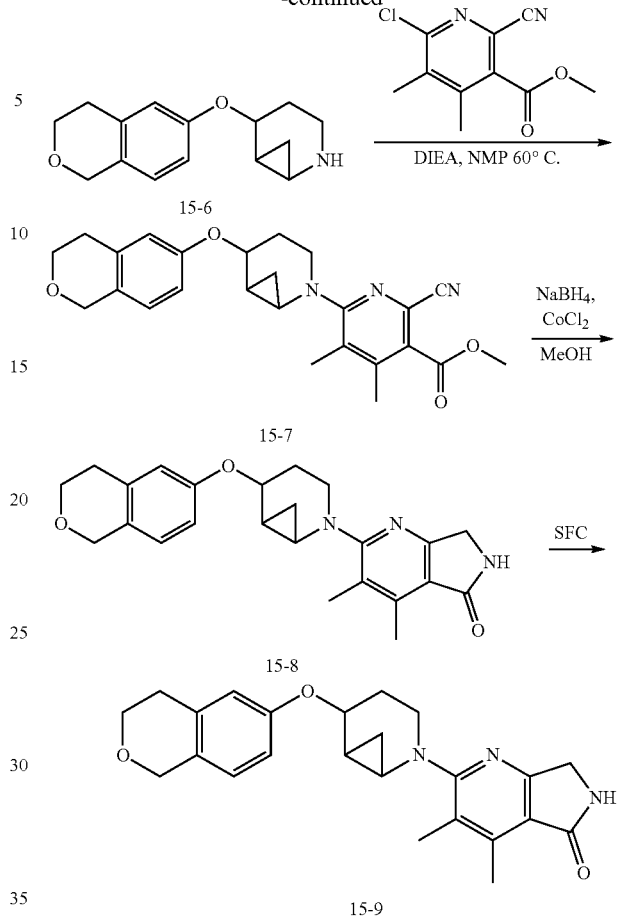

Example 44 & Example 45

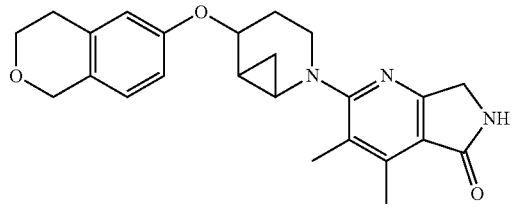 [SMILES: Cc1c(N2CCC(Oc3ccc4c(c3)CCOC4)C3CC32)nc2c(c1C)C(=O)NC2]

2-(5-(isochroman-6-yloxy)-2-azabicyclo[4.1.0]heptan-2-yl)-3,4-dimethyl-6,7-dihydro-5H-pyrrolo[3,4-b]pyridin-5-one (Scheme 15)

Step 1: Benzyl 3-hydroxy-4-(isochroman-6-yloxy)piperidine-1-carboxylate

A mixture of benzyl 7-oxa-3-azabicyclo[4.1.0]heptane-3-carboxylate (3.46 g, 14.83 mmol), isochroman-6-ol (2.2 g, 13.48 mmol) and Cs₂CO₃ (5.27 g, 16.17 mmol) in DMF (40 mL) was stirred at 80° C. for 16 hours. The mixture was diluted with EtOAc (80 mL), washed with water (100 mL), dried over Na₂SO₄, filtered and the filtrate was concentrated. The residue was purified by flash silica gel chromatography (ISCO®; 20 g SepaFlash® Silica Flash Column, Eluent of 0~45% THF/Pet.ether gradient @ 35 mL/min) to give the title compound. ¹H NMR (CDCl₃, 400 MHz): δ 7.30-7.42 (5H, m), 6.88-6.94 (1H, m), 6.75-6.80 (1H, m), 6.70-6.73 (1H, m), 5.16 (2H, s), 4.73 (2H, s), 4.03-4.25 (2H, m), 3.96 (2H, t, J=5.6 Hz), 3.07-3.36 (2H, m), 2.79-2.86 (2H, m), 2.38 (1H, s), 2.03-2.16 (1H, m).

Step 2: Benzyl 4-(isochroman-6-yloxy)-3-((methylsulfonyl)oxy)piperidine-1-carboxylate To a solution of benzyl 3-hydroxy-4-(isochroman-6-yloxy)piperidine-1-carboxylate (4.049 g, 10.56 mmol) in pyridine (40 mL) was added Ms-Cl (2.054 mL, 26.4 mmol) at 0° C. and the mixture was stirred at 20° C. for 16 hours. The mixture was dissolved in EtOAc (100 mL), washed with water (100 mL), saturated aqueous citric acid (50 mL×2), brine (50 ml), dried over Na₂SO₄, filtered and the filtrate was concentrated. The residue was purified by flash silica gel chromatography (ISCO®; 20 g SepaFlash® Silica Flash Column, Eluent of 0~40% EtOAc/Pet.ether gradient @ 35 mL/min) to give the title compound. ¹HNMR (CDCl₃, 400 MHz): δ 7.30-7.42 (5H, m), 6.90-6.95 (1H, m), 6.74-6.81 (1H, m), 6.68-6.74 (1H, m), 5.04-5.25 (2H, m), 4.72 (3H, s), 4.44-4.59 (1H, m), 3.95 (3H, t, J=6 Hz), 3.44-3.86 (3H, m), 2.99-3.09 (1H, m), 2.91 (1H, s), 2.77-2.85 (2H, m), 2.07-2.19 (1H, m), 1.74-1.84 (1H, m).

Step 3: Benzyl 4-(isochroman-6-yloxy)-3,4-dihydropyridine-1(2H)-carboxylate

A solution of benzyl 4-(isochroman-6-yloxy)-3-((methylsulfonyl)oxy)-piperidine-1-carboxylate (4.517 g, 9.79 mmol) in DBU (60 mL) was stirred at 80° C. for 16 h. The reaction mixture was quenched with water (200 mL), then the mixture was extracted with EtOAc (50 mL×3) The combined organic layers were washed with brine (50 mL), dried over anhydrous Na₂SO₄ and filtered. The filtrate was concentrated to get the residue, which was further purified by flash silica gel chromatography (ISCO®; 20 g SepaFlash® Silica Flash Column, Eluent of 0~12% EtOAc/Pet.ether gradient @ 80 mL/min) to give the title compound. ¹HNMR (CDCl₃, 400 MHz): δ 7.30-7.43 (5H, m), 6.88-6.93 (1H, m), 6.73-6.79 (1H, m), 6.68-6.71 (1H, m), 5.22 (2H, s), 5.08-5.21 (1H, m), 4.75-4.79 (1H, m), 4.73 (2H, s), 3.96 (3H, t, J=5.6 Hz), 3.48-3.62 (1H, m), 2.78-2.86 (2H, m), 2.09-2.22 (1H, m), 1.82-1.99 (1H, m).

Step 4: Benzyl 5-(isochroman-6-yloxy)-2-azabicyclo[4.1.0]heptane-2-carboxylate To a solution of diiodomethane (2.75 ml, 34.1 mmol) in DCM (10 mL) was added diethylzinc (34.1 ml, 34.1 mmol) at 0° C. and the mixture was stirred for 15 min. Then to the mixture was added benzyl 4-(isochroman-6-yloxy)-3,4-dihydropyridine-1(2H)-carboxylate (2.491 g, 6.82 mmol) in DCM (20 mL), and the reaction was stirred at 23° C. under N₂ atmosphere for 1 h. The reaction mixture was quenched with NH₄Cl (100 mL), and then the mixture was extracted with DCM (30 mL×3). The combined organic layers were dried over anhydrous sodium sulfate, filtered and concentrated to get the residue, which was further purified by flash silica gel chromatography (ISCO®; 20 g SepaFlash® Silica Flash Column, Eluent of 0~10% THF/PE gradient @ 60 mL/min) to give the title compound. MS: 380.2 (M+H). ¹HNMR (CDCl₃, 400 MHz): δ 7.30-7.44 (5H, m), 6.84-6.93 (1H, m), 6.79-6.83 (1H, m), 6.74-6.77 (1H, m), 5.13-5.24 (2H, m), 4.79-4.89 (1H, m), 4.71-4.76 (3H, m), 3.92-4.00 (4H, m), 3.08-3.21 (1H, m), 2.79-2.87 (3H, m), 1.95-2.11 (1H, m), 1.57-1.65 (2H, m), 1.45-1.54 (1H, m), 0.88-1.03 (1H, m), 0.73-0.82 (1H, m).

Step 5: 5-(isochroman-6-yloxy)-2-azabicyclo[4.1.0]heptane

To a solution of benzyl 5-(isochroman-6-yloxy)-2-azabicyclo[4.1.0]heptane-2-carboxylate (1.157 g, 3.05 mmol) in THF (2 mL) were added palladium(ii) chloride (54 mg, 0.305 mmol), TEA (0.191 mL, 1.372 mmol) and triethylsilane (1.948 mL, 12.20 mmol), then the mixture was stirred at 25° C. for 1 h. The mixture was filtered and concentrated to give 5-(isochroman-6-yloxy)-2-azabicyclo[4.1.0]heptane (0.748 g, 3.05 mmol, 100% yield) as brown oil, which was used directly to the next step. MS: 246.1 (M+H).

Step 6: Methyl 2-cyano-6-(5-(isochroman-6-yloxy)-2-azabicyclo[4.1.0]heptan-2-yl)-4,5-dimethylnicotinate To a solution of 5-(isochroman-6-yloxy)-2-azabicyclo[4.1.0]heptane (0.748 g, 3.05 mmol) in NMP (10 mL) were added methyl 6-chloro-2-cyano-4,5-dimethylnicotinate (0.479 g, 2.134 mmol) and DIEA (1.598 mL, 9.15 mmol) and the mixture was stirred at 65° C. for 16 h. The reaction mixture was quenched with water (100 mL), then the mixture was extracted with EtOAc (30 mL×3). The combined organic layers were washed with brine (80 mL), dried over anhydrous sodium sulfate and filtered. The filtrate was concentrated to get the residue, which was further purified flash silica gel chromatography (ISCO®; 12 g SepaFlash® Silica Flash Column, Eluent of 0~25% EtOAc/Pet.ether gradient @ 50 mL/min) to give the title compound. MS: 434.1 (M+H).

Step 7: 2-(5-(isochroman-6-yloxy)-2-azabicyclo[4.1.0]heptan-2-yl)-3,4-dimethyl-6,7-dihydro-5H-pyrrolo[3,4-b]pyridin-5-one To a solution of methyl 2-cyano-6-(5-(isochroman-6-yloxy)-2-azabicyclo[4.1.0]heptan-2-yl)-4,5-dimethylnicotinate (661 mg, 1.220 mmol) in MeOH (20 mL) was added cobalt(ii) chloride (475 mg, 3.66 mmol) and NaBH₄ (277 mg, 7.32 mmol). Then the mixture was stirred at 25° C. for 3 h. The reaction mixture was filtered and purified by prep-TLC (Pet. ether:EtOAc=1:2) to give the title compound. MS: 406.3 (M+H).

Step 8: 2-(5-(isochroman-6-yloxy)-2-azabicyclo[4.1.0]heptan-2-yl)-3,4-dimethyl-6,7-dihydro-5H-pyrrolo[3,4-b]pyridin-5-one 2-(5-(isochroman-6-yloxy)-2-azabicyclo[4.1.0]heptan-2-yl)-3,4-dimethyl-6,7-dihydro-5H-pyrrolo[3,4-b]pyridin-5-one (120 mg, 0.296 mmol) was resolved by SFC (AD(250 mm*30 mm, 10 um), 55% EtOH with 0.1% NH₃H₂O/CO₂ at 80 mL/min) to give the two isomers. Peak 1: MS 406.1 (M+H). ¹H NMR (400 MHz, MeOD): δ 6.90-6.94 (1H, m), 6.81-6.86 (1H, m), 6.76-6.79 (1H, m), 5.92 (1H, s), 4.91-4.99 (1H, m), 4.74 (2H, s), 4.25 (2H, d, J=4.0 Hz), 3.97 (2H, t, J=5.6 Hz), 3.78-3.84 (1H, m), 3.05-3.13 (1H, m), 2.92-2.98 (1H, m), 2.84 (2H, t, J=5.4 Hz), 2.66 (3H, s), 2.35 (3H, s), 2.15-2.21 (1H, m), 1.68-1.77 (2H, m), 1.50 (1H, d, J=7.0 Hz), 0.94-1.02 (1H, m), 0.79-0.85 (1H, m). Peak 2: MS 406.0 (M+H). ¹H NMR (400 MHz, MeOD): δ 6.90-6.94 (1H, m), 6.81-6.86 (1H, m), 6.76-6.79 (1H, m), 5.87 (1H, s), 4.91-4.99 (1H, m), 4.74 (2H, s), 4.25 (2H, d, J=4 Hz), 3.97 (2H, t, J=3.2 Hz), 3.78-3.84 (1H, m), 3.05-3.13 (1H, m), 2.92-2.98 (1H, m), 2.84 (2H, t, J=5.6 Hz), 2.66 (3H, s), 2.35 (3H, s), 2.15-2.21 (1H, m), 1.68-1.76 (2H, m), 1.50 (1H, d, J=6.8 Hz), 0.94-1.02 (1H, m), 0.79-0.85 (1H, m).

Assay Protocol

The utility of the compounds as M4 muscarinic receptor allosteric modulators may be demonstrated by methodology known in the art, including by the assay described herein.

CHO-K1 cells stably transfected with human M4 receptor and chimeric G-protein Gαqi5 are thawed from liquid $N_2$ storage, resuspended in growth medium, plated in black, clear bottom 384 well plates, and incubated 16-20 hours at 37° C., 5% $CO_2$.

On the day of assay, growth medium is removed, the cells are washed 2 times with wash buffer, and cells are incubated in dye loading buffer at 37° C., 5% $CO_2$ for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 5

| Example | M4 PAM IP (nM) |
| --- | --- |
| 1 | 39 |
| 2 | 1315 |
| 3 | 40 |
| 4 | 1674 |
| 5 | 117 |
| 6 | 711 |
| 7 | 659 |
| 8 | 3000 |
| 9 | 8088 |
| 10 | 47 |
| 11 | 742 |
| 12 | 506 |
| 13 | 58 |
| 13 | 960 |
| 15 | 50 |
| 16 | 1527 |
| 17 | 103 |
| 18 | 20200 |
| 20 | 12020 |
| 21 | 157 |
| 22 | 116 |
| 23 | 2348 |
| 24 | 2440 |
| 25 | 195 |
| 26 | 153 |
| 27 | 166 |
| 28 | 76 |
| 29 | 43 |
| 30 | 727 |
| 31 | 72 |
| 32 | 335 |
| 33 | 189 |

TABLE 5-continued

| Example | M4 PAM IP (nM) |
| --- | --- |
| 34 | 5941 |
| 35 | 281 |
| 36 | 156 |
| 37 | 143 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

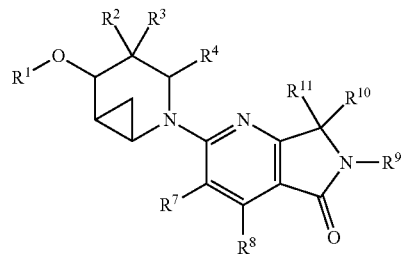

wherein:
$R^1$ is selected from:
(1) hydrogen;
(2) —$C_{1-6}$alkyl, which is unsubstituted or substituted with substituents selected from: hydroxy, fluoro, —CN, —O—$C_{1-6}$alkyl, $C_{3-6}$cycloalkyl, bicycle [1.1.1]pentane, tetrahydrofuranyl, phenyl, pyridyl, oxazolyl, —$NH_2$, —NH(—$C_{1-6}$alkyl), —N—$C_{1-6}$alkyl)$_2$, and —N(C=O)—$C_{1-6}$alkyl, wherein the $C_{1-6}$alkyl or $C_{3-6}$cycloalkyl is unsubstituted or substituted with substituents selected from: fluoro, cyano, $CF_3$, $C_{1-6}$ alkyl or —O—$C_{1-6}$alkyl;
(3) a phenyl, heteroaryl or heterocyclyl ring, wherein the phenyl, heteroaryl or heterocyclyl ring is substituted with one or more $R^{1a}$, $R^{1b}$ and $R^{1c}$, wherein $R^{1a}$, $R^{1b}$ and $R^{1c}$ are independently selected from:
  (a) hydrogen,
  (b) hydroxy,
  (c) halogen,
  (d) $C_{1-6}$alkyl, which is unsubstituted or substituted with substituents selected from: hydroxy, cyclopropyl, cyclobutyl, cyclopentyl, azetidinyl, fluoro, —$OCH_3$, —$OCH_2CH_2OCH_3$, —(C=O)—$C_{1-6}$alkyl, —$NH_2$, —NH($C_{1-6}$alkyl), —N($C_{1-6}$ alkyl)$_2$, and —N($C_{3-6}$cycloalkyl),
  (e) —O—$C_{1-6}$alkyl, which is unsubstituted or substituted with substituents selected from: hydroxy, cyclopropyl, cyclobutyl, cyclopentyl, azetidinyl, fluoro, —$OCH_3$, —$NH_2$, —NH($C_{1-6}$alkyl), —N($C_{1-6}$alkyl)$_2$, —N($C_{3-6}$cycloalkyl), and —NH(C=O)($C_{1-6}$alkyl),
  (f) $C_{3-6}$cycloalkyl, which is unsubstituted or substituted with substituents selected from: $C_{1-6}$alkyl, hydroxy, cyclopropyl, cyclobutyl, cyclopentyl, azetidinyl, fluoro, —$OCH_3$, —$NH_2$, —NH($C_{1-6}$ alkyl), —N($C_{1-6}$alkyl)$_2$, and —N($C_{3-6}$ cycloalkyl), (g) —NH$_2$,
(h) —NH(C$_{1-6}$ alkyl),
(i) —NH(C$_{2-6}$alkyl)-OH,
(j) —N(C$_{1-6}$alkyl)$_2$,
(k) —N(C$_{3-6}$cycloalkyl),
(l) —SO$_2$—C$_{1-6}$alkyl,
(m) —(C=O)H,
(n) —(C=O)—C$_{1-6}$alkyl,
(o) —(C=O)O—C$_{1-6}$alkyl, and
(p) —CN;

R$^2$ and R$^3$ are independently selected from:
(1) hydrogen,
(2) fluoro,
(3) hydroxy, and
(4) —CH$_3$;

R$^4$ is hydrogen or methyl;

R$^7$ and R$^8$ are independently selected from:
(1) hydrogen,
(2) C$_{1-6}$alkyl, which is unsubstituted or substituted with substituents selected from: hydroxy, fluoro, and —OCH$_3$,
(3) —CH=CH$_2$,
(4) cyclopropyl,
(5) -fluoro,
(6) -chloro,
(7) -bromo,
(8) —CN,
(9) —(C=O)H, and
(10) —(C=O)O—C$_{1-6}$alkyl;

R$^9$ is selected from:
(1) hydrogen,
(2) —C$_{1-6}$alkyl, which is unsubstituted or substituted with substituents selected from: hydroxy, methoxy, fluoro, —C(C=O)O—C$_{1-6}$alkyl, —CN, —NH$_2$, —NH(C$_{1-6}$alkyl), —N(C$_{1-6}$alkyl)$_2$, —C(C=O)NH$_2$, —C(C=O)OH, —SO$_2$C$_{1-6}$alkyl, oxetanyl, or pyridyl;
(3) —C$_{3-6}$cycloalkyl, which is unsubstituted or substituted with substituents selected from: hydroxy, and C$_{1-6}$alkyl-hydroxy,
(4) oxetanyl,
(6) tetrahydrofuranyl, and
(6) —C(C=O)O—C$_{1-6}$alkyl;

each of R$^{10}$ and R$^{11}$ is independently selected from:
(1) hydrogen,
(2) —OH,
(3) —CH$_3$,
(4) —CH$_2$OH,
(5) —CH$_2$CH$_2$OH, and
(6) —C(CH$_3$)$_2$OH,
or R$^{10}$ and R$^{11}$ taken together form a cyclopropyl group, a=CH$_2$ group or a keto group,
or R$^9$ and R$^{10}$ taken together form a piperidine, piperazine or morpholine ring, which is unsubstituted or substituted with substituents selected from: hydroxy, methoxy, and —C$_{1-6}$alkyl;
or a pharmaceutically acceptable salt thereof.

2. The compound of claim 1, or a pharmaceutically acceptable salt thereof, wherein R$^1$ is selected from:
(a) C$_{1-6}$alkyl, which is unsubstituted or substituted with cyclopropyl, methyl-cyclopropyl, dimethyl-cyclopropyl, methyl-fluoro-cyclopropyl, methyl-difluoro-cyclopropyl, or dimethyl-difluoro-cyclopropyl,
(b) indazole, which is unsubstituted or substituted with C$_{1-3}$alkyl,
(c) tetrahydroisobenzofuranyl, which is unsubstituted or substituted with C$_{1-3}$alkyl,
(d) phenyl, which is unsubstituted or substituted with C$_{1-3}$alkyl or —CN, and
(e) pyridyl, which is unsubstituted or substituted with C$_{1-3}$alkyl or —O—C$_{1-3}$alkyl.

3. The compound of claim 1, or a pharmaceutically acceptable salt thereof, wherein R$^1$ is —CH$_2$-(methyl)cyclopropyl.

4. The compound of claim 1, or a pharmaceutically acceptable salt thereof, wherein R$^2$ is hydrogen, R$^3$ is hydrogen, and R$^4$ is hydrogen.

5. The compound of claim 1, or a pharmaceutically acceptable salt thereof, wherein R$^7$ is —CH$_3$.

6. The compound of claim 1, or a pharmaceutically acceptable salt thereof, wherein R$^8$ is —CH$_3$.

7. The compound of claim 1, or a pharmaceutically acceptable salt thereof, wherein R$^9$ is selected from:
(1) hydrogen, and
(2) —C$_{1-6}$alkyl, which is unsubstituted or substituted with hydroxy, methoxy, 1-3 fluoro.

8. The compound of claim 1, or a pharmaceutically acceptable salt thereof, wherein R$^9$ and R$^{10}$ taken together form a piperidine ring, which is unsubstituted or substituted with substituents selected from: hydroxyl and methyl.

9. The compound of claim 1, or a pharmaceutically acceptable salt thereof, wherein R$^{10}$ is hydrogen and R$^{11}$ is hydrogen.

10. A compound which is selected from:
3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one;
3-methyl-2-(5-((1-methylcyclopropyl)methoxy)-2-azabicyclo[4.1.0]heptan-2-yl)-6,7-dihydro-5H-pyrrolo[3,4-b]pyridin-5-one;
7-(hydroxymethyl)-3,4,6-trimethyl-2-(5-((1-methylcyclopropyl)methoxy)-2-azabicyclo[4.1.0]-heptan-2-yl)-6,7-dihydro-5H-pyrrolo[3,4-b]pyridin-5-one;
3-ethyl-7-(hydroxymethyl)-6-methyl-2-(5-((1-methylcyclopropyl)methoxy)-2-azabicyclo-[4.1.0]heptan-2-yl)-6,7-dihydro-5H-pyrrolo[3,4-b]pyridin-5-one;
6-(2-hydroxyethyl)-3,4-dimethyl-2-(5-((1-methylcyclopropyl)methoxy)-2-azabicyclo[4.1.0]-heptan-2-yl)-6,7-dihydro-5H-pyrrolo[3,4-b]pyridin-5-one;
3-(3,4-dimethyl-2-(5-((1-methylcyclopropyl)methoxy)-2-azabicyclo[4.1.0]heptan-2-yl)-5-oxo-5,7-dihydro-6H-pyrrolo[3,4-b]pyridin-6-yl)propanenitrile;
3,4-dimethyl-2-(5-((1-methylcyclopropyl)methoxy)-2-azabicyclo[4.1.0]heptan-2-yl)-6-(2-(methyl sulfonyl)ethyl)-6,7-dihydro-5H-pyrrolo[3,4-b]pyridin-5-one;
6-(2-hydroxy-2-methylpropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one;
9-hydroxy-3,4-dimethyl-2-(5-((1-methylcyclopropyl)methoxy)-2-azabicyclo[4.1.0]heptan-2-yl)-8,9,10,10a-tetrahydropyrido[2,3-a]indolzin-5(7H)-one;
9-hydroxy-3,4,9-trimethyl-2-(5-((1-methylcyclopropyl)methoxy)-2-azabicyclo[4.1.0]heptan-2-yl)-8,9,10,10a-tetrahydropyrido[2,3(7H)-one;
3,4-dimethyl-2-(5-((1-methylcyclopropyl)methoxy)-2-azabicyclo[4.1.0]heptan-2-yl)-7,8,10,10a-tetrahydro-5H-pyrido[2',3':3,4]pyrrolo[2,1-c][1,4]oxazin-5-one;
2-(5-((1,3-dihydroisobenzofuran-5-yl)oxy)-2-azabicyclo[4.1.0]heptan-2-yl)-3,4-dimethyl-6,7-dihydro-5H-pyrrolo[3,4-b]pyridin-5-one;
2-(5-((1,3-dihydroisobenzofuran-5-yl)oxy)-2-azabicyclo[4.1.0]heptan-2-yl)-3-methyl-6,7-dihydro-5H-pyrrolo[3,4-b]pyridin-5-one;

2-(5-(isochroman-6-yloxy)-2-azabicyclo[4.1.0]heptan-2-yl)-3-methyl-6,7-dihydro-5H-pyrrolo[3,4-b]pyridin-5-one;

3,4-dimethyl-2-(5-((1-methyl-1H-pyrazol-4-yl)oxy)-2-azabicyclo[4.1.0]heptan-2-yl)-6,7-dihydro-5H-pyrrolo[3,4-b]pyridin-5-one;

2-(5-(isochroman-7-yloxy)-2-azabicyclo[4.1.0]heptan-2-yl)-3,4-dimethyl-6,7-dihydro-5H-pyrrolo[3,4-b]pyridin-5-one;

2-(5-(isochroman-7-yloxy)-2-azabicyclo[4.1.0]heptan-2-yl)-3-methyl-6,7-dihydro-5H-pyrrolo[3,4-b]pyridin-5-one;

2-(5-((1,3-dihydroisobenzofuran-5-yl)oxy)-2-azabicyclo[4.1.0]heptan-2-yl)-3,4,6-trimethyl-6,7-dihydro-5H-pyrrolo[3,4-b]pyridin-5-one;

9-hydroxy-3,4,9-trimethyl-2-(5-((1-methylcyclopropyl)methoxy)-2-azabicyclo[4.1.0]heptan-2-yl)-8,9,10,10a-tetrahydropyrido[2,3-a]indolizin-5(7H)-one;

6-(2-hydroxypropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one;

6-(2-(hydroxymethyl)cyclopropyl)-3,4-dimethyl-2-(5-((1-methylcyclopropyl)methoxy)-2-azabicyclo[4.1.0]heptan-2-yl)-6,7-dihydro-5H-pyrrolo[3,4-b]pyridin-5-one;

3,4-dimethyl-2-(54(1-methylcyclopropyl)methoxy)-2-azabicyclo[4.1.0]heptan-2-yl)-6-(tetrahydrofuran-3-yl)-6,7-dihydro-5H-pyrrolo[3,4-b]pyridin-5-one; and 2-(5-(isochroman-6-yloxy)-2-azabicyclo[4.1.0]heptan-2-yl)-3,4-dimethyl-6,7-dihydro-5H-pyrrolo[3,4-b]pyridin-5-one;

or a pharmaceutically acceptable salt thereof.

11. A pharmaceutical composition which comprises an inert carrier and a compound of claim 1 or a pharmaceutically acceptable salt thereof.

12. A method for the treatment of a neurological and/or psychiatric disorder associated with muscarinic acetylcholine receptor dysfunction in a mammal comprising the step of administering at least one compound of claim 1, or a pharmaceutically acceptable salt of said compound, to a patient in need thereof in an amount effective to treat said disorder.

13. The method of claim 12, wherein the mammal has been diagnosed with a need for treatment of the disorder prior to the administering step.

14. The method of claim 12, wherein the disorder is a neurological and/or psychiatric disorder associated with mAChR M4 dysfunction.

15. The method of claim 12, wherein the disorder is a psychotic disorder.

16. The method of claim 15, wherein the psychotic disorder is selected from schizophrenia, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder.

17. The method of claim 12, wherein the disorder is a cognitive disorder.

18. The method of claim 17, wherein the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS dementical complex, dementia of the Alzheimer's type, age-related cognitive decline, and mild cognitive impairment.

* * * * *